United States Patent [19]

Heagy et al.

[11] Patent Number: 5,753,516
[45] Date of Patent: May 19, 1998

[54] SCREENING METHOD FOR LIGANDS OF THE EBI-1 RECEPTOR

[76] Inventors: Wyrta E. Heagy, 536 Janalyn Cir., Golden Valley, Minn. 55427; Robert W. Finberg, 48 Spring La., Canton, Mass. 02021

[21] Appl. No.: 383,751

[22] Filed: Feb. 3, 1995

[51] Int. Cl.$^6$ .................... G01N 33/566; C12Q 1/68; C01N 33/53
[52] U.S. Cl. .................. 436/501; 435/6; 435/7.1; 435/7.2; 435/7.8; 530/350.1
[58] Field of Search .................. 436/501; 435/6.9, 435/1.2, 7.1, 7.2, 7.8; 536/22.1, 23.1; 530/350, 350.1; 424/144.1

[56] References Cited

FOREIGN PATENT DOCUMENTS

| | | | |
|---|---|---|---|
| 0 612 845 | 8/1994 | European Pat. Off. | C12N 15/12 |
| WO 94/11500 | 5/1994 | WIPO | C12N 15/12 |
| WO 94/12519 | 6/1994 | WIPO | |

OTHER PUBLICATIONS

Heagy et al, "Opioid receptor agonists and Ca modulation in human B cell lines", J. Immunol. 149:4074–4081, Dec. 1992.

Sharp et al, "Expression of opiod receptor by immune cells", J. Neuroimmunol. 69:3–13, 1996.

Marullo et al, "Human B2 adrenergic receptors expressed in Escherichia coil membranes retain their pharmacologica properties", Proc. Natl. Acad. Sci. 85:7551–7555, Oct. 1988.

Bidlack et al, "K–opioid binding sites on a murine lymphoma cell line", Eur. J. Pharm. 227:257–265, 1992.

Schweickart et al, "Cloning of human and mouse EBI1, a lymphoid specific g–protein coupled receptor encoded on human chromosome 17q12–a21.2", Genomics 23:643–650, 1994.

Payette et al, "Expression and pharmacological characterization of the human M1 muscarinic receptor in Sacchromyces cerevisiae", FEBS Lett. 266:21–25, Jun. 1990.

House et al, "In vitro evaluation of fentanyl and meperidine for immunomodulatory activity", Immunol. Lett. 46:117–124, 1995.

Bergelson et al., "Identification of the Integrin VLA–2 as a Receptor for Echovirus 1," Science, 255:1718–1720, 1992.

Birkenbach et al., "Epstein–Barr Virus–Induced Genes: First Lymphocyte–Specific G Protein Coupled Peptide Receptors," J. Virol., 67(4):2209–2220, 1993.

Borboni et al., "β–Endorphin Receptors on Cultured and Freshly Isolated Lymphocytes from Normal Subjects," Biochem. biophys. Res. Commun., 163(1):642–648, 1989.

Bradbury et al., "The CD19 Signal Transduction Complex of B Lymphocytes: Deletion of the CD19 Cytoplasmic Domain Alters Signal Transduction but Not Complex Formation with TAPA–1 and Leu 13," J. Immunol., 151(6):2915–2927, 1993.

Bryant et al., "Morphine–Induced Immunomodulation is Not Related to Serum Morphine Concentrations," E.J. Pharmacol., 149:165–169, 1988.

Carlson et al., "Thrombin and Phorbol Esters Cause the Selective Phosphorylation of a G Protein Other Than $G_i$ in Human Platelets," J. Biol. Chem., 264(22):13298–13305, 1989.

Carr et al., "Evidence for κ–Class Opioid Receptor on Cells of the Immune System," Cell. Immunol., 116:44–51, 1988.

Chang et al., "Dissection of the Human CD2 Intracellular Domain," J. Exp. Med., 169:2073–2083, 1989.

Chang et al., "Interaction of Enkephalin with Opiate Receptors in Intact Cultured Cells," Mol. Pharmoc., 14:961–970, 1978.

Chao et al., "Lethality of Morphine in Mice Infected with Toxoplasma gondii," J. Pharmacol. Exp. Ther., 252(2):605–609, 1990.

Chen et al., "Molecular Cloning and Functional Expression of a μ–Opioid Receptor from Rat Brain," Mol. Pharm., 44:8–12, 1993.

Chen et al., "Molecular Cloning of a Rat κ Opioid Receptor Reveals Sequence Similarities to the μ and δ Opioid Receptors," Biochem J., 295:625–628, 1993.

Chen et al., "Molecular Cloning, Tissue Distribution and Chromosomal Localization of a Novel Member of the Opioid Receptor Gene Family," FEBS Lett., 347:279–283, 1994.

Chen and Yu, "Differential Regulation by cAMP–dependent Protein Kinase and Protein Kinase C of the μ Opioid Receptor Coupling to a G Protein–activated $K^{+Channel}$," J. Biol. Chem., 269(11):7839–7842, 1994.

Corbett et al., "Selectivities of Opioid Peptide Analogues as Agonists and Antagonists at the κ–Receptor," Br. J. Pharmacol., 83:271–279, 1984.

Dohlman, H.G., "Model Systems for the Study of Seven––Transmembrane–Segment Receptors," Annu. Rev. Biochem., 60:653–688, 1991.

Dohlman et al., "A Family of Receptors Coupled to Guanine Nucleotide Regulatory Proteins," Biochemistry, 26(10):2657–2664, 1987.

Evans et al., "Cloning of a Delta Opioid Receptor by Functional Expression," Science, 258:1952–1955, 1992.

Fóris et al., "Concentration–Dependent Effect of Met–Enkephalin on Human Polymorphonuclear Leukocytes," Ann. N.Y. Acad. Sci., 496:151–157, 1987.

Forsyth, K.D., "Anti–CD9 Antibodies Augment Neutrophil Adherence to Endothelium," Immunol., 72:292–296, 1991.

Frielle et al., "Structural Basis of β–adrenergic Receptor Subtype Specificity Studied with Chimeric β1/β2–adrenergic Receptors," Proc. Natl. Acad. Sci. USA, 85:9494–9498, 1988.

(List continued on next page.)

Primary Examiner—W. Gary Jones
Assistant Examiner—Jeffrey Fredman

[57] ABSTRACT

This invention relates primarily to opioid binding proteins specifically, the invention relates to lymphocyte-specific opioid recognition sites and methods and compositions related to them. For example, methods of determining agonists and antagonists of immune cell-specific opioid binding protein are presented.

15 Claims, 20 Drawing Sheets

OTHER PUBLICATIONS

Fujioka et al., "Purification and Reconstitution of μ-opioid Receptors in Liposome" *J. Chromat.*, 597:429–433, 1992.

Fukuda et al., "Primary Structures and Expression from cDNAs of Rat Opioid Receptor κ-and μ-subtypes," *FEBS Lett.*, 327(3)311–314, 1993.

Gilmore et al., "The Role of Opioid Peptides in Immunomodulation," *Ann. N.Y. Acad. Sci.*, 597:252–263, 1990.

Gioannini et al., "Evidence for the Presence of Disulfide Bridges in Opioid Receptors Essential for Ligand Binding. Possible Role in Receptor Activation," *J. Mol. Recogn.*, 2(1):44–48, 1989.

Heagy et al., "Opioid Receptor Agonists and $Ca^{2+}$ Modulation in Human B Cell Lines," *J. Immunol.*, 149(12):4072–4081, 1992.

Heagy et al., "Neurohormones Regulate T Cell Function," *J. Exp. Med.*, 171:1625–1633, 1990.

Kieffer et al.,"The δ–opioid Receptor: Isolation of a cDNA by Expression Cloning and Pharmacological Characterization," *Proc. Natl. Acad. Sci. USA*, 89:12048–12052, 1992.

Kong et al., "A Single Residue, Aspartic Acid 95, in the δ Opioid Receptor Specifies Selective High Affinity Agonist Binding," *J. Biol. Chem.*, 268(31):23055–23058, 1993.

Lane et al., "Regulation of an Opioid–binding Protein in NG108–15 Cells Parallels Regulation of δ–opioid Receptors," *Proc. Natl. Acad. Sci. USA*, 89:11234–11238, 1992.

Li et al., "Cloning of a Cellular Factor, Interleukin Binding Factor, That Binds to NFAT–like Motifs in the Human Immunodeficiency Virus Long Terminal Repeat,"*Proc. Natl. Acad. Sci. USA*, 88:7739–7743, 1991.

Li et al., "Purification of Opioid Receptor in the Presence of Sodium Ions," *Life Sciences*, 51(15):1177–1185, 1992.

Lippman et al., "Opioid–binding Cell Adhesion Molecule (OBCAM)–related Clones from a Rat Brain cDNA Library," *Gene*, 117:249–254, 1992.

Loh et al., "Molecular Characterization of Opioid Receptors," *Annu. Rev. Pharmacol. Toxicol.*, 30:123–147, 1990.

Lu et al., "The Effects of Agranulocytic and Nonagranulocytic Drugs in Rabbits Concurrently Treated with Busulfan (Myleran) III. Thiouracil, Morphine, and Penicillin," *Toxicology and Applied Pharmacology*, 2:171–182, 1960.

Lutz et al., "Opioid Receptors and Their Pharmacological Profiles," *J. Receptor Research*, 12(3):267–286, 1992.

Madden et al., "Binding of Naloxone to Human T-Lymphocytes," *Biochem. Pharmacol.*, 36(23):4103–4109, 1987.

Maneckjee et al., "Nonconventional Opioid Binding Sites Mediate Growth Inhibitory Effects of Methadone on Human Lung Cancer Cells," *Proc. Natl. Acad. Sci. USA*, 89:1169–1173, 1992.

Maneckjee et al., "Characterization of a Polyclonal Antibody to the μ Opioid Receptor," *Journal of Neuroimmunology*, 17:199–208, 1988.

Mansour et al., "Anatomy of CNS Opioid Receptors," *Trends in Neurosci.*, 7:2445–2453, 1987.

Manzanares et al., "Kappa–Opioid–Receptor–Mediated Regulation of α–Melanocyte–Stimulating Hormone Secretion and Tuberohypophysial Dopaminergic Neuronal Activity," *Neuroendocrinology*, 52:200–205, 1990.

Mierendorf et al., "Gene Isolation by Screening λgt11 Libraries with Antibodies," *Methods in Enzymology*, 152:458–469, 1987.

Mitamura et al., "The 27–kD Diphtheria Toxin Receptor–Associated Protein (DRAP27) from Vero Cells is the Monkey Homologue of Haman CD9 Antigen: Expression of DRAP27 Elevates the Number of Diphtheria Toxin Receptors on Toxin–Sensitive Cells," *J. Cell. Biol.*, 118(6):1389–1399, 1992.

Miyake et al., "Identification of the Motility–Related Protein (MRP–1), Recognized by Monoclonal Antibody M31–15, Which Inhibits Cells Motility," *J. Exp. Med.*, 174:1347–1354, 1991.

Moore, T.C., "Modification of Lymphocyte Traffic by Vasoactive Neurotransmitter Substances," *Immunol.*, 52:511–518, 1984.

Nakajima et al., "Direct Linkage of Three Tachykinin Receptors to Stimulation of Both Phosphatidylinositol Hydrolysis and Cyclic AMP Cascades in transfected Chinese Hamster Ovary Cells," *J. Biol. Chem.*, 267:2437–2442, 1992.

Nock et al., "Autoradiography of [$^3$H]U–69593 Binding Sites in Rat Brain: Evidence for κ Opioid Receptor Subtypes," *Eur. J. Pharmacol.*, 154:27–34, 1988.

Ott et al., "Opioid Receptors of Neuroblastoma Cells Are in Two Domains of the Plasma Membrane That Differ in Content of G Proteins,"*J. Neurochem.*, 52:619–626, 1989.

Parma et al., "Somatic Mutations in the Thyrotropin Receptor Gene Cause Hyperfunctioning Thyroid Adenomas," *Nature*, 365:649–651, 1993.

Porreca et al., "Modulation of Mu–Mediated Antinociception on the Mouse Involves Opioid Delta–2–Receptors," *J. Pharmacol. Exp. Ther.*, 263(1):147–152, 1992.

Probst et al., "Sequence Alignment of the G–Protein Coupled Receptor Superfamily," *DNA and Cell Biology*, 11(1):1–20, 1992.

Sambrook et al., "Expression of Cloned Genes in Cultured Mammalian Cells," in: *Molecular Cloning*, Cold Spring Harbor Laboratory Press, Publisher, J. Sambrook et al., Editors, Second Edition, vol. 3, Chpt. 16, pp. 16.1–16.20, 1987.

Schofield et al., "Molecular Characterization of a New Immunoglobulin Superfamily Protein with Potential Roles in Opioid Binding and Cell Contact," *The EMBO Journal*, 8(2):489–495, 1989.

Shenker et al., "A Constitutively Activating Mutation of the Luteinizing Hormone Receptor in Familial Male Precocious Puberty," *Nature*, 365:652–654, 1993.

Shimizu et al., "Lymphocyte Interactions with Endothelial Cells," *Immunol. Today*, 13(3):106–112, 1992.

Shipp et al., "Common Acute Lymphoblastic Leukemia Antigen (CALLA) Is Active Neutral Endopeptidase 24.11 (Enkephalinase): Direct Evidence by cDNA Transfection Analysis," *Proc. Natl. Acad. Sci. USA*, 86:297–301, 1989.

Shipp et al., "Down Regulation of Enkephalin–Mediated Inflammatory Responses by CD10/Neutral Endopeptidase 24.11," *Nature*, 347:394–396, 1990.

Simon, E.J., "Opioid Receptors and Endogenous Opioid Peptides," *Medicinal Res. Rev.*, 11(4):357–374, 1991.

Soong et al., "Structure and Functional Expression of a Member of the Low Voltage–Activated Calcium Channel Family," *Science*, 260:1133–1136, 1993.

Stein et al., "Local Analgesic Effect of Endogenous Opioid Peptides," *The Lancet*, 342:321–324, 1993.

Taub et al., "Immunomodulatory Activity of μ–and κ–Selective Opioid Agonists," *Proc. Natl. Acad. Sci. USA*, 88:360–364, 1991.

Traynor et al., "δ–Opioid Receptor Subtypes and Cross–Talk with μ–Receptors," *Trends in Pharmac. Sci.,* 14:84–86, 1993.

Unterwald et al., "Neuroanatomical Localization of $\kappa_1$ and $\kappa_2$ Opioid Receptors in Rat and Guinea Pig Brain," *Brain Res.,* 562:57–65, 1991.

Vaughn et al., "Differentiation Between Rat Brain and Mouse Vas Deferens δ–Opioid Receptors," *European J. Pharmacol.,* 177:99–101, 1990.

Wu et al., "G Protein–Coupled Signal Transduction Pathways of Interleukin–8," *Science,* 261:101–103, 1993.

Wybran et al., "Suggestive Evidence for Receptors for Morphine and Methionine–Enkephalin on Normal Human Blood T Lymphocytes," *J. Immunol.,* 123(3):1068–1070, 1979.

Xie et al., "Expression Cloning of cDNA Encoding a Seven–helix Receptor from Human Placenta with Affinity for Opioid Ligands," *Proc. Natl. Acad. Sci. USA,* 89:4124–4128, 1992.

Yamada et al., "Cloning and Functional Characterization of a Family of Human and Mouse Somatostatin Receptors Expressed in Brain, Gastrointestinal Tract, and Kidney," *Proc. Natl. Acad. Sci. USA,* 89:251–255, 1992.

Yasuda et al., "Cloning of Novel Somatostatin Receptor, SSTR3, Coupled to Adenylcyclase," *J. Biol. Chem.,* 267(28):20422–20428, 1992.

Yasuda et al., "Cloning and Functional Comparison of κ and δ Opioid Receptors from Mouse Brain," *Proc. Natl. Acad. Sci. USA,* 90:6736–6740, 1993.

Ye et al., "Modulation of Lymphocyte Motility by β–Endorphin and Met–Enkephalin," *Immunopharmacology,* 17:81–89, 1989.

Zagon et al., "Modulation of Murine Neuroblastoma in Nude Mice by Opioid Antagonists," *J. Natl. Cancer Inst.,* 78(1):141–147, 1987.

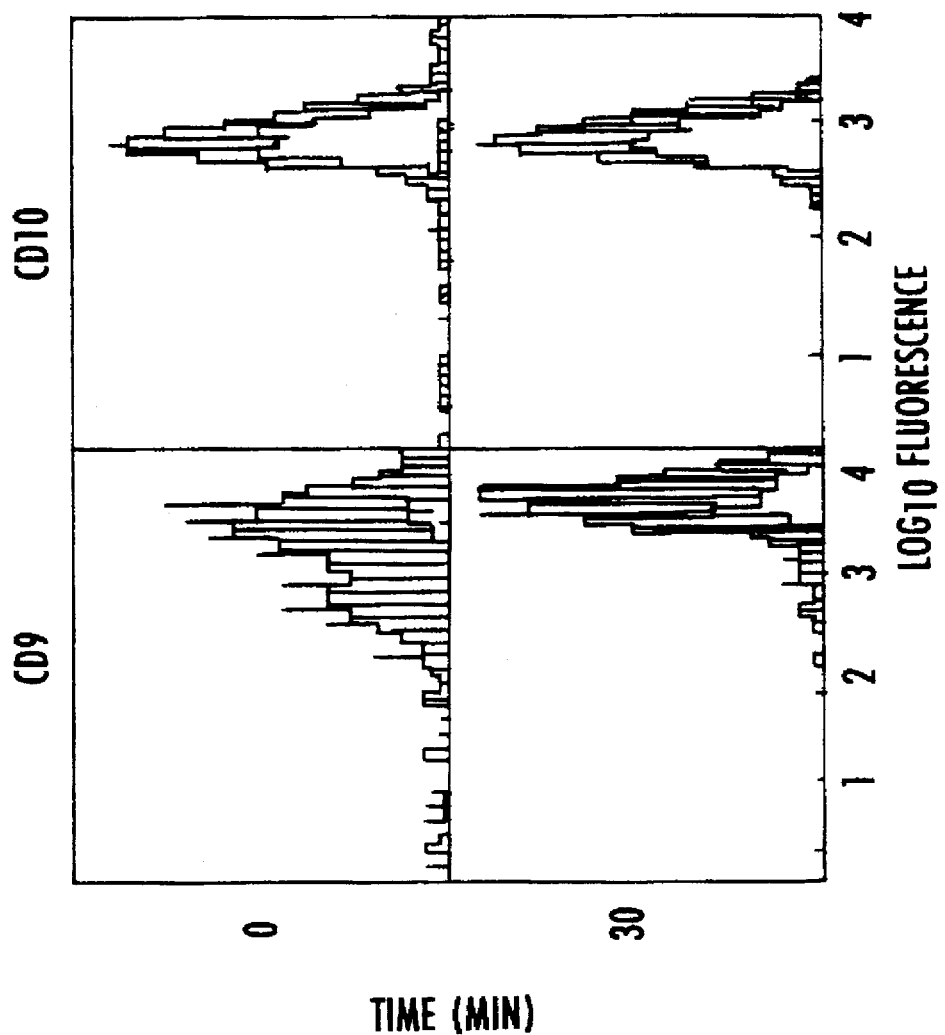

R1=3.3X10$^{-12}$M(9X10$^2$ SITES/CELL); KD=1.4X10$^{-8}$M
R2=1.0X10$^{-10}$M(3X10$^4$ SITES/CELL); KD=1.8X10$^{-7}$M

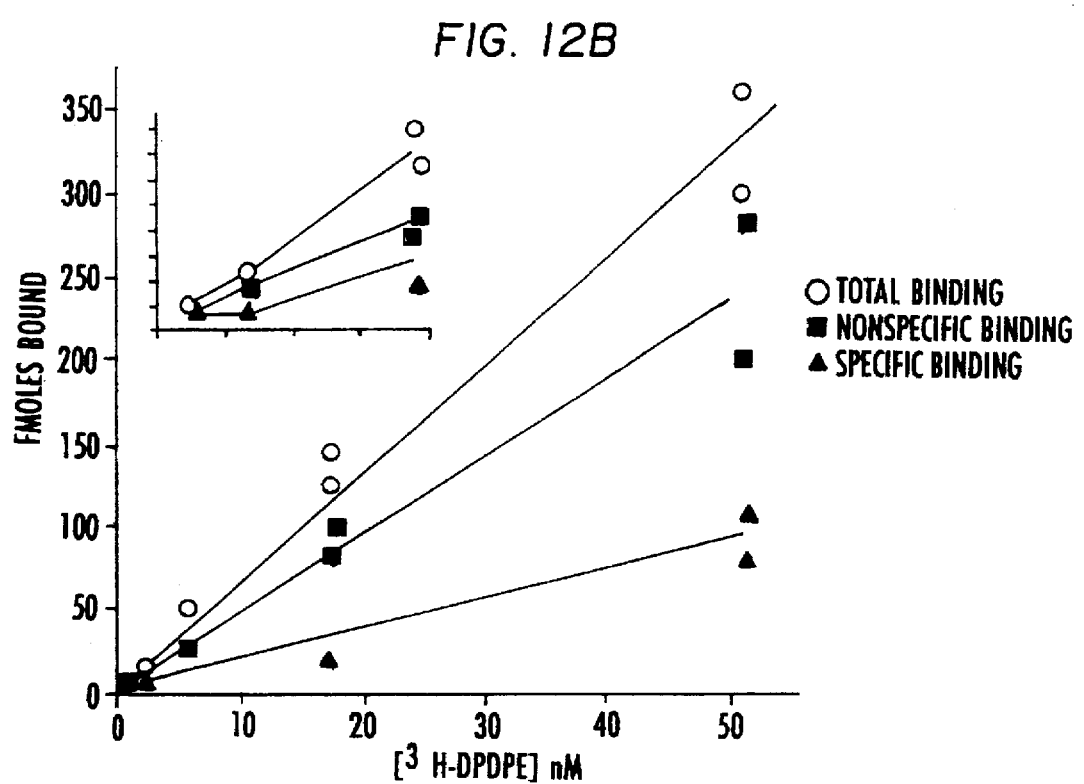
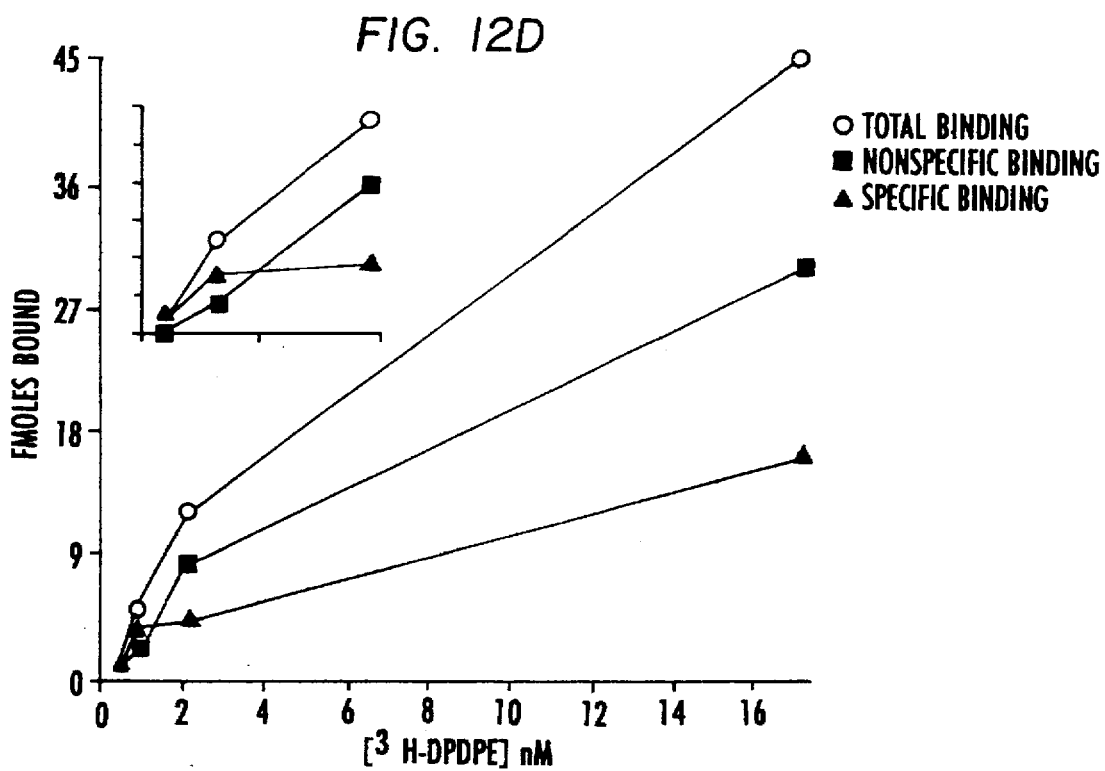

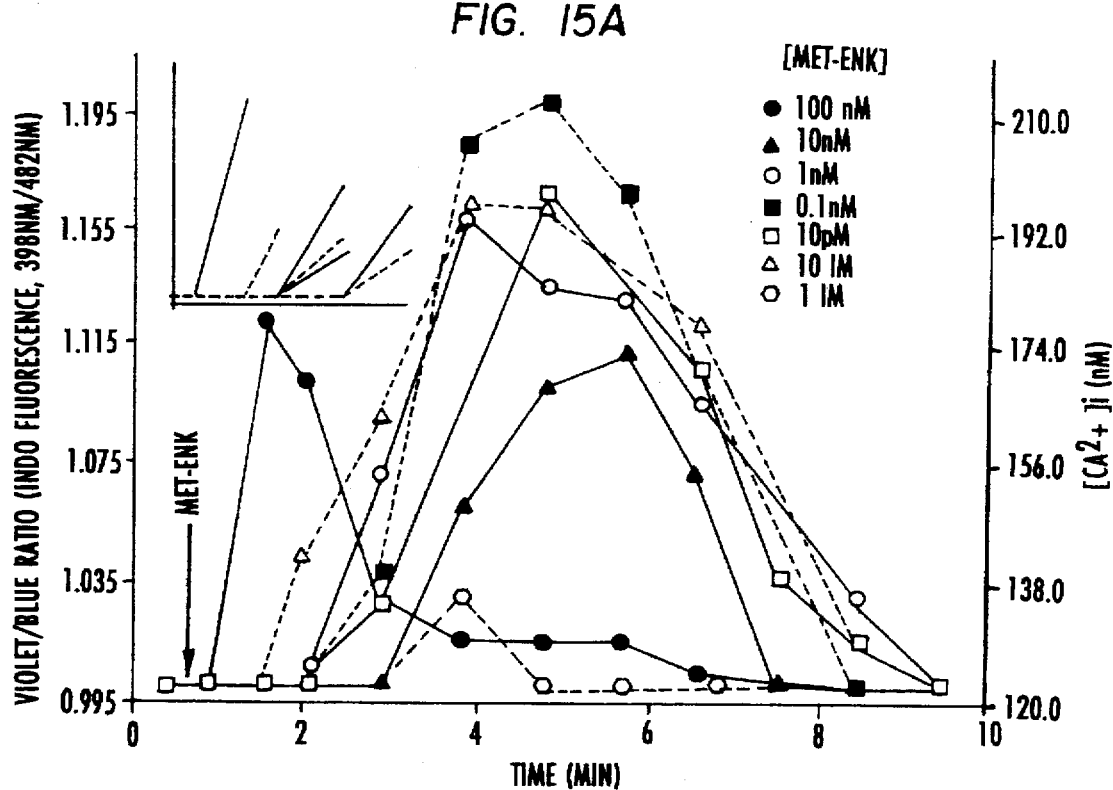

FIG. 17

| | |
|---|---|
| LOR (120) | LTYIYFKRLKTMTDTYLLNLAVADILFLLTLPFWAYSAAK |
| ROR-C (110) | VILVMYRHTKMKTATNIYIFNLALADTLVLLTLPFQGTDILLG |
| ROR-δ (112) | VNFGIVRYTKLKTATNIYIFNLALADALATSTLPFQSAKYLME |
| ROR-μ (131) | VMYVIVRYTKLKTATNIYFNLALADALATSTLPFQSVNYLMG |
| ROR-H | LVFVIVRYTKMKTTTATNIYIFNLALADALVTTTMPFQSAVYLMN |
| hORL1 (114) | VMYVITLRHTKMKTATNIYIFINLALADTLVLLTLPFQGTDILLG |

LOR=LYMPHOCYTE OR
ROR-C=RAT ORPHAN RECEPTOR WITH NO KNOWN LIGAND SPECIFICITY
ROR-δ=RAT, OR-g
ROR-μ=RAT, OR-μ
ROR-κ=RAT, OR-κ
hORL1=HUMAN ORPHAN CLONE WITH NO KNOWN LIGAND SPECIFICITY

SCREENING METHOD FOR LIGANDS OF THE EBI-1 RECEPTOR

The government has rights to this work pursuant to National Institutes of Health Grant R01A129657.

BACKGROUND OF THE INVENTION

A. Field of the Invention

This invention relates generally to the field of opioid recognition sites, genes encoding opioid binding proteins, opioid receptor agonists and antagonists and methods of/for invoking opioid receptor activation. Specifically, the invention relates to opioid recognition sites expressed on immune cells such as EBI1, a novel lymphocyte opioid binding protein identified as such by the inventors.

B. Background of Related Art

The existence of endogenous morphomimetic agents was suspected for many years prior to their actual discovery in 1973. Since then three families of peptide neurohormones have been described, each deriving from a distinct precursor molecule: the enkephalins, from preproenkephalin; the endorphins, from proopiomelanocortin; and the dynorphins, from prodynorphin. There are more than 20 endogenous peptides; all derived from these precursors. All these peptides bind to specific membrane receptors located throughout the central and peripheral nervous system.

The opioid neurohormones are the body's natural analgesics and modulate a variety of physiologic events in the central nervous system (CNS) and immune system (Sibinga and Goldstein, 1988; Manzanares et al., 1990; Gilmore et al., 1990; Pasternak, 1993; Stein et al., 1993). They are involved in the regulation of moods, behaviors, higher cognitive processes, reproduction, pain control, inflammatory and stress responses, and a variety of immune functions (Sibinga and Goldstein, 1988; Manzanares et al., 1990; Gilmore et al., 1990; Pasternak, 1993; Stein et al., 1993). Stress is a suspected risk factor in the incidence and severity of disease, however, the mechanisms that directly link stress-states and pathology are complex and, at present, poorly understood. Stress-related stimuli initiate the synthesis and release of opioid peptides (Sibinga and Goldstein, 1988; Gilmore et al., 1990), which when exogenously administered in animal models of infectious disease, increase morbidity and mortality (Shavit et al., 1985; Chao et al., 1990). Although the available evidence is circumstantial, it is plausible that stress induced-release of the endogenous opioid peptides is a contributing factor in the pathogenesis of human disease.

Opiates and other opioid drugs have various effects on the perception of pain, consciousness, motor control, mood, autonomic function the immune response and can also induce physical dependence (Koob, et al 1992). These agents exert effects on the endocrine, cardiovascular, respiratory, gastrointestinal and immune systems (Olson, et al 1989). They, like the endogenous opioids bind to specific membrane-associated receptors located throughout the central and peripheral nervous system (Pert, et al. 1973); (Hughes, et al. (1975); Akil, et al. (1984)). Although the endogenous opioid peptide neurohormones belong to a class of molecules distinct from opiates, they share common structural features including a positive charge juxtaposed with an aromatic ring that is required for interaction with the opioid receptors (Bradbury, et al. 1976).

Within the CNS opiates and opioid peptides bind to a number of opiate/opioid receptor types ($\mu$, $\delta$, $\kappa$, $\sigma$), as well as a number of subtypes (e.g., $\mu1$, $\mu2$, $\delta1$, $\delta2$, $\kappa1$, $\kappa2$) (Pasternak, 1993). The morphinomimetic activity characteristic of the opioid peptides is dependent on their $NH_2$ terminal sequence (Tyr-Gly-Gly-Phe-Met or -Leu) and is blocked by classical opiate receptor antagonists such as naloxone (Pasternak, 1993). In the periphery opiate/opioid receptors are found on neurons, reproductive and gut tissues and immune cells (Gilmore et al., 1990; Pasternak, 1993; Borboni et al., 1989; Vaughn et al., 1990). Leukocytes have been shown to express both classical (naloxone-sensitive) and nonclassical (naloxone-insensitive) opiate/opioid recognition sites (Gilmore et al., 1990; Borboni et al., 1989). Early attempts to clone cDNAs encoding opioid receptors were unsuccessful. A cDNA encoding an opioid-binding protein (OBCAM) with $\mu$ selectivity was isolated (Schofield, et al. (1989)), but the predicted protein lacked transmembrane domains, presumed necessary for signal transduction. Several laboratories have now reported the cloning of opiate receptor cDNA from rodent (rat/mouse) neurohybridomas or brain, and recently, from human CNS tissues. The deduced protein sequences for these receptors reveal a similarity to other membrane proteins belonging to a large superfamily of R7G receptors. All members of this super family have amino acid sequences that suggest they have seven distinct regions that lie embedded within the cell membrane. All previously described opioid receptors belong to one subfamily of R7G receptors (i.e., exhibit$\geq$85% homology). When expressed in COS cells and activated with opiate receptor agonists the opioid receptors couple with $G_o a$ or $G_i a$ subunits of pertussis toxin-sensitive GTP-binding regulatory (G) proteins and diminish adenylyl cyclase activity (e.g., decrease intracellular levels of CAMP).

The classes of opioid receptors differ in their affinity for various opiate/opioid ligands and in their cellular distribution. The different classes of opioid receptors are believed to serve distinct physiological functions (Olson, et al., 1989; Simon 1991; Lutz & Pfister 1992). However, up until now it has been understood that there is substantial overlap of function as well as of distribution. Biochemical characterization of isolated opioid receptor proteins suggest that all three subtypes have a molecular mass of $\approx$60,000 Da and that they may be structurally related (Loh, et al. (1990)). Moreover, the similarity between the receptor subtypes is supported by the isolation of (i) antiidiotypic monoclonal antibodies competing with both $\mu$ and $\delta$ ligands but not competing with $\kappa$ ligands (Gramsch, et al. (1988); Coscia, et al. (1991)) and (ii) a monoclonal antibody raised against the purified $\mu$ receptor that interacts with both $\mu$ and $\kappa$ receptors (Bero, et al. (1988)).

Clinical studies suggest a strong relationship between opiates and immune system activity. In humans, narcotic dependence is associated with an increased frequency of infection and decreased immune function. Following opiate administration to animals there is an increase in the morbidity and mortality resulting from microbial infection.

Inflammatory reactions are controlled and amplified by chemotactic peptides that signal the approach of immune cells. Opioid peptides have been documented to be potent in vivo and in vitro stimulants for leukocyte migration (Heagy et al., 1990; Ye et al., 1989; Ruff and Pert, 1987; Saland et al., 1983; Foris et al., 1987). The inventors have shown that opioids including the pentapeptides methionine (MET-ENK) and leucine (LEU-ENK) enkephalin, the polypeptide $\beta$-endorphin ($\beta$-END) and synthetic enkephalin analogs stimulate human lymphocyte migration. When the chemotactic response of highly purified human peripheral blood T cells was titered against enkephalin dose, migration was detectable at concentrations as low as 0.1 pM LEU-ENK. The opiate antagonist naloxone blocked the T cell chemotaxis to MET-ENK, pointing to a classical, naloxone-sensitive pathway. Opioid peptides, like other leukocyte chemoattractants, trigger a number of cellular events including transmembrane signaling and morphological responses. MET-ENK has been reported to enhance T cell aggregation (Kharkevich and Kadagidze, 1989), rosetting to sheep erythrocytes (Wybran et al., 1979), morphological changes including cell flattening and membrane spreading and the activation of adhesion molecules (Wybran et al., 1979; Kharkevich and Kadagidze, 1989). The inventors have shown that cultured human B cells are targets for opiate/opioid effects. Exposing NALM 6 cells (a pre-B acute lymphoblastic leukemia cell line) to MET-ENK results in a rapid rise in the concentration of free intracellular Ca2+ [Ca$^{2+}$]i and the upregulation of CD9 (a B cell adhesion molecule) surface expression.

Studies in animal models, viz. mice, rats and sheep have confirmed that opiates/opioids have marked effects in vivo on both lymphocyte trafficking and recruitment. Interestingly, Stefano et al. have shown that opioid peptides affect the motility of invertebrate amebocytes. These studies demonstrate that opiate effects are not restricted to mammals, suggesting that opioid receptors may have developed quite early in evolutionary history. It is noteworthy that no other cytokine or microbial product has been shown to affect the locomotion of so many distinct kinds of immune cells.

MET-ENK and β-END have been shown to enhance IFN-γ production in cultures of lectin stimulated peripheral blood mononuclear cells (PBMC). In addition these agents have been reported to augment the blastogenic responses of PBMC to both T and B cell lectins. Taub et al. (1991) showed that the humoral response to antigen was diminished in cultures of murine splenocytes incubated with MET-ENK, synthetic enkephalin analogs, or opiates. Conflicting reports have emerged concerning the effects of opioids on lymphoproliferation. Some investigators have reported that lectin-induced proliferation was enhanced by these peptides whereas others have found them to be inhibitory.

Despite numerous studies describing opiate effects on immune cells, their specific role in immune regulation remains highly controversial. Some investigators have reported inhibitory effects, while others document stimulation (reviewed in Sibinga and Goldstein, 1988; Gilmore et al., 1990). Very little is known with certainty about the molecular processes whereby opioids exert their effects. The cumulative evidence suggests that they possess both immunoenhancing and immunoinhibitory potential.

Opiates and synthetic narcotics are used clinically in the management of pain, but their use is limited by a constellation of undesirable side effects, including respiratory depression, miosis, decreased gastrointestinal motility, sedation, nausea and vomiting (Jaffe et al., 1990). A concern of the use of opiates in the treatment of chronic pain is their potential for dependence and abuse. Some studies suggest that the clinical effects of opiates are mediated via a variety of receptors and that the therapeutic effects and the undesirable side effects of opiates are mediated by different receptor (sub)types (Jaffe et al., 1990; Pasternack, 1993). Therefore, it may be possible to separate the therapeutic and side effects of these important opioid/opiate agents with the use of more selective agents for receptor subtypes. The present invention discloses the pharmacological properties of opioid recognition sites and the ability to diagnose selectivity for opiate/opioid receptor ligands.

The δ receptors bind with the greatest affinity to enkephalins and have a more discrete distribution in the brain than either μ or κ receptors, with high concentrations in the basal ganglia and limbic regions. Although morphine interacts principally with μ receptors, peripheral administration of this opioid induces release of enkephalins (Bertolucci, et al. (1992)). Thus, enkephalins may mediate part of the physiological response to morphine, presumably by interacting with δ receptors. Despite pharmacological and physiological heterogeneity, at least some types of opioid receptors inhibit adenylate cyclase, increase K$^+$ conductance, and inactivate Ca$^{2+}$ channels through a pertussis toxin-sensitive mechanism (Puttfarcken, et al. 1988; Attali, et al. 1989; Hsia, et al., 1984). These results and others suggest that opioid receptors belong to the large family of cell surface receptors that signal through G proteins (Di Chiara, et al. (1992); Loh, et al. (1990)).

Many kinds of cell surface receptor/transmembrane systems consist of at least three membrane-bound polypeptide components: (a) a cell-surface receptor; (b) an effector, such as an ion channel or the enzyme adenylate cyclase; and (c) a guanine nucleotide-binding regulatory polypeptide or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeast and man. Nearly all G protein-coupled receptors bear sequence similarities with one another, and it is thought that all share a similar topological motif consisting of seven hydrophobic (and potentially α-helical) segments that span the lipid bilayer (Dohlman et al. 1987; Dohlman et al. 1991). A ligand binding event on the cell surface initiates a series of secondary molecular processes which transduce a signal across the cell membrane. The superfamily of G-protein coupled receptors is also known as R7G.

The G protein regulatory units that associate with membrane receptors consist of three tightly associated subunits, α, β and γ (1:1:1) in order of decreasing mass. Following agonist binding to the receptor, a conformational change is transmitted to the G protein, which causes the Gα-subunit to exchange a bound GDP for GTP and to dissociate from the βγ-subunits. The GTP-bound form of the α-subunit is typically the effector-modulating moiety. Signal amplification results from the ability of a single receptor to activate many G protein molecules, and from the stimulation by Gα-GTP of many catalytic cycles of the effector.

The family of regulatory G proteins comprises a multiplicity of different α-subunits (greater than twenty in man), which associate with a smaller pool of β- and γ-subunits (greater than four each) (Strothman and Simon 1991). Thus, it is anticipated that differences in the α-subunits probably distinguish the various G protein oligomers, although the targeting or function of the various a-subunits might also depend on the β and γ subunits with which they associate (Strothman and Simon 1991).

Improvements in cell culture and in pharmacological methods, and more recently, use of molecular cloning and gene expression techniques, have led to the identification and characterization of many seven-transmembrane segment receptors (i.e., R7G), including new sub-types and sub-sub-types of previously identified receptors. The α$_1$ and α$_2$-adrenergic receptors, once thought to each consist of single receptor species, are now known to each be encoded by at least three distinct genes (Kobilka et al. 1987; Regan et al. 1988; Cotecchia et al. 1988; Lomasney 1990). In addition to rhodopsin in rod cells, which mediates vision in dim light, three highly similar cone pigments mediating color vision have been cloned (Nathans et al. 1986A; and Nathans et al. 1986B). All of the family of G protein-coupled receptors appear to be similar to other members of the family of G protein-coupled receptors (e.g., dopaminergic, muscarinic, serotonergic, tachykinin, etc.), and each appears to share the characteristic seven-transmembrane segment topography.

When comparing the seven-transmembrane segment receptors with one another, a discernible pattern of amino acid sequence conservation is observed. Transmembrane domains are often the most similar, whereas the amino and carboxyl terminal regions and the cytoplasmic loop connecting transmembrane segments V and VI can be quite divergent (Dohlman et al. 1987).

Interaction with cytoplasmic polypeptides, such as kinases and G proteins, probably involves the hydrophobic loops connecting the transmembrane domains of the receptor. The challenge, however, is to determine which features are preserved among the seven-transmembrane segment receptors because of conservation of function, and which divergent features represent structural adaptations to new functions. A number of strategies have been used to test these ideas, including the use of recombinant DNA and gene expression techniques for the construction of substitution and deletion mutants, as well as of hybrid or chimeric receptors (Dohlman et al. 1991).

With the increasing knowledge and discovery of the large number of receptor sub-types, G-protein subunits, and effectors, characterization of ligand binding and G protein recognition properties of these receptors is an important area for investigation. It has long been known that multiple receptors can couple to a single G protein and, as in the case of epinephrine binding to $\beta_2$- and $\alpha_2$-adrenergic receptors, a single ligand can bind to multiple, functionally-distinct, receptor sub-types. Moreover, G proteins with similar receptor and effector coupling specificities have also been identified. For example, three species of human $G_i$ have been cloned (Itoh et al. 1988), and alternate mRNA splicing has been shown to result in multiple variants of $G_s$ (Kozasa et al. 1988). Cloning and over production of the muscarinic and $\alpha_2$-adrenergic receptors led to the demonstration that a single receptor sub-type, when expressed at high levels in the cell, will couple to more than one type of G protein.

Opioid receptors are known to be sensitive to reducing agents, and the occurrence of a disulfide bridge has been postulated as essential for ligand binding (Gioannini, et al. 1989). For rhodopsin, muscarinic, and $\beta$-adrenergic receptors, two conserved cysteine residues in each of the two first extracellular loops have been shown to be critical for stabilizing the functional protein structure and are presumed to do so by forming a disulfide bridge. Structure/function studies of opioid ligands have shown the importance of a protonated amine group for binding to the receptor with high affinity. The binding site of the receptor might, therefore, possess a critical negatively charged counterpart. Catecholamine receptors display in their sequence a conserved aspartate residue that has been shown necessary for binding the positively charged amine group of their ligands.

Given the complexity and apparent degeneracy of function of various opioid receptors, a question of fundamental importance is how, and under what circumstances, do specific sub-type and sub-sub-type receptors exert their physiological effect in the presence of the appropriate stimulatory ligand. A traditional approach to answering this question has been to reconstitute the purified receptor and G protein components in vitro. Unfortunately, purification schemes have been successful for only a very limited number of receptor sub-types and their cognate G-proteins. Alternatively, heterologous expression systems can be of more general usefulness in the characterization of cloned receptors and in elucidating receptor G protein coupling specificity (Marullo et al. 1988; Payette et al. 1990; King et al. 1990).

One such system was recently developed in yeast cells, in which the genes for a mammalian $\beta_2$-adrenergic receptor and $G_s$ $\alpha$-subunit were co-expressed (King et al. 1990). Expression of the $\beta_2$-adrenergic receptor to levels several hundred-fold higher than in any human tissue was attained, and ligand binding was shown to be of the appropriate affinity, specificity, and stereoselectivity. Moreover, a $\beta_2$-adrenergic receptor-mediated activation of the pheromone signal transduction pathway was demonstrated by several criteria, including imposition of growth arrest, morphological changes, and induction of a pheromone-responsive promoter (FUS1) fused to the *Escherichia coli* lacz gene (encoding $\beta$-galactosidase) (King et al. 1990).

Finally, it is important to note, however that expression of a single receptor in the absence of other related sub-types is often impossible to achieve, even in isolated, non-recombinant mammalian cells. Thus, there has been considerable difficulty in applying the standard approaches of classical genetics or even the powerful techniques of molecular biology to the study of opioid receptors. In particular, means are needed for the identification of the DNA sequences encoding individual opioid receptors. Given such isolated, recombinant sequences, it may be possible to address the heretofore intractable problems associated with design and testing of isoform-specific opioid receptor agonists and antagonists. The availability of cDNAS encoding the opioid receptors will permit the detailed study of signal-transduction mechanisms, reveal the anatomical distribution of the mRNAs of these receptors, and provide information on their expression pattern in the nervous and immune systems. This information should ultimately allow better understanding of the opioid system in analgesia, and also the design of more specific therapeutic drugs.

Polynucleotide sequences encoding opioid receptors, and the polypeptide sequences of the encoded receptors, allow the design of pharmaceutical compositions, such as immune system modulators and analgesics, with enhanced specificity of function. In general, the availability of the polypeptide sequences and expression of the proteins will enable efficient screening of candidate therapeutics. The principle in operation through the screening process is straightforward: natural agonists and antagonists bind to cell-surface receptors and activate their physiological effects; certain other molecules bind to these same receptors; therefore, certain other molecules may produce physiological effects and act as therapeutic pharmaceutical agents. Thus, the ability of candidate drugs to bind to opioid receptors can function as an extremely effective screening criterion for the selection of pharmaceutical compositions with a desired functional efficacy.

Prior methods for screening candidate drug compositions based on their ability to preferentially bind to cell-surface receptors has been limited to tissue-based techniques. In these techniques, animal tissues rich in the receptor type of interest are extracted and prepared; candidate drugs are then allowed to interact with the prepared tissue and those found to bind to the receptors are selected for further study. However, these tissue-based screening techniques suffer from several significant disadvantages. First, they are expensive because the source of receptor cell tissue—laboratory animals—is expensive. Second, extensive technical input is required to operate the screens. And, third, the screens may confuse the results because there are no tissues where only a single receptor subtype is expressed exclusively. Such traditional methods lack specificity because they measure a number of interactions; the proper interaction mixed in with a whole variety of unwanted interactions. An additional fundamental deficiency of animal tissue screens is that they contain animal receptors—ideal for the development of drugs for animals but of limited value in human therapeutic agents.

A solution to this problem is provided by the present invention. In of the present invention, polynucleotides encoding opioid receptors are transfected into suitable host cells, that can express polypeptide sequences corresponding to opioid receptors, both in large quantities and through relatively simple laboratory procedures. The result is the availability of extremely specific receptor-drug interactions free from the competitive and unwanted interactions encountered in isolated tissue-based screens. Further expression in a microorganism where no such endogenous receptors exist (e.g. yeast cells or mutant mammalian cell lines) can be useful for screening and evaluating sub-type-selective drugs (Marullo et al. 1988; Payette et al. 1990; and King et al. 1990).

Studies in rodent and large animal models have confirmed the in vivo effects of opioid peptides and alkaloids on leukocyte motility. The administration of MET-ENK or morphine to animals has been shown to enhance lymphocyte trafficking (Shavit et al., 1985; Heagy et al., 1990; Ye et al., 1989; Ruff and Pert, 1987), stimulate transendothelial migration and cause the redistribution of circulating leukocytes (Saland et al., 1983; Fischer, 1988). The injection of β-END or MET-ENK into the cerebroventricles of rodents elicited lymphocyte and macrophage migration into the ventricles (Saland et al., 1983). The direct infusion of MET-ENK into the afferent lymphatics of the popliteal nodes in sheep stimulated small and blast lymphocytes to exit the node and enter the efferent lymph (Moore, 1984). When administered to rabbits the opiate morphine caused a leukocytosis in parallel with a depletion of lymphocyte blasts and other hematopoietic precursors in the bone marrow (Lu et al., 1960).

Many of the molecular details regarding leukocyte motility have yet to be defined. Leukocyte trafficking between lymphoid organs, the circulatory system and tissues is known to be regulated, at least in part, by interaction with endothelial determinants and subendothelial matrix proteins (e.g., laminin, fibronectin and collagen) (Shimizu et al., 1992; Hemler, 1990; Springer, 1990). Several distinct families of leukocyte and endothelial adhesion receptors (e.g., the $\beta_1$ and $\beta_2$ integrins) are thought to facilitate these interactions (Shimizu et al., 1992; Hemler, 1990; Springer, 1990). Many cytokines, growth factors, inflammatory agents, neurogenic peptides and chemotactic factors have been shown to modulate the expression and function of leukocyte and endothelial adhesion molecules (Shimizu et al., 1992; Hemler, 1990; Springer, 1990). Opioid peptides have important immunoregulatory (Sibinga and Goldstein, 1988; Gilmore et al., 1990) as well as potent chemoattractant activity, however little attention has been given to their effects on adhesion molecules.

CD9 is a membrane protein which has recently been shown to have an intriguing role in the regulation of adhesion and cell motility; however, its precise mechanism(s) of function is not understood (Letarte et al., 1993; Forsyth, 1991; Ikeyama et al., 1993; Miyake et al., 1991). Antibody induced activation of CD9 molecules results in an enhancement in the adhesion-dependent functions of a variety of hematopoietic cell types. Following such activation platelets undergo aggregation (Slupsky et al., 1989), endothelial cell monolayers bind a greater number of neutrophils (Forsyth, 1991) and pre-B leukemia cells form homotypic multicellular clusters (Forsyth, 1991). Exposure of certain human lung or gastric adenocarcinomas to an anti-CD9 mAb has been shown to inhibit their phagokinetic (spontaneous) locomotion (Miyake et al., 1991). Studies in which human CD9 cDNA was introduced into cultured tumor cells revealed an inverse correlation between CD9 expression and cell motility; there was a reduction in the locomotion of transformants which expressed high levels (overexpression) of CD9 on their surfaces (Ikeyama et al., 1993). Transfection studies carried out in a murine model system showed that the metastasis of BL-6 (mouse melanoma) transformants expressing high levels of human CD9 was lower than that for the BL-6 parental cells (Ikeyama et al., 1993).

CD9 is a 24-27kDa transmembrane glycoprotein that is expressed on the surface of normal hematopoietic, neural, and endothelial tissues as well as many kinds of leukemias, lymphomas, adenocarcinomas and neuroblastomas (Ikeyama et al., 1993;Rubinstein et al., 1993; Ebener et al., 1990; Komada et al., 1992). CD9 belongs to the novel superfamily of proteins having four transmembrane domains (TM4SF) that includes the C33 antigen; the RA/IA4 membrane protein; two parasite antigens, Sm23 and Sj23; two tumor- associated antigens, ME491/CD63 and C0-029; the pan-leukocyte antigen CD53; the B-lymphocyte-associated antigen CD37; and the target of an antiproliferative antibody, TAPA1 (M38) (Rubinstein et al., 1993; Imai and Yoshie, 1993).

Despite the numerous advances in surgical intervention and the development of aggressive chemotherapies most deaths in cancer patients are caused by metastases. B cell leukemias, neuroblastomas and many other solid tumors are characterized by their high expression of CD9 (Ebener et al., 1990; Komada et al., 1992). Owing to this fact anti-CD9 antibodies are commonly used to deplete human bone marrow of neoplastic cells prior to autologous marrow transplants (Rubinstein et al., 1993). It is noteworthy that most of the leukemias occurring in children are of the pre-B phenotype (CD9$^+$) and relapses occurring in the CNS are a difficult problem (Letarte et al., 1993). It is also of note that in children neuroblastomas (CD9$^+$ neoplasms) are the second most common tumor of the autonomic nervous system and the bone marrow is a frequent site for metastasis (Ebener et al., 1990). The processes involved in the dissemination of tumor cells are not understood. Studies which identify the factors that regulate the motility and adhesion of such abnormal cells may provide insights into the pathology and clinical behavior of metastatic disease.

Using a modern molecular biology approach to identify proteins involved in lymphocyte activation and viral transformation Birkenback et al. (1993) isolated two novel lymphocyte cDNA's. Analysis of these cDNA's suggest that they code for proteins belonging to the R7G superfamily of transmembrane receptors. Unfortunately, the functions of the proteins encoded by these cDNAs were unknown, and therefore, their practiced value only a matter for speculation.

SUMMARY OF THE INVENTION

The inventors have identified a functional opioid-binding site that is expressed in lymphocytes. This receptor is expressed by the major effector cells of the immune system, the lymphocytes. Opiates/opioids exert significant effects on lymphocytes and it is likely that this novel lymphocyte receptor plays an important role in the effects that opiates/opioids exert on immune cells. Unlike neurons, lymphocytes express only low levels of the classical CNS δ, μ and κ type opiate/opioid receptors. Using this novel lymphocyte R7G, termed "EBI1" and the knowledge gained from an investigation of its binding and signaling features one can now isolate other novel cDNAs encoding other members of this R7G family. Further, it is possible to identify the subsets of opioid receptors that are unique to lymphocytes and other immune cells. This information will facilitate the development of specific and valuable therapeutic agents e.g., ones that diminish pain without causing immunosuppression or alternately, ones that block lymphocyte functions without CNS effects.

Opiates/opioids have important immunoregulatory functions. Unfortunately, however the molecular processes underlying these effects are not well understood. The inventors have conducted studies to identify and characterize lymphocyte opioid receptors and their signaling systems. These studies have shown that lymphocyte membranes contain specific recognition sites with high affinity for opiates/opioids. Furthermore, these studies have shown that the lymphocyte receptors are linked with at least two distinct second messenger pathways (i.e., $Ca^{2+}$ and cAMP signaling). Moreover, the inventors have now identified a novel lymphocyte cDNA clone that upon analysis has been found to belong to the R7G superfamily and to have sequences that are homologous to classical opioid receptors. Membranes prepared from COS cells transfected with cDNA encoding the novel lymphocyte R7G exhibit specific, high affinity binding of the δ-selective opiate agonist, DPDPE. Opioid receptor agonists that interact with δ-specific receptors have important immune modulating effects. These studies have characterized this receptor in terms of its ligand binding and signal transducing functions and provided insights into the mechanisms by which opiates/opioids modulate immune functions.

The sequence encoding EBI1 is contained in one of the two cDNAs isolated by Birkenback et al. SEQ ID NO:1, GenBank Accession NO:L08176. The studies of the inventors show that EBI1 is a functional opiate/opioid recognition site that probably plays a major role in mediating the effects that opiate/opioids have on lymphocytes. The inventors have shown that the protein encoded by one of these cDNA's, (referred to by Birkenback et al. as EBI1) is an opioid binding protein that is displayed on the surface of lymphocytes. When EBI1 is expressed in COS cells the transfectants, but not control cells, bind opioid/opiate agonists and antagonists. Following transfection, exposure of COS cells to the endogenous opioid pentapeptide methionine enkephalin (MET-ENK) results in functional activation of the adenylyl cyclase second messenger system. Incubation of the COS cell transfectants with MET-ENK results in an increase in the amount of cAMP produced by the cells. Factors that modulate the levels of cAMP have profound effects on the growth and function of lymphocytes.

There are many implications of the inventors' studies. EBI1 shares many molecular and structural features with the classical neuronal types of opiate/opioid receptors; however, it exhibits a unique nucleotide and amino acid sequence and a distinct pattern of tissue distribution. The available evidence suggests that EBI1 is expressed primarily on lymphocytes. Since its amino acid sequence is different from that of other opiate/opioid binding proteins (i.e., overall ~26–40% amino acid identity with classical opiate/opioid receptors) it is possible to design and synthesize opiate/opioid drugs that bind to EBI1 but not to other types of opiate/opioid receptors, and vice versa. Agents that recognize EBI1 but not other kinds of opiate/opioid binding proteins will exert their effects primarily on immune cells but not in the CNS. This is of great advantage, since agents that serve as agonists to the opioid receptors found in the CNS can have severe side effects that cause them to be of questionable value for the purpose of lymphocyte stimulation. Further, it is possible to make agents that bind selectively to the classical type opiate/opioid receptors expressed on neurons but not to EBI1. Agents that bind to the classical opiate/opioid receptors but not EBI1 act chiefly on neurons. It is now possible to design opioid/opiate drugs that are highly specific for neuroendocrine (e.g., analgesics) functions and ones with selective immunomodulatory activity. Such drugs will bind selectively to neurons or lymphocytes but not to both cell types.

The discovery of the inventors that the EBIL is an opioid binding protein allows for the practice of assays to identify what opioid/opiate agonists and antagonists bind to EBI1 and what other agents bind to the classical type opiate/opioid receptors expressed on nerve cells. These assays allow one to identify opiate agonists/antagonists that bind to the lymphocyte receptors and those that bind to neurons or to both cell types. In this way it is possible to identify agents that act on immune cells and neurons as well as ones that have discrete immunomodulatory or neuroendocrine activity but not both.

The invention anticipates two major approaches for defining opiate/opioid selectivity. The first employs receptor-ligand binding studies to identify the agents that bind to opiate/opioid receptors. The second utilizes functional receptor signaling assays to verify activity.

Receptor-ligand binding studies identify those agents that bind to EBI1 and/or classical type CNS opiate/opioid recognition sites. In these studies, one measures the ligand binding of opiate/opioid agonists and antagonists to the different kinds of opiate/opioid binding proteins. These assays can be done in any of a number of methods known to those of skill. For example, one way to assay receptor-ligand binding is to use cell preparations that only express a single type opiate/opioid receptor. Membranes are prepared from cells transfected with cDNA's encoding (a) EBI1 or (b) classical opiate receptors of the δ, μ, and κ types. In some cases, it will be beneficial to use COS cells and transient expression vectors as well as stable, transformed CHO cell lines that express the proteins. These cells are useful because, in their native state (i.e., without the introduction of foreign cDNA's) neither COS (derived from monkey kidney cells) nor CHO (Chinese hamster ovary) cells have detectable levels of any type opiate/opioid receptor. However, the invention is in no way limited to the CHO cell system, and a variety of systems can be used. For example cultured lymphocytes, monocytes, neuronals, fibroblasts, endodermals and various adrenals and pituitary cells. In addition, bacterial and yeast cells will be used. Expression vectors such as pSG5, pcDNAI/Amp, and pDR2 are contemplated.

Competition assays using tritium-labeled opiate/opioids ($^3$H-DPDPE, $^3$H-DAMGO, $^3$H-U69,593 and $^3$H-diprenorphine) or $^{125}$I-labeled ($^{125}$I-DADLE) allow potentially selective opiate/opioid agents to be evaluated for their ability to compete with the labeled ligands for receptor sites. Typically, labeled ligands are employed at concentrations between 0.1 to 1 nM (i.e., ≤Kd) and the unlabeled test reagents are titered over the range of 0.1 nM to 100 μM, however, these ranges are not meant to be limiting on the invention. Affinity constants can be measured from nonlinear regression analysis of binding curves. These studies identify agents that bind selectively to (a) EBl1, (b) classical opiate/opioid receptors of the δ, μ and/or κ types or (c) EBl1 and CNS receptor types.

A second assay approach utilizes intact cells, for example COS or CHO cells, that express a single variety of opiate/opioid receptor. In these studies the effect that an opiate/opioid agonist or antagonist has on receptor-mediated signaling is identified. The effects of potential agonists and antagonists on the production of cAMP, generation of phosphinositols and calcium transients is measured. To define the effects of potential antagonists on the activation of these signaling systems, one measures the inhibition of responses elicited by agonists, for example MET-ENK, DPDPE, DAMGO, and morphine.

The invention allows one to identify and characterize the lymphocyte opioid receptors and their signaling mechanisms. The inventors have, first, established receptor-ligand binding assays for measuring the type, number and affinity of these lymphocyte receptors (see FIG. 7, FIG. 8, FIG. 9, FIG. 10, FIG. 15, FIG. 11, FIG. 12 and FIG. 13), second, measured the effects of enkephalins and opiate receptor agonists on $[Ca^{2+}]i$, and transmembrane signaling (see FIG. 14, FIG. 15 and FIG. 16, and third, developed flow cytometric assays for the rapid quantitation of opiate/opioids effects (see FIG. 2, FIG. 3, FIG. 4, FIG. 6 and FIG. 7. Using flow cytometric analysis the inventors have measured the direct effects of opioids on the morphology (e.g., shape changes) of lymphocytes and on the reorganization of molecules displayed on the lymphocyte membrane (see FIG. 2, FIG. 3 and FIG. 4).

The inventors have identified two distinct second messenger systems that transduce opioid/opiate signals. It is significant that opiates/opioids are potent lymphocyte chemoattractants, as most other leukocyte chemoattractants (e.g., fMET-LEU-PHE) trigger a transient increase in both $[Ca^{2+}]$ i and cAMP. The inventors find that the application of MET-ENK or synthetic opiate agonists to lymphocytes elicits a rapid rise in cytoplasmic calcium $[Ca^{2+}]$; suggesting activation of the phospholipase (PLC)-phosphoinositide (PI) -diacylglycerol (DAG) $Ca^{2+}$ messenger pathway that may be regulated via $Gq_a$ subunits of the G regulatory proteins.

Opioid stimulation of lymphocytes causes fluctuations of intracellular cAMP. In addition to the classic response of diminishing cAMP levels, the inventors find that under certain conditions MET-ENK enhances cAMP formation in NALM 6 cells. These are important findings, as agents that increase cAMP levels in T and B lymphocytes completely block mitogen-induced proliferation while potentiating lymphocyte differentiation. Factors that increase cAMP also stimulate cell migration and/or promote the expression of lymphocyte differentiation antigens (e.g.,IL-2 receptors, MHC antigens) and adhesion molecules (e.g., LFA-1). Such enhancements in cAMP are thought to be initiated by ligand-induced receptor coupling to $G_s\alpha$ subunits of regulatory G proteins. On the other hand receptor-mediated decreases in cAMP are thought to be regulated via $G_i\alpha$ subunits of regulatory G proteins. These studies show, therefore, that lymphocyte opioid receptors activate at least two distinct signaling pathways (i.e., the PLC-PI-DAG-$Ca^{2+}$ system and the PKA-cAMP system). These results may begin to provide insights into the mechanisms underlying the immuno-stimulatory and inhibitory effects of opiates/opioids.

Generally, the present invention concerns the identification of opioid receptors. Once identified, these polypeptides have a variety of utility, with one of the most important being the ability to serve as the basis for screening assays that allow for the determination of substances that can be used as opioid receptor agonists and antagonists. Such agonists and antagonists have pharmaceutical utility. There is a great need for new opioid receptor agonists and antagonists, since those currently used have rather severe side-effects. Further, since the inventors have shown that one type opioid binding protein occurs exclusively or predominately in immune cells, while other opioid receptors are known to occur predominately in CNS cells, it is possible to screen for agonists and antagonists that act exclusively or predominately in either the immune system or CNS.

The definition of an immune cell-specific lymphocyte receptor includes those receptors that are expressed predominately on immune cells, as opposed to predominately on the cells of the nervous system. This definition does not exclude receptors that may be expressed at a low level on non-immune cells, including neurons. For example, it is possible that an immune cell-specific lymphocyte receptor such a EBI1 will have some expression in neurons, however, it is predominately expressed in immune cells. By definition, a lymphocyte opioid receptor is a lymphocyte protein with high affinity for opiate receptor agonists and antagonists under appropriate conditions.

By definition, classical neuronal (CNS) type opiate/opioid receptors are expressed at very low levels on lymphocytes. These can only be detected using sensitive PCR methods that amplify transcripts expressed at extremely low copy number. The neuronal type opioid receptor can be, for example, a κ, μ, or δ opioid receptor. Such neuronal type receptors are expressed predominantly in the CNS although they may also be present in other cell types, for example in immune cells.

The present invention contemplates a process of screening substances for their ability to interact with an opiate/opioid recognition site, and testing the ability of selected substances to interact with the opioid receptor proteins. These opioid receptor proteins are often lymphocyte receptors that bind an opiate/opioid under appropriate conditions. In a preferred embodiment, the lymphocyte opiate/opioid recognition site is an EBI1 polypeptide. Following transfection into COS cells activation with opiate receptor agonists results in the modulation of cAMP. Within the immune system, there are several types of cells. Lymphocytes regulate all aspects of immune function. T cells are crucial for the cellular response to antigens and provide help for B-cells. B-cells make antibodies and are essential for the humoral arm of the immune response. EBI1 is expressed on both T and B lymphocytes. The nucleotide sequence of a cDNA encoding EBI1 was diagnosed by others, and is found in SEQ ID NO:1. The amino acid sequence of EBI1 is found in SEQ ID NO:2.

According to long-standing patent law convention, where they appear in this specification, including the claims, the words "a" and "an" denote "one or more."

A primary aspect of this invention is a process of screening an opiate/opioid substance for its ability to interact with a lymphocyte receptor that binds an opiate/opioid under appropriate conditions. Such processes involve, first, providing an lymphocyte receptor polypeptide, and, second, testing the ability of the substance to interact with the lymphocyte receptor. In some embodiments, the lymphocyte receptor is EBI1. In some cases, the EBI1 lymphocyte receptor will have an amino acid sequence as contained in SEQ ID NO:2. A preferred manner of practicing the screening process involves transfecting a host cell with a polynucleotide that encodes a lymphocyte receptor that binds opiate/opioid under appropriate conditions to form a transformed cell and maintaining the transformed cell under biological conditions sufficient for expression of the lymphocyte receptor polypeptide. The polynucleotide may encode a lymphocyte opioid binding protein polypeptide that has an amino acid sequence of SEQ ID NO:2. For example, the polynucleotide that encodes a lymphocyte receptor polypeptide that binds opiates/opioids can have a nucleotide sequence such as that contained in SEQ ID NO:1.

Processes for assaying the ability of a substance for the ability to bind an opiate/opioid are well-described in the Examples.

The process described above can be adapted to screen for substances with the ability to interact with an immune cell-specific receptor which has the following steps. First, one provides an immune cell-specific lymphocyte receptor polypeptide. Then, one obtains a candidate immune cell-specific lymphocyte receptor agonist or antagonist and tests its ability to interact with the immune cell-specific lymphocyte receptor. Finally, one may provide a product that comprises the agonist or antagonist and has the ability to interact with the immune cell-specific lymphocyte receptor. The immune cell-specific lymphocyte receptor polypeptide may be an EBIL polypeptide, for example, it may have an amino acid sequence contained in SEQ ID NO:2. The immune cell-specific lymphocyte receptor polypeptide comprises transfection of a host cell may be provided by introduction of a polynucleotide that encodes an immune cell-specific lymphocyte receptor polypeptide into a cell to form a transformed cell and maintaining said transformed cell under biological conditions sufficient for expression of said receptor polypeptide.

A specialized subset of the above described-processes includes processes of screening substances for the ability to interact with an immune cell-specific lymphocyte receptor but not with a neuronal type opioid receptor. These processes involve the following steps. First, one provides an immune cell-specific lymphocyte receptor polypeptide that binds opiates/opioids. Then, a candidate substance is tested for ability to interact with the lymphocyte receptor. Next, one provides a neuronal type opioid receptor polypeptide. Finally, the candidate substance is tested for ability to interact with the neuronal type receptors. One can then determine which candidate substances interact with immune cell-specific lymphocyte receptors but not with neuronal type receptors. The immune cell-specific lymphocyte receptor polypeptide is the EBIL receptor polypeptide in certain preferred embodiments of the invention. The lymphocyte receptor polypeptide can have an amino acid sequence contained in SEQ ID NO:2. In some preferred aspects, the immune cell-specific lymphocyte receptor polypeptide is provided by transfecting a host cell with a polynucleotide that encodes a lymphocyte receptor polypeptide to form a transformed cell and maintaining the transformed cell under biological conditions sufficient for expression of the receptor polypeptide. The polynucleotide that encodes a lymphocyte receptor polypeptide may encode an amino acid sequence contained in SEQ ID NO:2. Further, the polynucleotide that encodes a lymphocyte receptor polypeptide may have a nucleotide sequence of SEQ ID NO:1. As with the lymphocyte receptor, the neuronal type opioid receptor polypeptide can be provided by transfecting a host cell with a polynucleotide that encodes a neuronal type opioid receptor polypeptide to form a transformed cell and maintaining the transformed cell under biological conditions sufficient for expression of the neuronal type opioid receptor polypeptide. In certain preferred embodiments, the polynucleotide encoding the neuronal opioid receptor encodes a κ, μ, or δ opioid receptor.

Other aspects of the invention involve substances with an ability to interact with a lymphocyte receptor that binds an opiate/opioid under appropriate conditions. Such substances are isolatable by a process comprising the following steps. First, one provides a lymphocyte receptor polypeptide. Then, one tests the ability of the substance to interact with the lymphocyte receptor polypeptide. Methods of determining this interaction are well-described in the Examples. The substance can be an agonist or antagonist of the lymphocyte receptor.

Substances of the nature described above can be placed in pharmacological compositions for administration to humans and other animals. Such pharmaceutical compositions comprise a physiologically acceptable carrier and a substance with the ability to interact with a lymphocyte receptor.

Methods of interacting a lymphocyte receptor with a substance with an ability to interact with a lymphocyte receptor form another aspect of the invention. These methods involve contacting substances isolatable as described above with a lymphocyte receptor. In some preferred aspects, the lymphocyte receptor is contained in an animal, for example, a human.

The invention encompasses processes of making a product with an ability to interact with a lymphocyte receptor that binds an opiate/opioid under appropriate conditions. Such processes have the following steps. First, one provides a lymphocyte receptor polypeptide that binds an opiate/opioid under appropriate conditions. Then, one obtains a candidate lymphocyte receptor agonist or antagonist. The candidate substance is then tested for the ability of the candidate to act as an agonist or antagonist of the lymphocyte receptor. Finally, one provides a product that comprises the agonist or antagonist and has the ability to interact with the lymphocyte receptor. The lymphocyte receptor may be any described above. For example, the lymphocyte receptor polypeptide may have an amino acid sequence contained in SEQ ID NO:2.

The application also encompasses products with an ability to interact with a lymphocyte receptor that binds an opiate/opioid under appropriate condition. Such products are isolatable by a process having the following steps. First, one provides a lymphocyte receptor polypeptide and obtains a candidate lymphocyte receptor agonist or antagonist. Then, one tests the ability of the candidate agonist or antagonist to interact with the lymphocyte receptor. Finally, one provides a product that comprises the agonist or antagonist and has the ability to interact with the lymphocyte receptor. The product can be either an agonist or antagonist of the lymphocyte receptor. The invention contemplates a pharmaceutical composition comprising a physiologically acceptable carrier and a substance with an ability to interact with a lymphocyte receptor that binds an opiate/opioid under appropriate conditions, the substance isolatable by the process described above. A product with an ability to interact with an immune cell-specific lymphocyte receptor is encompassed with in the invention.

The invention contemplates methods of interacting a lymphocyte receptor that binds an opiate/opioid under appropriate conditions with a substance with an ability to interact with a lymphocyte receptor. The substance is isolatable by the process described above, wherein one: provides a lymphocyte receptor and a substance with an ability to interact with a lymphocyte receptor, and contacting the lymphocyte receptor with the substance. The lymphocyte receptor can be contained in an animal, for example, a human.

The methods described above may be used to isolate substances with an ability to interact with an immune cell-specific lymphocyte receptor. This process involves providing an immune cell-specific lymphocyte receptor polypeptide and testing the ability of the substance to interact with the receptor. The substance can be an agonist of an immune cell-specific lymphocyte receptor. Alternatively, the substance may be an antagonist of an immune cell-specific receptor. These methods allow the practice of a process of making a product with an ability to interact with an immune cell-specific receptor. This process involves providing an immune cell-specific lymphocyte receptor polypeptide; obtaining a candidate immune cell-specific lymphocyte receptor agonist or antagonist; testing the ability of the candidate immune cell-specific lymphocyte receptor agonist or antagonist to interact with the immune cell-specific lymphocyte receptor; and providing a product that comprises the agonist or antagonist and has the ability to interact with the immune cell-specific lymphocyte receptor. The immune cell-specific lymphocyte receptor polypeptide can be an EBI1 polypeptide, for example, one with an amino acid sequence contained in SEQ ID NO:2.

The invention contemplates substances with an ability to interact with a immune cell-specific lymphocyte receptor but not in neuronal type opioid receptor. These substances are isolatable by a process comprising the steps of: providing an immune cell-specific lymphocyte receptor polypeptide; testing the ability of the substance to interact with the immune cell-specific lymphocyte receptor; providing a neuronal type opioid receptor polypeptide; and testing the ability of the substance to interact with the neuronal type opioid receptor. The substance may be either an agonist or antagonist of the lymphocyte receptor.

Processes of making a product with an ability to interact with an immune cell-specific lymphocyte receptor but not a neuronal type receptor are also within the scope of the invention. Such processes comprise the steps of: obtaining a candidate lymphocyte receptor agonist or antagonist; providing an immune cell-specific lymphocyte receptor polypeptide; testing the ability of the candidate immune cell-specific lymphocyte receptor agonist or antagonist to interact with the immune cell-specific lymphocyte receptor; providing a neuronal type opioid receptor polypeptide; testing the ability of the candidate immune cell-specific lymphocyte receptor agonist or antagonist to interact with the neuronal type opioid receptor; and providing a product that comprises the agonist or antagonist and has the ability to interact with the immune cell-specific lymphocyte receptor, but not the neuronal type opioid receptor. This process can be practiced when the immune cell-specific lymphocyte receptor polypeptide is an EBIL polypeptide. Further, the immune cell-specific lymphocyte polypeptide can have an amino acid sequence contained in SEQ ID NO:2. The immune cell-specific lymphocyte receptor polypeptide can be provided by transfecting a host cell with a polynucleotide that encodes an immune cell-specific lymphocyte receptor polypeptide to form a transformed cell and maintaining the transformed cell under biological conditions sufficient for expression of the lymphocyte receptor polypeptide. The polynucleotide can encodes lymphocyte receptor polypeptide that has an amino acid sequence contained in SEQ ID NO:2. Further, the polynucleotide that encodes a lymphocyte receptor polypeptide may have a nucleotide sequence of SEQ ID NO:1. The neuronal type receptor can be a κ, μ, or δ opioid receptor and can be provided by transfecting a host cell with a polynucleotide that encodes a non-immune cell-specific lymphocyte receptor polypeptide to form a transformed cell and maintaining the transformed cell under biological conditions sufficient for expression of the lymphocyte receptor polypeptide.

The invention contemplates products with an ability to interact with an immune cell-specific lymphocyte receptor but not a neuronal type opioid receptor isolatable by a process comprising the steps of: obtaining a candidate immune cell-specific lymphocyte receptor agonist or antagonist; providing an immune cell-specific lymphocyte receptor polypeptide; testing the ability of the candidate immune cell-specific lymphocyte receptor agonist or antagonist to interact with the lymphocyte receptor; providing a neuronal type receptor polypeptide; testing the ability of the candidate immune cell-specific lymphocyte receptor agonist or antagonist to interact with the neuronal type receptor; and providing a product that comprises the agonist or antagonist and has the ability to interact with the immune cell-specific lymphocyte receptor, but not the neuronal type receptor. The product can be an agonist or antagonist of a lymphocyte receptor.

The invention contemplates methods of conferring opioid binding specificity to a cell. Such methods comprising the steps of: obtaining a polynucleotide that encodes a lymphocyte receptor that binds an opiate/opioid under appropriate conditions; transfecting a host cell with the polynucleotide to form a recombinant cell; and culturing the recombinant cell under appropriate conditions to express the encoded lymphocyte receptor. These methods may comprise the further step of testing the recombinant cell to determine whether the cell will bind an opiate/opioid. This testing may involve testing for opiate/opioid binding specificity or binding an opiate/opioid, or analog thereof to the cell.

The invention contemplates a method of screening for genes encoding lymphocyte receptors having opioid/opiate binding. These methods comprise steps as follows. First, an appropriate nucleic acid library is prepared according to any of a number of methods known to those of skill in the art. Then, a hybridization probe that is based on a portion the nucleic acid sequence of the EBIL gene is used to probe the library and pull out potential clones. These clones may then be analyzed to determine whether or not they code for lymphocyte receptors.

BRIEF DESCRIPTION OF THE DRAWINGS

FIG. 3, Panels A-D. Methionine-enkephalin causes a discrete, transient up-regulation in the CD9 molecules expressed on NALM 6 cells. NALM 6 cells ($10^6$/ml) were incubated at 37° with MET-ENK ($10^{-7}$M) for 0 (Panel A and B) or 30 minutes (Panel C and D). Cells were then transferred to an ice bath, pelleted by centrifugation, and stained for immunofluorescent analysis and flow cytoflourimetry. Data are shown as histograms depicting the distribution of 10,000 cells labeled with anti-CD9 (Panel A and C) or CD-10 (Panel B and D) mAb. The anti-CD9 and anti-CD10 mAb used for these experiments were isotype matched (IgG1).

$$[Ca^{2+}]_i = (Kd) \cdot \frac{(R - R_{min}) \cdot Sf2}{(R_{max} - R) \cdot Sb2}$$

$R_{max}$ values were determined by measuring the maximum shift in indo violet/blue fluorescence for cells treated with 4 μM ionomycin. Rmin was measured as the minimum ratio for the violet blue fluorescence of ionomycin treated cells following the addition of 8 mM EGTA. The values for (Sf2/Sb2) were determined by spectrofluorometry and were found to be between the range of 2.0 to 2.5. The Kd (effective dissociation constant) was set at 250 nM. Panel A, Dose-dependent effects of MET-ENK (Note: Inset shows the direct relationship between the onset of the response and MET-ENK dose). Panel B, Naloxone inhibition of the MET-ENK stimulated [$Ca^{2+}$]$_i$ response. Panel C, B4 monoclonal antibody (anti-CD19) stimulation of [$Ca^{2+}$]$_i$ in the presence and absence of naloxone.

Figure 16:
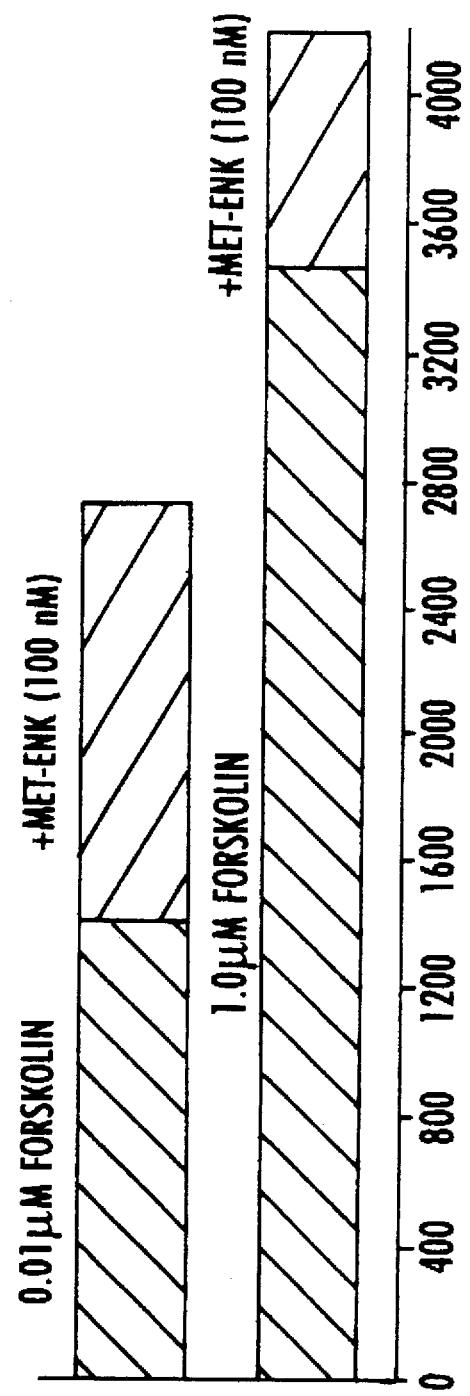

FIG. 16. Methionine-enkephalin potentiates cAMP accumulation in forskolin-activated NALM 6 cells. NALM 6 cells (2×10$^6$/ml) were stimulated with forskolin or forskolin+MET-ENK at the concentrations indicated and in the presence of 1 mM isobutyl-1-methylxanthine. Cyclic AMP was assayed after 15 minutes at 37° C. Data are expressed as fmoles of cAMP/minute. Samples were processed as previously described Cobb, Heagy, Dunner et al., 1980; cAMP was measured using a commercial RIA kit.

FIG. 17. Deduced partial amino acid sequences in second transmembrane regions of some opiate/opioid receptors. LOR=SEQ ID NO:3, ROR-C=SEQ ID NO:4, ROR-δ=SEQ ID NO:5, ROR-μ=SEQ ID NO:6, ROR-κ=SEQ ID NO:7, and nORL1=SEQ ID NO:8.

Figure 18:
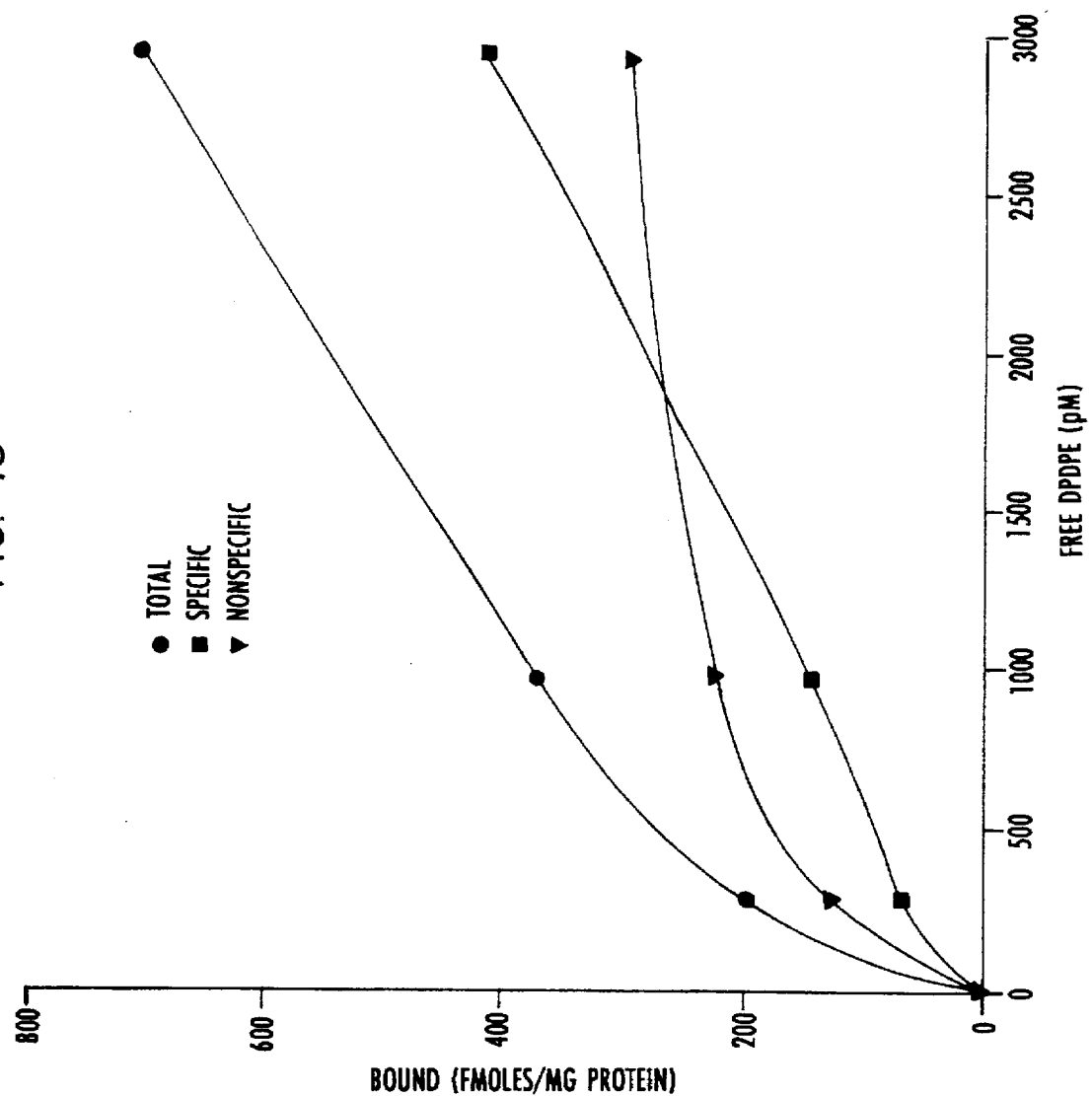

FIG. 18. The delta opiate receptor agonist DPDPE binds to cell membranes prepared from COS cells transfected with cDNA encoding the novel lymphocyte R7G. Data are plotted as the concentration of free $^3$H-DPDPE (x-axis) vs specific binding of $^3$H-DPDPE (y-axis). Duplicate samples of membrane were incubated at 20° C. in 1 mM tris HCl, pH 7.8, 100 mM phenylmethylsulfonate and 0.32M sucrose for 0.5 h with $^3$H-DPDPE (0.1–30 nM), or with $^3$H-DPDPE and 50 μM unlabeled naloxone. Specific binding was determined as the difference between the total and nonspecific binding measured for samples incubated with 50 μM unlabeled naloxone. Assays were carried out in 96-well polypropylene microtiter plates (Costar Corporation; Cambridge, Mass.). Following incubation, the cells were transferred to Whatman GF glass fiber filters, washed with three 3-ml portions of binding assay buffer, dried and then counted in a liquid scintillant.

DETAILED DESCRIPTION OF SPECIFIC EMBODIMENTS

Detailed Description of the Invention

I. Screening Assays

The present invention contemplates a process of screening substances for their ability to interact with opioid binding proteins (comprising the steps of providing opioid binding proteins) and testing the ability of selected substances to interact with opioid binding proteins.

Utilizing the methods and compositions of the present invention, screening assays for the testing of candidate substances such as agonists and antagonists of opioid receptors can be derived. A candidate substance is a substance which potentially can interact with or modulate, by binding or other intramolecular interaction, an opioid receptor polypeptide. In some instances, such a candidate substance will be an agonist of the receptor and in other instances can exhibit antagonistic attributes when interacting with the receptor polypeptide. In other instances, such substances can have mixed agonistic and antagonistic properties or can modulate the opioid receptor in other ways.

Recombinant receptor expression systems of the present invention possess definite advantages over tissue-based systems. The methods of the present invention make it possible to produce large quantities of opioid receptors for use in screening assays. More important, however, is the relative purity of the receptor polypeptides provided by the present invention. A relatively pure polypeptide preparation for assaying a protein agonist and/or antagonist interaction makes it possible to use elutive methods without invoking competing, and unwanted, side-reactions.

Cloned expression systems such as those of the present invention are also useful where there is difficulty in obtaining tissue that satisfactorily expresses a particular receptor. Cost is another very real advantage, at least with regard to the microbial expression systems of the present invention. For antagonists in a primary screen, microorganism expression systems of the present invention are inexpensive in comparison to prior art tissue-screening methods.

Traditionally, screening assays employed the use of crude receptor preparations. Typically, animal tissue slices thought to be rich in the receptor of interest was the source of the receptor. Alternatively, investigators homogenized the tissue and used the crude homogenate as a receptor source. A major difficulty with this approach is that there are no tissue types where only one receptor type is expressed. The data obtained therefore could not be definitively correlated with a particular receptor. With the recent cloning of receptor sub-types and sub-sub-types, this difficulty is highlighted. A second fundamental difficulty with the traditional approach is the unavailability of human tissue for screening potential drugs. The traditional approach almost invariably utilized animal receptors. With the cloning of human receptors, there is a need for screening assays which utilize human receptors.

With the availability of cloned receptors, recombinant receptor screening systems have several advantages over tissue based systems. A major advantage is that the investigator can now control the type of receptor that is utilized in a screening assay. Specific receptor sub-types and sub-sub-types can be preferentially expressed and its interaction with a ligand can be identified. Other advantages include the availability of large amounts of receptor, the availability of rare receptors previously unavailable in tissue samples, and the lack of expenses associated with the maintenance of live animals.

Screening assays of the present invention generally involve determining the ability of a candidate substance to bind to the receptor and to affect the activity of the receptor, such as the screening of candidate substances to identify those that inhibit or otherwise modify the receptor's function. Typically, this method includes preparing recombinant receptor polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect human receptors, and thus can be suitable for use in humans.

As is well known in the art, a screening assay provides a receptor under conditions suitable for the binding of an agent to the receptor. These conditions include but are not limited to pH, temperature, tonicity, the presence of relevant co-factors, and relevant modifications to the polypeptide such as glycosylation or prenylation. It is contemplated that the receptor can be expressed and utilized in a prokaryotic or eukaryotic cell. The host cell expressing the receptor can be used whole or the receptor can be processed, partially purified or fully isolated from the host cell. The receptor can be membrane bound, integrated the membrane of the host cell or free in the cytosol of the host cell. The host cell can also be fractionated into sub-cellular fractions where the receptor can be found. For example, cells expressing the receptor can be fractionated into the nuclei, or the cytosolic fractions and the endoplasmic reticulum, vesicles, or the membrane surfaces of the cell isolated.

Conditions needed for receptor function are well known in the art. pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of co-factors can be required for the proper functioning of the receptor. Typical co-factors include sodium, potassium, calcium, magnesium, and chloride. In addition, small, non-peptide molecules, known as prosthetic groups can be required.

It is well known in the art that proteins can be reconstituted in artificial membranes, vesicles or liposomes. (Danboldt, et al. 1990). The present invention contemplates that the receptor can be incorporated into artificial membranes, vesicles or liposomes. The reconstituted receptor can be utilized in screening assays.

It is further contemplated that the receptor of the present invention can be coupled to a solid support. The solid support can be agarose beads, polyacrylamide beads, poly-acrylic beads or other solid matrices including ELISA and culture plates capable of being coupled to proteins. Well known coupling agents include cyanogen bromide, carbonyldiimidazole, tosyl chloride, and glutaraldehyde.

It is further contemplated that secondary polypeptides which can function in conjunction with the receptor of the present invention can be provided. For example, the receptor of the present invention exerts its physiological effects in conjunction with G-proteins and an effector polypeptide.

In a typical screening assay for identifying candidate substances, one employs the same recombinant expression host as the starting source for obtaining the receptor polypeptide, generally prepared in the form of a crude homogenate. Recombinant cells expressing the receptor are washed and homogenized to prepare a crude polypeptide homogenate in a desirable buffer such as disclosed herein. In a typical assay, an amount of polypeptide from the cell homogenate, is placed into a small volume of an appropriate assay buffer at an appropriate pH. Candidate substances, such as agonists and antagonists, are added to the admixture in convenient concentrations and the interaction between the candidate substance and the receptor polypeptide is monitored.

Where one uses an appropriate known substrate for the receptor, one can, in the foregoing manner, obtain a baseline activity for the recombinantly produced receptor. Then, to test for inhibitors or modifiers of the receptor function, one can incorporate into the admixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of opioid receptor polypeptides in one or more manners.

In one embodiment, such an assay is designed to be capable of discriminating those candidate substances with desirable therapeutic properties but which lack undesirable properties (e.g. respiratory depression, addiction) of opioids. Also possible are studies that identify the molecular properties underlying the ability of agents to bind to and activate the receptors. In another embodiment, screening assays for testing candidate substances such as agonists and antagonists of opioid receptors are used to identify such candidate substances having selective ability to interact with one or more of the opioid receptor polypeptides but are without a substantially overlapping activity with other of the opioid receptor polypeptides identified herein.

Additionally, screening assays for the testing of candidate substances are designed to allow the investigation of structure activity relationships of opiate/opioids with the receptors, e.g., study of binding of naturally occurring hormones or other substances capable of interacting or otherwise modulating with the receptor versus studies of the activity caused by the binding of such molecules to the receptor. In certain embodiments, the polypeptides of the invention are crystallized in order to carry out x-ray crystallographic studies as a means of evaluating interactions with candidate substances or other molecules with the opioid receptor polypeptide. For instance, the purified recombinant polypeptides of the invention, when crystallized in a suitable form, are amenable to detection of intra-molecular interactions by x-ray crystallography.

An important aspect of the invention is the use of recombinantly produced opioid receptor polypeptides in screening assays for the identification of substances which can inhibit or otherwise modify or alter the function of opiate/opioid receptors. The use of recombinantly produced receptors is of particular benefit because the naturally occurring receptor is present in only small quantities and has proven difficult to purify. Moreover, this provides a ready source of receptor, which has heretofore been unavailable.

As described above, receptors in the presence of agonists exert their physiological effects through a secondary molecule. A screening assay of the invention, in preferred embodiments, conveniently employs an opioid receptor polypeptide directly from the recombinant host in which it is produced. This is achieved most preferably by simply expressing the selected polypeptide within the recombinant host, typically a eukaryotic host, followed by preparing a crude homogenate which includes the enzyme's activity. A portion of the crude homogenate is then admixed with an appropriate effector of the receptor along with the candidate substance to be tested. By comparing the binding of the selected effector to the receptor in the presence or absence of the candidate substance, one can obtain information regarding the physiological properties of the candidate substance.

The receptor can be expressed in a prokaryotic or a eukaryotic cell. Receptors have been expressed in *E. coli* (Bertin, et al. 1992), in yeast (King, et al. (1990) and in mammalian cells (Bouvier, et. al. 1988).

A cell expressing a receptor can be used whole to screen agents. For example, cells expressing the receptor of the present invention can be exposed to radiolabeled agent and the amount of binding of the radiolabeled agent to the cell can be determined.

The cell expressing the receptor can be fractionated into sub-cellular components which contain the receptor of the present invention. Methods for purifying sub-cellular fractions are well known in the art. Sub-cellular fractions include but are not limited to the cytoplasm, cellular membrane, other membranous fractions such as the endoplasmic reticulum, golgi bodies, vesicles and the nucleus. Receptors isolated as sub-cellular fractions can be associated with cellular membranes. For example, if cellular membrane vesicles are isolated from the cell expressing the receptor, the receptor molecule can be membrane bound. It is further contemplated that the receptor of the present invention can be purified from a cell that expresses the receptor. Methods of purification are well known in the art. The purified receptor can be used in screening assays.

In that most such screening assays in accordance with the invention are designed to identify agents useful in mimicking the desirable aspects of opioids while eliminating the undesirable aspects of the hormone, preferred assays employ opioids as the normal agonist.

There are believed to be a wide variety of embodiments which can be employed to determine the effect of the candidate substance on the receptor polypeptides of the invention, and the invention is not intended to be limited to any one such method. However, it is generally desirable to employ a system wherein one can measure the ability of the receptor polypeptide to bind to and or be modified by the effector employed in the presence of a particular substance.

The detection of an interaction between an agent and a receptor can be accomplished through techniques well known in the art. These techniques include but are not limited to centrifugation, chromatography, electrophoresis and spectroscopy. The use of isotopically labelled reagents in conjunction with these techniques or alone is also contemplated. Commonly used radioactive isotopes include $^{3}H$, $^{14}C$, $^{22}Na$, $^{32}P$, $^{35}S$, $^{45}Ca$, $^{60}Co$, $^{125}I$, and $^{131}I$. Commonly used stable isotopes include $^{2}H$, $^{13}C$, $^{15}N$, $^{18}O$.

For example, if an agent can bind to the receptor of the present invention, the binding can be detected by using radiolabeled agent or radiolabeled receptor. Briefly, if radiolabeled agent or radiolabeled receptor is utilized, the agent-receptor complex can be detected by liquid scintillation or by exposure to X-Ray film.

When an agent modifies the receptor, the modified receptor can be detected by differences in mobility between the modified receptor and the unmodified receptor through the use of chromatography, electrophoresis or centrifugation. When the technique utilized is centrifugation, the differences in mobility is known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, if an agent covalently modifies a receptor, the spectroscopic differences between modified and unmodified receptor in the nuclear magnetic resonance (NMR) spectra can be detected. Alternatively, one can focus on the agent and detect the differences in the spectroscopic properties or the difference in mobility between the free agent and the agent after modification of the receptor.

When a secondary polypeptide is provided, the agent-receptor-secondary polypeptide complex or the receptor-secondary polypeptide complex can be detected. Differences in mobility or differences in spectroscopic properties as described above can be detected.

It is further contemplated that when a secondary polypeptide is provided the enzymatic activity of the effector polypeptide can be detected. For example, many receptors exert physiological effects through the stimulation or inhibition of adenylyl cyclase. The enzymatic activity of adenylyl cyclase in the presence of an agent can be detected.

The interaction of an agent and a receptor can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/receptor complex so produced. Then, one simply measures the amount of each (e.g., versus a control to which no candidate substance has been added). This measurement can be made at various time points where velocity data is desired. From this, one can determine the ability of the candidate substance to alter or modify the function of the receptor.

Numerous techniques are known for separating the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

The effector/receptor complex itself can also be the subject of techniques such as x-ray crystallography. Where a candidate substance replaces the opioid molecule as the drug's mode of action, studies designed to monitor the replacement and its effect on the receptor will be of particular benefit.

A. Screening For Agonists and Antagonists

Development of highly selective, clinically useful opioid receptor and binding protein agonists will be facilitated by understanding the specific sites within the delta receptor necessary for agonist binding. The cloning of the mouse delta opioid receptor CDNA has opened up the possibility to investigate the structural domains of this receptor subtype that are responsible for its functioning. Functional differences between the opioid receptors are known, for example, a single amino acid in the second transmembrane spanning region of the delta receptor is critical for the binding of delta-selective opioid agonists. This goal relies on expression or the use of receptor proteins and agonists/antagonists. There are three phases of the elucidation of agonists and antagonists: (1) binding assays to determine whether a candidate binds the peptide, (2) competitive binding studies to determine binding affinity and location, (3) receptor-ligand interaction studies.

B. Screening assays for opioid receptor polypeptides.

The present invention provides a process of screening a biological sample for the presence of an opioid receptor polypeptide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the opioid receptor polypeptide whose presence is being assayed. Typically, exposure is accomplished by forming an admixture in a liquid medium that contains both the antibody and the candidate opioid receptor polypeptide. Either the antibody or the sample with the opioid receptor polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the opioid receptor polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$M, exposure time is from about 10 minutes to about 200 minutes.

The presence of opioid receptor polypeptide in the sample is detected by detecting the formation and presence of antibody-opioid receptor polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

C. Screening assay for anti-opioid receptor antibody.

In another aspect, the present invention provides a process of screening a biological sample for the presence of antibodies immunoreactive with an opioid receptor polypeptide (i.e., an anti-opioid receptor antibody). In accordance with such a process, a biological sample is exposed to an opioid receptor polypeptide under biological conditions and for a period of time sufficient for antibody-polypeptide conjugate formation and the formed conjugates are detected.

D. Screening assay for polynucleotide that encodes an opioid receptor polypeptide.

A DNA molecule and, particularly a probe molecule, can be used for hybridizing as oligonucleotide probes to a DNA source suspected of possessing an opioid receptor polypeptide encoding polynucleotide or gene. The probing is usually accomplished by hybridizing the oligonucleotide to a DNA source suspected of possessing such a receptor gene. In some cases, the probes constitute only a single probe, and in others, the probes constitute a collection of probes based on a certain amino acid sequence or sequences of the opioid receptor polypeptide and account in their diversity for the redundancy inherent in the genetic code.

A suitable source of DNA for probing in this manner is capable of expressing opioid receptor polypeptides and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the opioid receptor family and related polypeptides from a DNA library potentially containing such sequences; (3) primers for hybridizing to related sequences for the purpose of amplifying those sequences; (4) primers for altering the native opioid receptor DNA sequences; as well as other techniques which rely on the similarity of the DNA sequences to those of the opioid receptor DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected opioid receptor gene. In these aspects, nucleic acid probes of an appropriate length are prepared based on a consideration of the selected opioid receptor sequence. The ability of such nucleic acid probes to specifically hybridize to opioid receptor encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of the opioid receptor encoding sequence. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,603,102, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate opioid receptor coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

II. Polynucleotides

A. Isolated and purified polynucleotide that encode opioid receptor polypeptides.

In one aspect, the present invention involves isolated and purified polynucleotides that encode opioid receptor polypeptides. In a preferred embodiment, the polynucleotide of the present invention is a DNA molecule. As used herein, the term "polynucleotide" means a sequence of nucleotides connected by phosphodiester linkages. Polynucleotides are presented herein in the direction from the 5' to the 3' direction. A polynucleotide of the present invention can comprise from about 680 to about several hundred thousand base pairs. Preferably, a polynucleotide comprises from about 680 to about 150,000 base pairs. A polynucleotide can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

Polynucleotides of the present invention can be prepared using standard techniques well known to one of skill in the art. The preparation of a CDNA molecule encoding an opioid receptor polypeptide of the present invention is described hereinafter in Examples 1 and 2. A polynucleotide can also be prepared from genomic DNA libraries using lambda phage technologies.

III. Opioid Receptor Polypeptide

In one embodiment, the present invention contemplates the use of an isolated and purified opioid receptor polypeptide. Preferably, an opioid receptor polypeptide used in the invention is a recombinant polypeptide. Most preferably, the polypeptide is EBI1.

Polypeptides are disclosed herein as amino acid residue sequences. Those sequences are written left to right in the direction from the amino to the carboxyl terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like opioid receptor characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte & Doolittle, *J. Mol. Biol.*, 157: 105-132, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within +1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (-0.5±1); threonine (-0.4); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. The present invention thus contemplates functional or biological equivalents of an opioid receptor polypeptide as set forth above.

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman, et al. (1983). As will be appreciated, the technique typically employs a phage vector which can exist in both a single stranded and double stranded form. Typical vectors useful in site-directed mutagenesis include vectors such as the M13 phage (Messing, et al. 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the opioid receptor polypeptide sequence selected. An oligonucleotide primer bearing the desired mutated sequence is prepared, generally synthetically, for example, by the method of Crea, et al. (1978). This primer is then annealed to the singled-stranded vector, and extended by the use of enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as *E. coli* cells and clones are selected which include recombinant vectors bearing the mutation. Commercially available kits come with all the reagents necessary, except the oligonucleotide primers.

An "opioid receptor polypeptide" as defined for the purposes of the present invention is understood to be any opioid receptor polypeptide capable of binding opioid in any of its forms or analogs of opioid. In addition, an opioid receptor polypeptide of the invention is not limited to a particular source. It is believed that a number of species of the family of opioid receptor polypeptides are amenable to detection and isolation using the compositions and methods of the present inventions.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells.

IV. Expression Vectors

The present invention contemplates the use of expression vectors comprising polynucleotides that encode opioid receptor polypeptides. Preferably, the expression vectors of the invention comprise polynucleotides operatively linked to an enhancer-promoter. More preferably still, the expression vectors of the invention comprise polynucleotides operatively linked to a prokaryotic promoter. Alternatively, the expression vectors of the present invention comprise polynucleotide operatively linked to an enhancer-promoter that is a eukaryotic promoter, and the expression vectors further comprise a polyadenylation signal that is positioned 3' of the carboxyl-terminal amino acid and within a transcriptional unit of the encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region used in an adenovirus vector construct of the present invention comprises a polyadenylation signal of SV40 or the protamine gene.

An expression vector comprises a polynucleotide that encodes an opioid receptor polypeptide. Such a polynucleotide is meant to include a sequence of nucleotide bases encoding an opioid receptor polypeptide sufficient in length to distinguish said segment from a polynucleotide segment encoding a non-opioid receptor polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

Exemplary vectors include the mammalian expression vectors of the pCMV family including pCMV6b and pCMV6c. In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing opioid polypeptides by virtue of DNA incorporated into such expression vectors can be detected.

A DNA molecule of the present invention can be incorporated into a vector by a number of techniques which are well known in the art.

An expression vector of the present invention is useful both as a means for preparing quantities of the opioid receptor polypeptide-encoding DNA itself, and as a means for preparing the encoded polypeptide and peptides. It is contemplated that where opioid receptor polypeptides of the invention are made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic opioid receptor polypeptides are anticipated using the teaching of the disclosed invention, one likely expresses such sequences in eukaryotic hosts. However, even where the DNA segment encodes a eukaryotic opioid receptor polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant opioid receptor polypeptides is desired and a eukaryotic host is contemplated, it is most desirable to employ a vector such as a plasmid, that incorporates a eukaryotic origin of replication. Additionally, for the purposes of expression in eukaryotic systems, one desires to position the opioid receptor encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the opioid receptor polypeptide, an appropriate polyadenylation site.

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV1-5 series of vectors, the functionally similar pCMV6b and c vectors are available from the Chiron Corp. of Emeryville, Calif. and are identical except for the orientation of the polylinker region which is reversed in one relative to the other.

The universal components of the PCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter was added C. The sequence acts as a translational enhancer by decreasing the requirements for initiation factors in polypeptide synthesis. To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, $G_s$ alpha polypeptide, polypeptide phosphatase, synaptophysin, synapsin, insulin receptor, influenza hemagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMU that can cause spurious translation initiation. This codon should be avoided if possible in expression plasmids. A paper describing the construction and use of the parenteral pCMV1 and pCMV4 vectors has been published (Anderson et al., 1989b).

V. Transfected Cells.

The present invention provides for the use of recombinant host cells transformed or transfected with polynucleotide that encode opioid receptor polypeptides, as well as transgenic cells derived from those transformed or transfected cells. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook, et al., 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection is well-known in the art (Stratford-Perricaudet, et al. 1992).

A transfected cell can be prokaryotic or eukaryotic. Preferably, the host cells of the invention are eukaryotic host cells. More preferably, the recombinant host cells of the invention are COS-1 cells. Where it is of interest to produce a human opioid receptor polypeptides, cultured mammalian or human cells are of particular interest.

In another aspect, the recombinant host cells of the present invention are prokaryotic host cells. Preferably, the recombinant host cells of the invention are bacterial cells of the DH5a strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli* X1776 (ATCC No. 31537). These examples are, of course, intended to be illustrative rather than limiting.

Prokaryotes can also be used for expression. The aforementioned strains, as well as *E. coli* W3110 (F-, lambda-, prototrophic, ATCC No. 273325), bacilli such as *Bacillus subtilus*, or other enterobacteriaceae such as *Salmonella typhimurium* or *Serratus marcesans*, and various *Pseudomonas species* can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar, et al. 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang, et al. 1978; Itakura, et al. 1977; Goeddel, et al. 1979; Goeddel, et al. 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist, et al. 1980).

In addition to prokaryotes, eukaryotic microbes such as yeast can also be used. *Saccharomyces cerevisiaes* or common baker's yeast is the most commonly used among eukaryotic microorganisms, although a number of other strains are commonly available. For expression in Saccharomyces, the plasmid YRp7, for example, is commonly used (Stinchcomb, et al. 1979; Kingsman, et al. 1979; Tschemper, et al. 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman, et al. 1980) or other glycolytic enzymes (Hess, et al. 1968; Holland, et al. 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers, et al. 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

VI. Preparing Recombinant Opioid Receptor Polypeptides.

In some embodiments, the present invention contemplates use of a process of preparing opioid receptor polypeptides comprising transfecting cells with polynucleotide that encode opioid receptor polypeptides to produce transformed host cells; and maintaining the transformed host cells under biological conditions sufficient for expression of the polypeptide. The transformed host cells are eukaryotic cells or alternatively, the host cells are prokaryotic cells. More preferably, the prokaryotic cells are bacterial cells of the DH5α strain of *Escherichia coli*. Transfection may be accomplished using a herein before disclosed expression vector.

A host cell used in the process is capable of expressing a functional, recombinant opioid receptor polypeptide. A preferred host cell is a Chinese hamster ovary cell. However, a variety of cells are amenable to a process of the invention, for instance, yeasts cells, human cell lines including lymphocytes, and other eukaryotic cell lines known well to those of skill in the art.

Following transfection, the cell is maintained under culture conditions for a period of time sufficient for expression of an opioid receptor polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C. pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of an opioid receptor polypeptide. A suitable time depends inter alia upon the cell type used and is readily determinable by a skilled artisan. Typically, maintenance time is from about 2 to about 14 days.

Recombinant opioid receptor polypeptide is recovered or collected either from the transfected cells or the medium in which those cells are cultured. Recovery comprises isolating and purifying the opioid receptor polypeptide. Isolation and purification techniques for polypeptides are well known in the art and include such procedures as precipitation, filtration, chromatography, electrophoresis and the like.

VII. Antibodies.

In still another embodiment, the present invention contemplates antibodies immunoreactive with opioid receptor polypeptides. Preferably, the antibodies of the invention are monoclonal antibodies. Means for preparing and characterizing antibodies are well known in the art (See, e.g., Antibodies "A Laboratory Manual, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with an opioid receptor polypeptide comprising the steps of (a) transfecting recombinant host cells with polynucleotide that encode opioid receptor polypeptides; (b) culturing the host cells under conditions sufficient for expression of the polypeptides; (c) recovering the polypeptides; and (d) preparing the antibodies to the polypeptides. The present invention provides antibodies prepared according to the process described above.

A monoclonal antibody of the present invention can be readily prepared through use of well-known techniques such as those exemplified in U.S. Pat. No 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

VIII. Pharmaceutical Compositions.

In a preferred embodiment, the present invention provides pharmaceutical compositions comprising opioid receptor polypeptides or opioid receptor polypeptide agonists and/or antagonists in physiologically acceptable carriers.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g. Gabizon et al., 1990; Ferruti et al., 1986; and Ranade, 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

IX. Detecting Polynucleotide and the Polypeptides Encoded.

The present invention contemplates a process of detecting opioid receptor polypeptides, wherein the process comprises immunoreacting the polypeptides with antibodies prepared according to the process described above to form antibody-polypeptide conjugates, and detecting the conjugates.

In yet another embodiment, the present invention contemplates a process of detecting messenger RNA transcripts that encode opioid receptor polypeptides, wherein the process comprises (a) hybridizing the messenger RNA transcripts with polynucleotide sequences that encode the opioid receptor polypeptides to form duplexes; and (b) detecting the duplex. Alternatively, the present invention provides a process of detecting DNA molecules that encode opioid receptor polypeptides, wherein the process comprises (a) hybridizing DNA molecules with polynucleotide that encode opioid receptor polypeptides to form duplexes; and (b) detecting the duplexes.

The following examples are illustrative of various aspects of the invention. They are not limiting as to the invention or claims. One of ordinary skill will see many ways in which the Examples could be modified without departing from the scope and spirit of the invention.

EXAMPLE 1

Ligand-Receptor Binding Assays

One of the aspects of the invention involves methods for diagnosing CNS and immune system-specific opioid receptor agonists and antagonists. One of the ways to do this is via ligand-receptor binding studies. Ligand-receptor binding studies are used to identify those agents that bind to opiate/opioid recognition sites. In these studies, one measures the ligand binding of opiate/opioid agonists and antagonists to the different kinds of opiate/opioid receptors and binding proteins.

Ligand-receptor binding assays can be done in any of a number of methods known to those of skill. For example, one way to assay receptor-ligand binding is to use cell preparations that only express a single type opiate/opioid receptor. Membranes are prepared from cells transfected with cDNA's encoding (a) a putative CNS or immune system-specific opioid/opiate receptor or other binding protein or (b) classical neuronal opiate receptors of the δ, μ, and κ types. In some cases, it will be beneficial to use COS cells and transient expression vectors as well as stable, transformed CHO cell lines that express the receptors. These cells provide useful systems because, in their native state (i.e., without the introduction of foreign cDNA's) neither COS (derived from monkey kidney cells) nor CHO (Chinese hamster ovary) cells have detectable levels of any type opiate/opioid receptor. In other applications, one can transfect using electroproation.

As those of skill will appreciate, there are many ways to measure ligand-receptor binding. All such methods are within the scope of the invention, because the practice of these methods to isolate CNS and immune-system specific opioid/opiates is possible after the inventors' discovery of the nature and function of EBI1. One example of how to perform such an assay is given below. However, the invention is in no way limited to this one method of performing the assay. For example, a variety of cell systems, other than the CHO cell system, can be used. For example lymphocyte lines such as the B cell BJAB and the early pre T cell HSB lines can be used while expression vectors such as pSg5, pcDNAI/Amp, and pDR2 are also contemplated. Further, the concentrations, times, and precise reagents of the assay below may all be varied within parameters that are known in the art. Of course, there is a plethora of commercially available vectors available. Applicants presently use pSg5 for transfection of COS cells, but it is possible to switch vectors with ease.

A. Preparation of cell membranes

1. Remove culture medium from cell cultures.
2. Wash cell monolayers 2 x with $Ca^{2+}$ deficient PBS.
3. Add ice cold 50 mM Tris-HCl containing 1 mM EDTA, pH 7.4 (hypotonic buffer) to culture flasks.
4. Incubate flasks on ice for 30 minutes.
5. Harvest monolayers from flasks to 50-ml conical tubes. Use a rubber policeman to dislodge the monolayers. Freeze tubes by transferring to −70° C.
6. Thaw pellets on ice and then sonicate.
7. Centrifuge the sonicate at 1,000 x g for 10 minutes.
8. Remove supernatant and then centrifuge the supernatant for an additional 20 minutes at 28,000 g.
9. Resuspend this pellet (P2) in 50 mM Tris-HCl containing 100 mM EGTA and 8% (v/v) glycerol, pH 7.4.
10. Determine membrane protein in the P2 fraction (Lowry's protein assay).
11. Store in eppendorf tubes at −70° C. until needed for binding assays.

B. Ligand-receptor binding assays

1. Transfer the membranes from −70° C. to an ice bath. Once thawed, pellet the membranes in a microfuge and then wash twice in the binding assay buffer consisting of 5 mM Tris-HCl, pH 7.8, 0.32M sucrose and 100 μM phenylmethylsulfonylfluoride.
2. Dispense 100 μl portions (10–20 μg of protein) of membranes into a 96-well polypropylene microtiter plate (Costar Corporation; Cambridge, Mass.).
3. Add 50 μl of labeled opiate/opioid ($^3$H-DPDPE, $^3$H-DAMGO, $^3$H-U69,593 or $^3$H-diprenorphine) to all test wells.
4. Dispense 50 μl of unlabeled test agent to triplicate samples (titer concentration over the range of 0.1 nM to 100 μM).

5. Add 50 μl of 20 μM unlabeled naloxone to 4 wells (needed to measure nonspecific binding).

6. Add 50 μl of buffer to 4 wells (needed to measure total binding).

7. Incubate assay wells 60 minutes at 20° C.

8. Following incubation, and with vacuum applied, transfer the samples to Whatman G/F glass fiber filters.

9. Quickly, wash the filters with three 3-ml portions of buffer. (The buffer should be rapidly removed from the samples. The vacuum and good flow should be maintained from the time the samples are applied to the filters until the washing has been completed).

10. Dry filters and count in a liquid scintillant.

C. Analysis of binding data

1. Calculate the means and standard deviations for replicate samples.

2. Measure specific binding. Subtract the cpm measured in the presence of naloxone (nonspecific binding) from the total cpm measured in buffer, alone.

3. Determine the percent specific binding measured for unlabeled opiate/opioids (test agents). Subtract cpm for sample from total cpm measured in buffer alone. Divide this value by that measured for the specific binding (see 2).

4. Plot percent specific binding (y-axis) vs log concentration (x-axis).

5. Utilize nonlinear regression and an appropriate analysis package (e.g., LIGAND) to measure Hill coefficients and Kd values.

EXAMPLE 2

Functional Receptor Signaling Assays

The inventors' discovery that EBI1 is an opioid binding protein allows for the use of functional receptor signalling assays to determine the cellular effects of opioid receptor agonists and antagonists. Functional receptor signaling assays can be used to verify the activity of an agonist or antagonist for opioid receptors. One manner of performing such an assay utilizes intact cells, for example COS or CHO cells, that express a single variety of opiate/opioid receptor. In these studies the effect that an opiate/opioid agonist or antagonist has on receptor-mediated signaling is identified. The effects of potential agonists and antagonists on the production of cAMP, generation of phosphinositols, and calcium transients and other cellular functions can all be measured in manners know to those of skill in the art. To define the effects of potential antagonists on the activation of these signaling systems, one measures the inhibition of responses elicited by agonists, for example MET-ENK, DPDPE, DAMGO, and morphine.

While specific protocols for performing functional receptor signaling assays are detailed below, the invention is in no way limited to these particular manners of performing the assays. Rather, as understood by those skilled in the field, variations may be made in the processes, without departing from the spirit and scope of the invention.

A. Measurement of cAMP by conventional radioimmunoassay (RIA)

1. Plate $10^5$ cells/well to 24 well tissue culture plates.

2. Incubate 48 hours at 37° C. in tissue culture incubator.

3. Immediately prior to assay replace culture old medium with one-ml portions of DME supplemented with 1 mM 3-isobutyl-1-methylxanthine.

4. Incubate plates for 5 minutes at 37° C.

5. Transfer plates to an ice bath and then add 10 μl of 10 μM forskolin (prepared in DMSO) or 10 μl of DMSO solvent to the wells.

6. Add test reagent(s) (i.e., opiate/opioid agonist and/or antagonist) and gently swirl plate to mix. In the case where potential antagonists are to be tested add this agent first and then the agonist to the wells.

7. Incubate plates for an additional 20 minutes at 37° C.

8. Following the incubation period, transfer the plates to ice and stop the reactions by addition of 100 μl of 100% ice cold TCA.

9. Transfer contents of wells to 4.5 ml polypropylene tubes and spin at 4000 rpm for 15 minute in a 4°–8° C. centrifuge.

10. Transfer clear supernatant to 10 ml glass tubes; save pellets for Lowry protein determination.

11. Wash supernatant with three 3-ml portions of hydrated diethyl ether.

12. Boil remaining ether from samples by incubation in an 80° C. water bath.

13. Measure cAMP content in the samples suing a standard curve and commercially available RIA kit.

B. Adenylyl cyclase activity measured as $^3$H-adenine incorporation into cAMP

1. Plate cells at $10^5$/well to 24 well culture plates and incubate in an tissue culture incubator for two days.

2. Immediately prior to assays replace culture medium in the wells with one-ml portions of DME supplemented with 1 mM 3-isobutyl-1-methylxanthine.

3. Return plates to 37° C. tissue culture incubator (10% CO2) and incubate for 5 minutes.

4. Then add 3μCi of [3H]adenine to each well and incubate at 37° C. for an additional 60 minutes.

5. Aspirate labeled medium and replace it with fresh DME containing either 10 μl of 10 μM forskolin (prepared in DMSO) or 10 μl of DMSO.

6. Add test reagent(s) (i.e., opiate/opioid agonist or antagonist) and gently swirl plates to mix. In the case where potential antagonists are to be tested add this agent before agonist.

7. Incubate the cells with test reagents for 20 minutes at 37° C.

8. Following incubation, transfer the plates to ice and stop the reactions by addition of 550 μl of 0.27N perchloric acid.

9. Add 50 μl of 32P-labeled cAMP (10,000 CPM; STANDARD) to each well.

10. Harvest supernatants from wells and apply to prepared columns (Bio-Rad #731–1550) of prewashed Dowex 50.

11. Wash wells with 500 μl of 0.1M perchloric acid and apply washes to Dowex columns.

12. Wash Dowex columns with two ml of 0.1M perchloric acid.

13. When all perchloric acid has dripped from Dowex beds, then align the Dowex columns directly above another column containing alumina gel.

14. Add 10 ml of 0.1M perchloric acid to Dowex column.

15. When flow through complete separate the Dowex and alumina columns and wash the alumina resin with 10 ml of $H_2O$.

16. Discard perchloric acid and water washes to radioactive waste.

17. Elute radioactive cAMP fro alumina columns with 6 ml of 0.4M imidazole.

18. Count sample sin liquid scintillation.

19. Determine the recovery of $^{32}$P-cAMP in the column eluates. Use these values to estimate the recovery of $^3$H-cAMP in the samples.

C. Measurement of Phosphoinositols

1. Plate cells to 12-well culture plates at a density of $10^5$/well.

2. Incubate plates for 24 hours in tissue culture incubator.

3. Label cells by incubation for an additional 24 hours with $^3$H-inositol (1 µCi/ml).

4. Remove excess label from wells by aspiration and 2x washes with PBS.

5. Incubate cells for an additional 30 minutes at 37° in PBS containing 10 mM LiCl.

6. Transfer plates to ice and replace the buffer with fresh PBS containing the test reagents (opiate/opioid agonists and antagonists) and 10 nM LiCl. In the case where potential antagonists are to be tested add the antagonist first and then the agonist.

7. Incubate for 6 minutes at 37° C.

8. Terminate the reactions by transferring the plates to ice, aspirating the medium, and then adding one-ml of 5% TCA.

9. Apply samples to Bio-Rad AG 1-X8 columns and serially elute (1) inositol monophosphate, (2) inositol biphosphate and (3) inositol triphosphate with buffers containing (1) 5 mM disodium tetraborate, 180 mM sodium formate; (2) 0.1M formic acid, 0.4M ammonium formate; and (3) 0.1M ammonium formate.

10. Measure the radioactivity in these eluates using liquid scintillation.

D. Measurements of intracellular calcium in adherent cells attached to coverslips 1. Seed cells on to sterile glass coverslips which have previously been placed in culture dishes.

2. Incubate the cells in a tissue culture incubator for 2–3 days at 37° C.

3. To load the cells with the calcium sensitive dye fura-2 replace the culture medium with 10 ml of fresh DME containing 4 µM fura-2 acetoxymethyl ester.

4. Incubate the dishes for 20 minutes at 37° C.

5. Wash the coverslips twice in the assay buffer solution containing 20 mM HEPES (pH 7.4), 115 mM NaCl, 5.4 mM KCl, 2.2 mMCaCl$_2$, 0.8 mM MgCl$_2$ and 13.8 mM glucose.

6. Transfer the coverslips to culture dishes containing 10 ml of this buffer and preincubate them for 10 minutes (room temperature) prior to assay.

7. Place the coverslips in the assay chamber.

8. Monitor fura-2 fluorescence in a microscope equipped with epifluorescence optics. (Select excitation at 340 and 380 nm; calculate [$Ca^{2+}$]; by rationing of 340:380 nm intensities).

E. Measurements of intracellular calcium in non adherent cells

1. Remove cells from culture and wash twice in a loading medium consisting of DMEM supplemented with 5% dialyzed fetal bovine serum.

2. Resuspend the cells to $10^6$/ml in the loading medium and transfer to 50-ml conical tubes.

3. Prepare a fresh solution of Indo-1 dye (Molecular Probes) by dissolving 1 mg of the dye in 50 µl DMSO and then diluting with 200 µl of the DMEM loading medium.

4. Add 3 µl of the prepared dye for each ml of cells, mix and incubate the tubes for 30 minutes at 37° C. in a 10% $CO_2$ atmosphere.

5. Wash the cells once in the loading medium and then twice in serum free DMEM.

6. Resuspend the cells to $10^6$/ml in serum free DMEM and hold on ice, in the dark until analyzed.

7. Measure the violet/blue fluorescence ratio by cytofluorometry as previously described by Rabinovitch et al. (1986) and for FIG. 14 and FIG. 15.

EXAMPLE 3

Opioid Peptides Affect Immune Cell Migration

A. SUMMARY

Cell migration from one anatomic site to another is regulated by activation signals that initiate a cascade of biochemical and morphological events and coordinate the expression of specific adhesion molecules. In this study factors which regulate the in vitro migration of pre-B acute lymphoblastoid leukemia (ALL) cells were identified. Physiological concentrations (i.e., $\leq 10^{-10}$M) of the endogenous opioid neuropeptide methionine-enkephalin (MET-ENK) and the synthetic enkephalins DAMGO and DADLE induced the migration of NALM 6 and LAZ 221 pre-B ALL cells. The stimulation of NALM 6 and LAZ 221 cells with MET-ENK correlated with both an increase in their migration and a transient up-regulation in the CD9 surface marker. These effects were reversed by naloxone suggesting that both the migration to MET-ENK and the enkephalin-induced expression of CD9 molecules on the pre-B ALL cells were mediated via classical opiate/opioid receptors. When the NALM 6 cells were preincubated with an anti-CD9 mAb their migration to MET-ENK was markedly reduced. The inventors' studies show that enkephalins are potent stimulants for the migration of pre-B ALL cells and suggest that CD9 molecules regulate the enkephalin-induced motility of these leukemia cells. These findings suggest that CD9 plays an important role in the migration of lymphoid cells.

Opioid peptides are known to be potent chemoattractants for normal, mature leukocytes (Heagy et al., 1990); however, their effects on the migration of leukemic cells or early pre-lymphoid progenitor cells are unknown. In this report the numbers show that MET-ENK and enkephalin analogs stimulate the in vitro migration of two pre-B acute lymphoblastoid leukemia (ALL) lines, NALM 6 and LAZ 221. Exposure of these ALL cells to MET-ENK results in a discrete and transient increase in the expression of CD9 as well as an enhancement in their motility. Moreover, the preincubation of NALM 6 cells with anti-CD9 mAb inhibits their migration to MET-ENK. These novel findings show that opioid peptides are stimulants for the movement of such leukemic cells and suggest that CD9 molecules regulate the motility of pre-B ALL cells. The inventors' studies provide new insights into the mechanisms by which opioid peptides affect cell migration.

B. MATERIALS AND METHODS

Cells: The pre-B ALL cell lines NALM 6 and LAZ 221 (CD19$^+$, CD9$^+$, CD10$^+$, sIg$^-$) and the EBV-transformed B lymphoblastoid cell line LAZ 388 (CD19$^+$, CD20$^+$, CD9$^-$, CD10$^-$) have been described previously (Shipp et al., 1989). The LAZ 221 (pre-B cell) and LAZ 388 (EBV-transformed B cell) lines were established from donor cells harvested from a patient at the Dana-Farber Cancer Institute, Boston, Mass. (Shipp et al., 1989) and were obtained for these studies from Dr. Jerome Ritz. Cells were passaged (1–2× $10^5$/ml) every 2–4 days in RPMI 1640 medium (BioWhittaker, Inc., Walkersville, Md.) supplemented with 2 mM glutamine, a solution of 100 U/ml-100 µg/ml of penicillin-streptomycin (Gibco Laboratories, Grand Island, N.Y.), and 10% bovine serum (Hyclone Laboratories, Inc., Logan, Utah) and maintained at 37° C. in a 5% $CO_2$ tissue culture incubator.

Reagents and Antibodies: The naturally occurring pentapeptide MET-ENK (Tyr-Gly-Gly-Phe-Met), and the synthetic peptides [D-Ala$^2$,D-Leu5]-enkephalin (DADLE), [D-Ala$^2$, Me-Phe$^4$, Gly(ol)$^5$]-enkephalin (DAMGO), and FMLP were purchased from Sigma Chemical Co. (St. Louis, Mo.). Naloxone (Narcan) was obtained from Dupont Pharmaceuticals (Manati, Puerto Rico).

Anti-CD9 and -CD10 mAb of the IgG1 isotype were from Biodesign International (Kennebunkport, Me.) and those of the IgG2a isotype were obtained from AMAC, Inc. (Westbrook, Me.). Anti-CD20 (IgG1), -CD14 (IgG2a), -CD29 (IgG1) and -CD54 (IgG1) mAb were from Biodesign International. Anti-CD72 (IgG2a), and -CD23 mAb were from The Binding Site (Birmingham, England) and anti-CD22 (IgG1) was from AMAC. Anti-CD2 (IgG1), -CD3 (IgG2a), -CD11a (IgG1), -CD11b (IgG1), -CD18 (IgG1), -CD45 (IgG2a), anti-CD 58 (IgG1) were prepared as ascites developed in Balb/c mice. The hybridomas producing anti-CD2 (HB195), -CD3 (CRL 8001), -CD11a (HB 202), -CD11b (HB204), -CD18 (HB203), -CD45 (HB196) and CD58 (HB205) were obtained from the American Type Culture Collection (Rockville, Md.). Anti-CD19 mAb (IgG1) was a gift from Dr. Ken Anderson, Dana-Farber Cancer Institute, Boston, Mass. The mAb recognizing VLA's 1–6 were from the V Human Leukocyte Typing Workshop (subpanel 6) and the DE9N anti-VLA b chain mAb (IgG1) was provided by Dr. Jeff Bergelson, Dana-Farber Cancer Institute, Boston, Mass. (Bergelson et al., 1992). The MOPC 21 myeloma protein (IgG1) which was used as a control was purchased from organon Teknika Cappel (Durham, N.C.).

Migration Assays: Cell migration was measured using microchemotaxis chambers (Neuroprobe, Inc., Cabin John, Md.) as previously described (Heagy et al., 1990). Cells ($5 \times 10^6$/ml) were separated from peptides in the lower wells by a nitrocellulous filter (Sartorious, 5 µm pore; Neuroprobe, Inc.) and were incubated for 75–90 minutes at 37° C. In some studies the cells were preincubated with $10^{-5}$M naloxone for 15 h at 37° C. or anti-CD9, -CD10, or -VLA 4 monoclonal antibodies for 30 minutes at 4° C. and then washed in assay buffer before their addition to the migration chamber. Cells which migrated into the filters were fixed, stained with Congo red dye (Sigma), identified by fluorescence microscopy and then enumerated utilizing an optical image analyzer (Optomax V image analyzing system; Analytical Instruments, Hollis, N.H.). In some studies the cells were identified visually and photographed with the use of a fluorescence microscope.

Forward and right angle light scatter analysis of the morphological response to MET-ENK: The effect of MET-ENK on cell morphology were measured using flow cytometric analysis of forward and right angle light scatter as previously described (Sklar et al., 1984). For these studies $10^6$ cells were resuspended in one-ml of PBS, activated by the addition of MET-ENK or maintained in the PBS buffer alone, and then, incubated for 5 minutes at 37° C. In the studies with naloxone the samples were first preincubated on ice for 15 minutes with or without the opiate receptor antagonist. Samples were analyzed on a Becton Dickinson FACS SCAN flow cytometer with excitation at 488 nm (Sklar et al., 1984). Histograms of light scattering were obtained by analyzing 10,000 cells for each sample. Data analysis was performed using the Lysys System software package.

Immunofluorescence Staining and Flow Cytometric Analysis of Cell Surface Molecules: Cells were resuspended at $1 \times 10^6$/ml in PBS and then incubated for periods of 5 to 120 minutes at 37° C. with MET-ENK at doses of 0 to $10^{-5}$M. Incubations were terminated by transferring samples to an ice bath and then pelleting the cells by centrifugation at 1800 rpm for 5 minutes at 4° C.

Immunofluorescence staining was carried out in 4-ml tubes maintained in an ice water bath. Cells ($10^6$) in 100 µl volumes of PBS were incubated with the primary antibody for 30 minutes, washed, and then stained by a second incubation with affinity purified FITC conjugated F(ab)'s goat anti-mouse Ig (Tago, Burlingame, Calif.). Cells were subsequently fixed within a 2% solution of formalin and maintained in the dark at 10° C. until analyzed.

Flow cytometric analysis was performed using a FACS SCAN Flow Cytometer (Becton Dickinson, Mountain View, Calif.) equipped with a HP9000 Series computer and the Lysys System software analysis package. Data were collected as histograms depicting the fluorescence intensity for 5,000 to 10,000 cells per sample.

The non-binding IgG1 MOPC myeloma protein, anti-macrophage/monocyte specific CD14 (MO2; IgG2) and anti-T cell specific CD3 (OKT3; IgG2a) mAb were employed as nonreactive controls for measuring the autofluorescence of B cells.

C. RESULTS

Figure 1A:
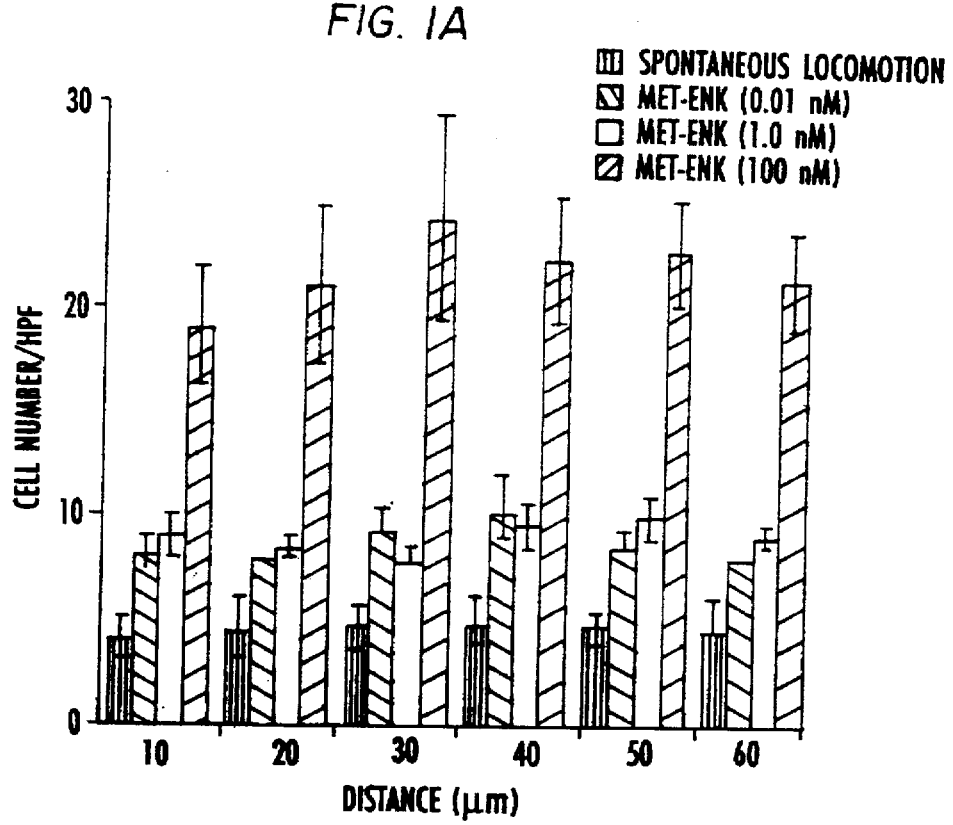
FIG. 1, Panels A and B. NALM 6 and LAZ 221 cells migrate to the opioid pentapeptide methionine- enkephalin. MET-ENK was prepared in the assay buffer consisting of Dulbecco's modified PBS and 0.1% chick egg albumin and then added in 35 μl volumes to the lower wells of the chemotaxis chamber. A Sartorius (8 μm pore) nitrocellulose filter was placed between the upper and lower reservoirs and the cells ($5 \times 10^6$/ml) were then added to the upper wells in 60 μl portions of the assay buffer. Following a 90 minute incubation at 37° C. the filters were removed, fixed, and stained with Congo red dye as previously described (Heagy et al., 1990). Cells which migrated into the filter were enumerated utilizing fluorescence microscopy and an Optimax V image analyzing system. Ten high power fields (hpf) were measured at 10 mm distances through the filter. Data are presented as the means ±S.D. for 30 values (i.e., 10 readings x triplicate assays). Note: The scales for the y-axis are different in Panels A & B.
Figure 1B:
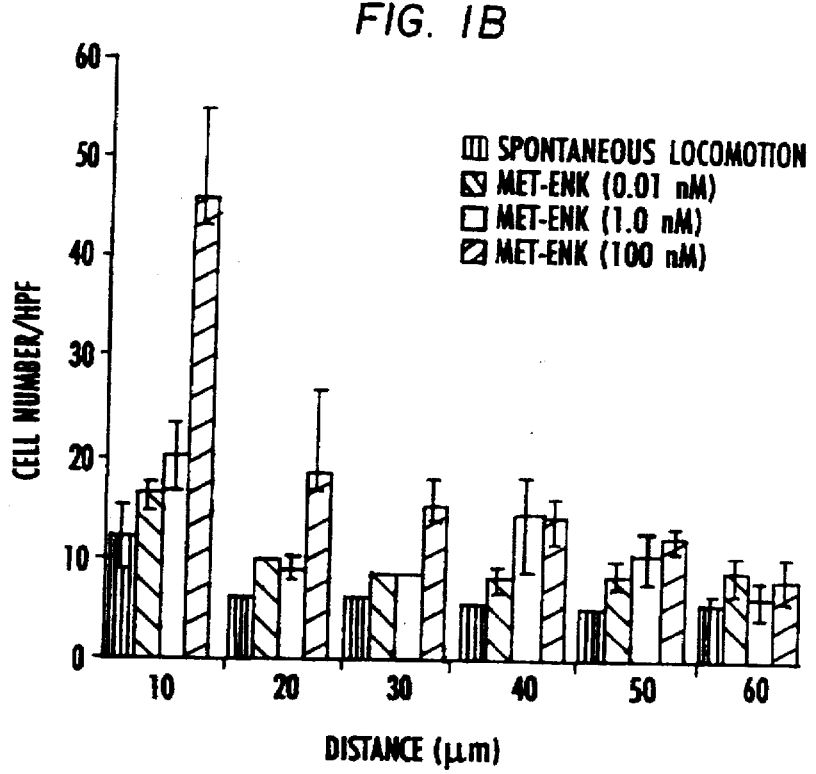

Opioid peptides stimulate the migration of pre-B acute lymphoblastic leukemia cells. The naturally occurring opioid pentapeptide MET-ENK was a potent stimulus for the migration of NALM 6 and LAZ 221 (pre-B ALL) but not LAZ 388 (EBV-transformed) cells (FIG. 1 and Table 1). The number of NALM 6 or LAZ 221 cells which migrated to MET-ENK was greater than that which responded to the assay buffer, alone (spontaneous locomotion) (p, $\leq 0.01$) (FIG. 1 and Table 1). The effects of MET-ENK on the migration of these pre-B ALL cells were dose dependent and detected at concentrations below the physiological range (i.e., $\leq 0.01$ nM) (FIG. 1).

TABLE 1

The pre-B acute lymphoblastoid leukemia cell lines NALM 6 and LAZ 221 migrate to natural synthetic enkephalins.*

| | | Peptides: [100 nM] | | | | |
|---|---|---|---|---|---|---|
| Cells: | Spontaneous locomotion | FMLP (nonanalgesic) | DesTyr-LEU-ENK (nonanalgesic | MET-ENK | DAMGO | DADLE |
| NALM 6 | 2190[τ] | 3198 | 3085 | 6952 | 5070 | 6240 |
| | | (p, NS; $\geq 0.05$)[‡] | (p, NS; $\geq 0.05$) | (p, $\leq 0.01$) | (p, $\leq 0.01$) | (p, $\leq 0.01$) |
| LAZ 221 | 1886 | 2906 | 2010 | 6199 | 4602 | 4405 |
| | | (p, NS; $\geq 0.05$) | (p, NS; $\geq 0.05$) | (p, $\leq 0.01$) | (p, $\leq 0.01$) | (p, $\leq 0.01$) |
| LAZ 388 | 1938 | 1914 | 2244 | 1986 | 2043 | 2283 |
| | | (p, NS; $\geq 0.05$) | (p, NS; $\geq 0.05$) | (p, $\leq 0.01$) | (p, $\leq 0.01$) | (p, $\leq 0.01$) |

*Assays were as described for FIG. 1.
[τ]Migration was scored as described for FIG. 1. The numbers presented are cell counts obtained by adding the values measured at 10 µm intervals through the filters.
[‡]The statistical significance of differences between the treatments was analyzed by a Dunnets multiple comparison test.

The synthetic enkephalins DADLE and DAMGO enhanced, albeit modestly, the migration of NALM 6 and LAZ 221 cells (p, ≦0.05) (Table 1). Whereas MET-ENK and the synthetic enkephalins were stimulatory the neutrophil chemotactic agent FMLP and the non-analgesic peptide Des-Tyr-LEU-ENK had no effect on the migration of the pre-B ALL cells (p, ≦0.05).

The migration of LAZ 388 cells to MET-ENK was equivalent to their spontaneous locomotion (response to assay buffer, alone) (p, N.S. ≦0.05)(Table 1).

Figure 2A:
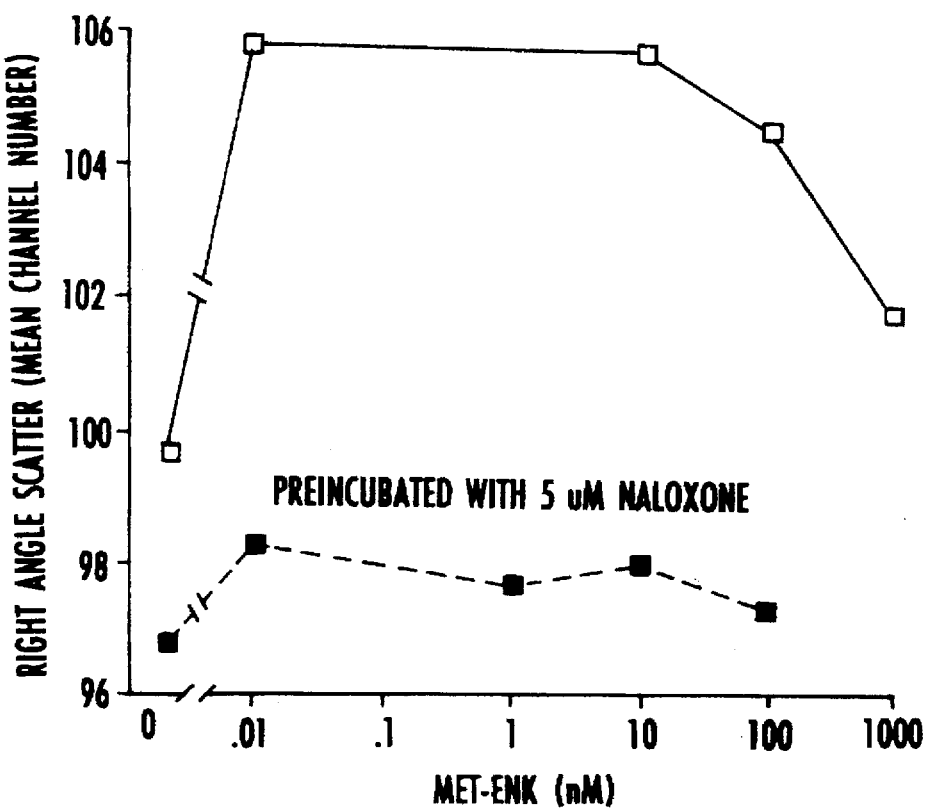
FIG. 2, Panels A and B. Methionine-enkephalin induces a morphological change in NALM 6 cells. NALM 6 cells ($10^6$/ml) were preincubated in PBS alone or containing $10^{-5}$M naloxone for 15 minutes on ice, stimulated with the indicated concentrations of MET-ENK and then incubated for an additional 5 minutes at 37° C. Analysis of forward and right angle light scatter was performed using a Becton Dickinson FACS SCAN flow cytometer as described (Sklar et al., 1984). Histograms of light scatter were obtained by analyzing 10,000 cells per sample. Data are expressed as mean channel number (y-axis) vs concentration of MET-ENK (x-axis). Panel A, right angle light scatter for samples preincubated in PBS alone (□—□) or PBS with $10^{-5}$ M naloxone (■—■). Panel B, forward light scatter from samples preincubated in PBS alone (○—○) or PBS with $10^{-5}$ M naloxone (●—●).
Figure 2B:
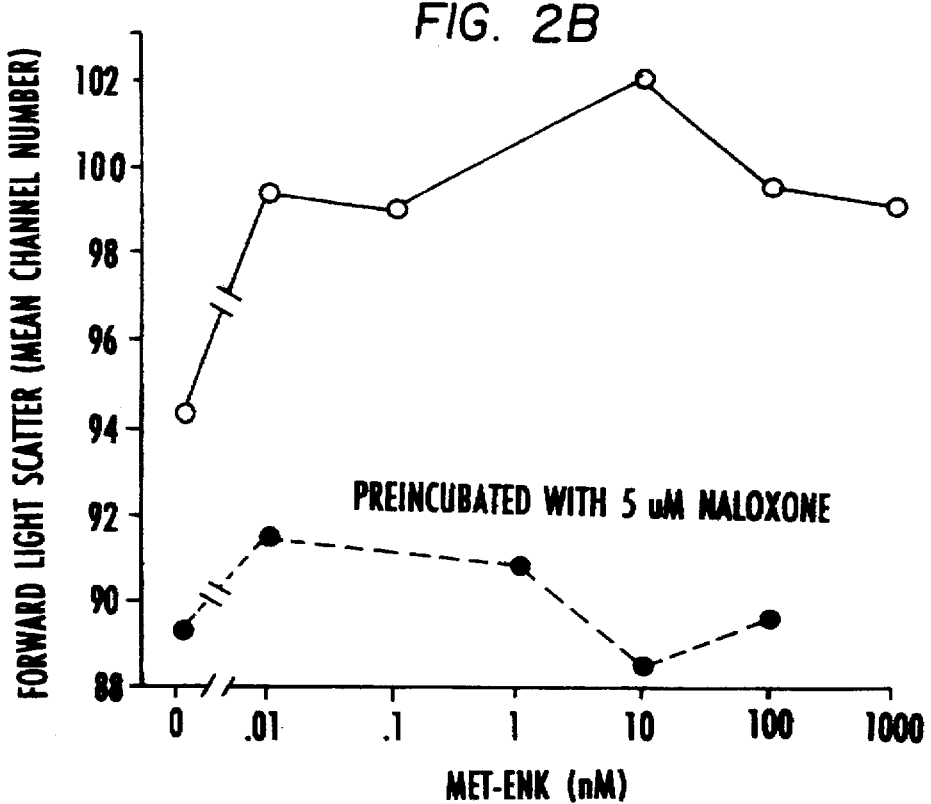

When applied directly to the NALM 6 cells, MET-ENK caused a rapid morphological response. MET-ENK induced an increase in light scatter (right angle and forward) that is characteristic of the cell flattening and membrane spreading (i.e., increase in surface area) response preparatory to migration (FIG. 2). This morphological response was dose dependent and occurred with MET-ENK concentrations as low as 0.01 nM (FIG. 2).

The chemoattractant activity of methionine-enkephalin is inhibited by naloxone. The opiate receptor antagonist naloxone inhibited the migration of NALM 6 cells to MET-ENK (Table 2). Spontaneous locomotion resulting from the random movement of unchallenged cells was equivalent for naloxone treated and nontreated cells (p, NS, ≧0.05) (Table 2).

TABLE 2

Naloxone inhibits the migration of NALM 6 cells to methionine-enkephalin.*

| | Spontaneous locomotion | | MET-ENK (1 nM) | | MET-ENK (100 nM) | |
|---|---|---|---|---|---|---|
| | without | with[τ] | without | with | without | with |
| Cell counts[¢] | 1647 | 1350 | 2925 | 1251 | 3492 | 1476 |
| p values[¦] | | (NS; ≧0.05) | | (0.01) | | (0.01) |
| % Response[¶] | | 82 | | 43 | | 42 |

*NALM 6 cells were cultured in RPMI 1640 medium supplemented with 2% FBS, 100 μg/ml of penicillin/streptomycin and 2 mM glutamine or in the culture medium containing $10^{-5}$M naloxone for 15 h at 37° C. in a 5% $CO_2$ atmosphere. Viability of the cells incubated with or without naloxone was equivalent (≧96%) as judged from vital staining with trypan blue. NALM 6 cells treated with naloxone were added to the upper wells of the migration chamber in assay buffer that contained naloxone ($10^{-5}$M). Migration was allowed to proceed for 75 minutes at 37° C.
[τ]Without = cells that were incubated in assay buffer alone; with = cells that were incubated in $10^{-5}$M naloxone.
[¢]Migration was scored as described for FIG. 1. The numbers presented are cell counts obtained by adding the values measured at 10 μm interval through the filters.
[¦]The statistical significance of differences between treatments was analyzed by a student t test.
[¶]Percent = [(Sum for cells incubated with naloxone)/(sum for cells incubated without naloxone]) × 100%.

The morphological response (i.e., membrane spreading and cell flattening) of NALM 6 cells to MET-ENK was inhibited by preincubation with naloxone (FIG. 2). Interestingly, whereas MET-ENK caused an increase in the light scattering from the cells, the opiate receptor antagonist naloxone shifted the baseline measurement below that for the control (i.e., cells maintained in PBS alone) (FIG. 2).

Figure 4A:
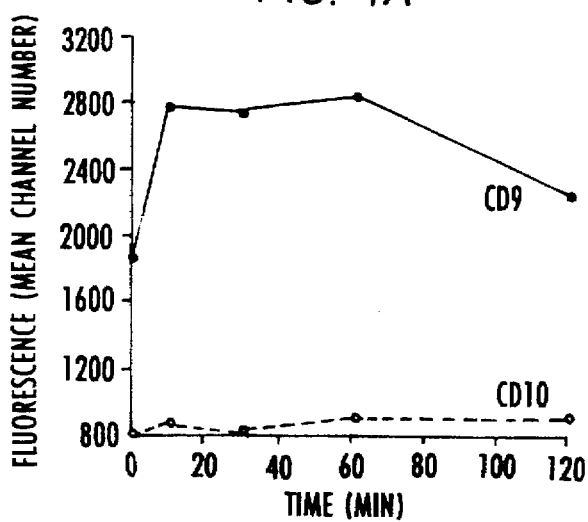
FIG. 4, Panels A-C. Methionine-enkephalin causes a rapid and dose-dependent increase in the CD9 but not CD10 molecules expressed on pre-B leukemic cells. Data are presented as mean fluorescence intensities measured for 10,000 cells labeled with anti-CD9 or CD10 mAb. In Panel A, the NALM 6 Cells were incubated with MET-ENK ($10^{-7}$M) for the times indicated. In Panel B, the LAZ 221 cells were incubated with MET-ENK at the doses indicated for 5 minutes at 37° C. In Panel C, the LAZ 221 cells were incubated at 37° C. for 15 minutes with MET-ENK ($10^{-7}$M) (●—●) or with both MET-ENK and naloxone ($10^{-5}$M) (○—○). The anti-CD9 and anti-CD10 mAb used for these experiments were of the IgG2a isotype.
Figure 4B:
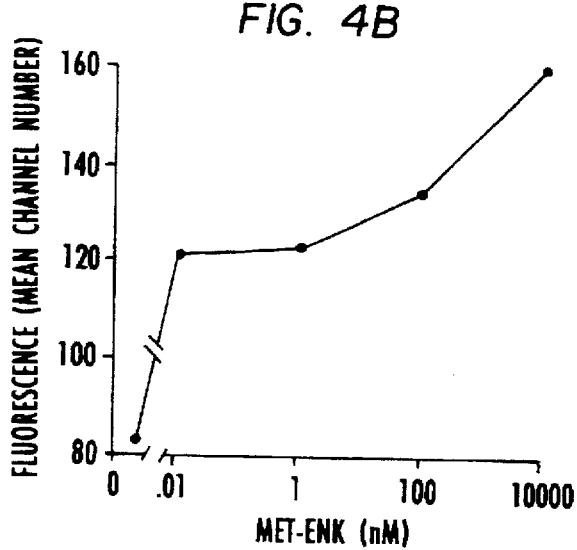
Figure 4C:
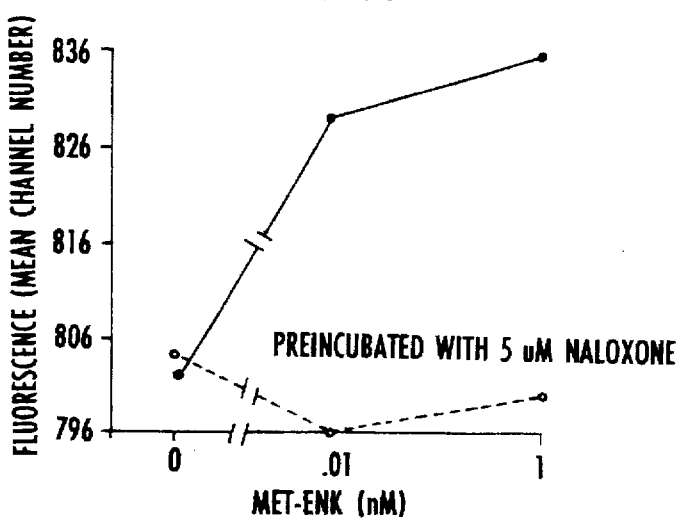

Methionine-enkephalin modulates expression of CD9 on pre-B acute lymphoblastic leukemia cells. Incubation of NALM 6 or LAZ 221 cells with MET-ENK resulted in a transient increase in their surface expression of CD9 but not CD10 molecules (FIG. 3 and FIG. 4). Brief incubations of the pre-B ALL cells with MET-ENK (i.e., ≦10 minutes) caused this increase in CD9 expression (FIG. 4 A). The enhancement in CD9 expression was sustained for periods of 60 minutes but declined to near baseline by 120 minutes (FIG. 4 A). The effects of MET-ENK on CD9 expression were dose and temperature dependent. As indicated (FIG. 4 B), CD9 expression on LAZ 221 cells was increased by MET-ENK doses as low as $10^{-11}$M and further enhanced when the opioid dose was titered to $10^{-5}$M (FIG. 4 B). MET-ENK caused CD9 expression to increase when the cells were warmed to 37° C. but had no effect when they were maintained in an ice water bath (Data not shown). This MET-ENK induction of CD9 molecules was totally blocked in the presence of a 100 fold excess of naloxone (FIG. 4 C). Whereas MET-ENK caused the surface expression of CD9 to increase the enkephalin had no effect on CD10 expression (FIG. 3 and FIG. 4 A).

In order to assess the specificity of the effects of MET-ENK on CD9 molecules a study was made of other cell surface antigens. Immunofluorescent staining of NALM 6 and LAZ 221 lines confirmed the pre-B phenotype previously described for such leukemic cells (Letarte et al., 1993). Samples of the pre-B ALL cells were labeled with monoclonal antibodies recognizing CD9 and CD10 markers as well as CD19, CD22, CD72, CD23 and certain VLA's (FIG. 3 and Table 3). Monoclonal antibodies directed against anti-VLA 4 (CD49d) or -5 or the common VLA b1 chain (CD29) but not those against VLA-1, -3, -2, or -6 labeled the NALM 6 line (Table 3). Staining for these β-1 integrins was equivalent on NALM 6 cells incubated with (+) or without (−) MET-ENK (Table 3). With the pre-B ALL cells the fluorescence intensity measured for CD11a, CD11b, and CD18 (b-2 integrins) was near that of the IgG1 isotype control (i.e., between 1 and 1.5 x the control value) (Table 3) regardless of whether the cells were incubated with (+) or without (−) MET-ENK (Table 3).

TABLE 3

Methionine-enkephalin effects on the surface expression of lymphocyte determinants.

| | | Fluorescence* | | | | | |
|---|---|---|---|---|---|---|---|
| | Antibody | NALM 6 | | LAZ 221 | | LAZ 388 | |
| Cell Determinant | Isotype | (−) | (+)[τ] | (−) | (+) | (−) | (+) |
| CD11a (LF1α) | IgG1 | ND[‡] | ND | 1.0 | 1.1 | 12.4 | 11.4 |
| CD11b (Mac 1) | IgG1 | 1.0 | 1.1 | 1.4 | 1.5 | 1.5 | 1.5 |
| CD18 (Integrin β chain) | IgG1 | 1.1 | 1.4 | 1.0 | 1.1 | 11.9 | 10.1 |
| CD54 (ICAM-1) | IgG1 | 9.3 | 10.5 | 1.5 | 1.5 | 18.7 | 16.6 |
| CD44 (homing receptor) | IgG1 | 1.0 | 2.2 | ND | ND | 79.0 | 84.6 |

TABLE 3-continued

Methionine-enkephalin effects on the surface expression of lymphocyte determinants.

| Cell Determinant | Antibody Isotype | NALM 6 (−) | NALM 6 (+)[τ] | Fluorescence* LAZ 221 (−) | LAZ 221 (+) | LAZ 388 (−) | LAZ 388 (+) |
|---|---|---|---|---|---|---|---|
| CD19 | IgG1 | ND | ND | 1.7 | 1.9 | 8.6 | 8.0 |
| CD58 (LFA-3) | IgG1 | 1.0 | 0.9 | 1.7 | 1.9 | 22.4 | 21.8 |
| CD22 | IgG1 | 2.3 | 3.1 | ND | ND | 11.4 | 11.1 |
| CD20 | IgG1 | 1.5 | 1.3 | 1.0 | 1.1 | 1.7 | 1.7 |
| CD72 | IgG2a | 1.6 | 2.8 | ND | ND | 1.4 | 1.7 |
| CD29 (VLA-β chain) | IgG1 | 8.4 | 9.3 | 1.7 | 1.9 | 11.4 | 11.2 |
| VLA-β; DE9N[‖] | IgG1 | 13.6 | 13.8 | 5.8 | 5.6 | 11.5 | 11.1 |
| VLA-1 | IgG1 | 1.1 | 0.6 | ND | ND | 1.8 | 2.0 |
| VLA-3 | IgG | 1.1 | 0.7 | ND | ND | 1.0 | 1.0 |
| VLA-5 | IgG1 | 5.2 | 4.9 | ND | ND | 1.0 | 1.0 |
| CD49b (VLA-α2 chain) | IgG1 | 1.0 | 0.9 | ND | ND | 1.0 | 1.0 |
| CD49f (VLA-α6 chain) | IgG1 | 1.8 | 1.3 | ND | ND | ND | ND |
| CD49d (VLA-α4 chain) | IgG1 | 3.9 | 4.4 | ND | ND | ND | ND |
| CD23 | IgG1 | 1.8 | 1.6 | ND | ND | 68.2 | 70.7 |
| CD45 (T200) | IgG2a | 1.1 | 1.0 | ND | ND | 27.4 | 27.3 |
| CD4 | IgG2a | 1.0 | 1.0 | 1.0 | 1.0 | ND | ND |
| CD2 (LFA-2 | IgG1 | ND | ND | 0.9 | 1.0 | 1.0 | 0.9 |

*Cells were labeled for analysis as described for FIGS. 3 and 4. Fluorescence values were measured from histograms collected for samples of 5,000 or 10,000 cells. Data are expressed as ratios: [(channel number measured for indicated mAb)]/[(mean value determined for isotype matched control)].
[τ]Cells were incubated for 30 minutes at 37° C. in PBS alone (−) or PBS containing $10^{-7}$M MET—ENK (+)
[‡]ND = Not Done.
[‖]Two anti-VLA-β1 (CD29) mAb were employed for these studies; the data obtained for these mAb are listed for anti-CD29 (VLA-β chain) and VLA-β; De9N.

As expected, immunofluorescent staining of LAZ 388 cells (EBV-transformed, mature B lymphocyte line) revealed a phenotype characteristic of mature B cells and different from that of the pre-B ALL lines (Table 3). Anti-CD11a, -CD18, and -CD54 monoclonal antibodies stained the LAZ 388 cells; the level of expression measured for these determinants was equivalent for the MET-ENK-treated (+) and nontreated (−) cells (Table 3).

Anti-CD9 monoclonal antibody blocks NALM 6 cell migration to methionine-enkephalin. The migration of NALM 6 cells to MET-ENK was inhibited when the cells were preincubated with anti-CD9 but not anti-CD10 or anti-CD29 mAb (Table 4). When the control cells (incubated in assay buffer, alone) or those pretreated with anti-CD10 or anti-CD29 mAb were added to the upper wells of the migration chamber the cells migrated toward MET-ENK in the lower chamber. On the other hand, most of the cells which were pretreated with the anti-CD9 mAb remained on the surface (i.e., at the origin) with few moving down toward the enkephalin (Table 4). This effect was not due to differences in the antibody isotype, since both the anti-CD9 and anti-CD10 mAb were of the identical (IgG2a) isotype.

TABLE 4

Migration of NALM 6 cells is inhibited by preincubation with anti-CD9 monoclonal antibody.*

| | Monoclonal Antibody | | | |
|---|---|---|---|---|
| [MET-ENK] (nM) | Control (Buffer, alone) | anti-CD10 (IgG2a) (Number of cells at 40 µM)[τ] | anti-CD29 (IgG1) | anti-CD9 (IgG2a) |
| 0.0 | 135 | 160 | 175 | 94 |
| 0.01 | 238 | 354 | 406 | 92 |
| 1.0 | 407 | 510 | 629 | 77 |

TABLE 4-continued

Migration of NALM 6 cells is inhibited by preincubation with anti-CD9 monoclonal antibody.*

| | Monoclonal Antibody | | | |
|---|---|---|---|---|
| [MET-ENK] (nM) | Control (Buffer, alone) | anti-CD10 (IgG2a) (Number of cells at 40 µM)[τ] | anti-CD29 (IgG1) | anti-CD9 (IgG2a) |
| 100 | 637 | 702 | 750 | 60 |

*NALM 6 cells ($10^7$/ml) were preincubated in the migration assay buffer or the buffer containing anti-CD10, -CD29, or CD9 mAb for 30 minutes at 4° C., then pelleted by centrifugation and washed twice in assay buffer prior to their addition to the upper wells of the chemotaxis chamber. The mAb doses used for these studies (1/100 dilution of ascites) were saturating as predetermined by immunofluorescent staining an flow cytometry.
[τ]Assays were as described for FIG. 1. Cells which migrated 40 µm from the origin were identified and scored visually with the use of a fluorescence microscope. The numbers presented are the cell counts determined for 10 hpf × triplicate wells.

Figure 5:
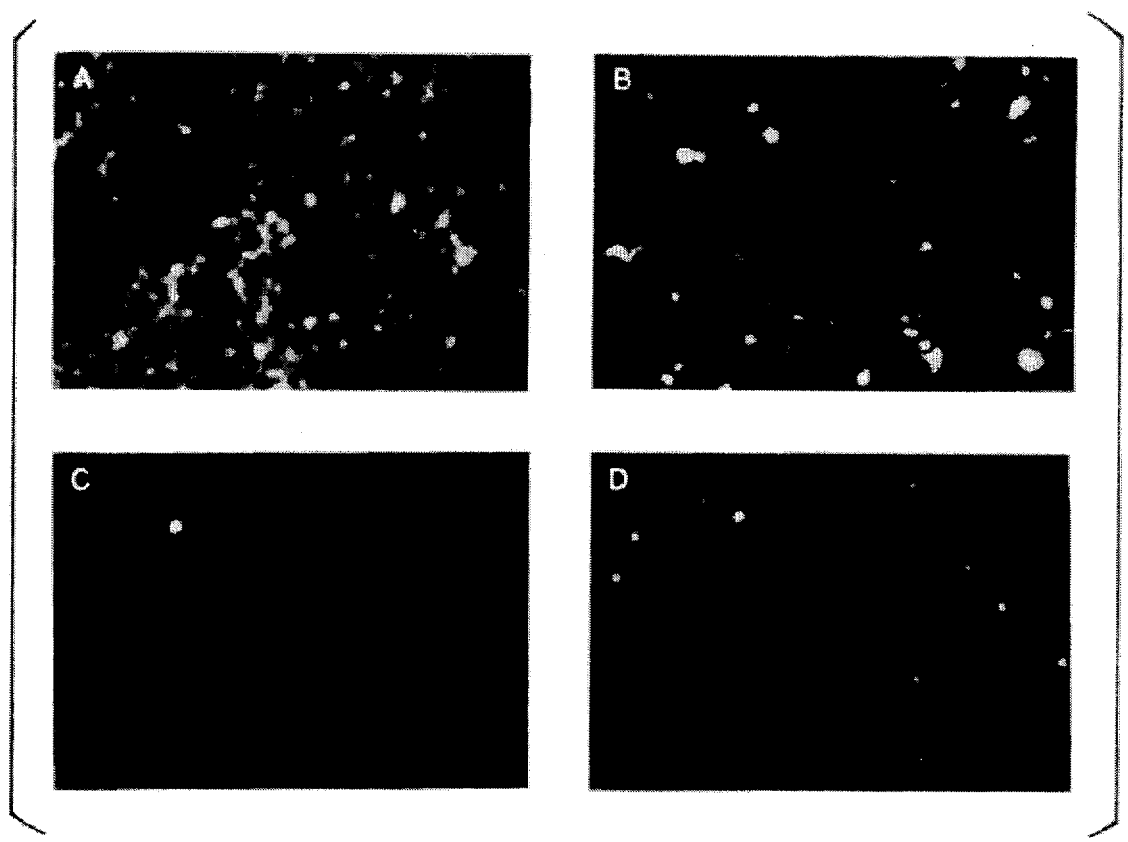
FIG. 5, Panels A-D. Anti-CD9 but not anti-CD10 monoclonal antibody blocks the migration of NALM 6 cells to methionine enkephalin. Nalm 6 cells ($10^7$/ml) were preincubated in the migration assay buffer containing anti-CD9 or anti-CD10 mAb for 30 minutes at 4° C. Migration assays were as described for FIG. 1 and Table 4. Cells were identified for photography with the use of a fluorescence microscope (20x objective). The cells shown in Panel A (at the origin, topside of filter) and Panel C (at 60 µm depth) depict cells preincubated with anti-CD9 mAb. The cells of Panel B (at the origin) and Panel D (at 60 µm depth) were preincubated with anti-CD10 mAb.
Figure 6A:
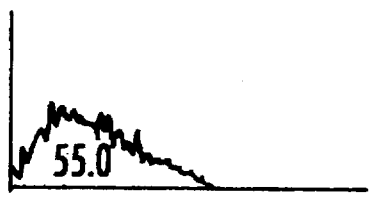
FIG. 6, Panels A-J. Methionine-enkephalin binding to NALM 6 cells is blocked by the opiate receptor antagonist naloxone. MET-ENK (Methionine enkephalin; Sigma Chemical Co.) was labeled with fluorescein isothiocyanate (Molecular Probes, Inc., Eugene, Oreg.) using methods previously employed for labeling other peptides. The reaction mix was applied to a Bio-Gel P2 column (Bio-Rad, Inc., Richmond, Calif.), 0.5 ml fractions collected and screened for binding to NALM 6 cells and the fractions (3–10) which resulted in maximum binding were then pooled and used in subsequent studies for measuring the enkephalin binding sites expressed on cells. The concentrations of fluorescein and MET-ENK (F/P ratio) in the MET-ENK-FITC preparations were measured spectrophotometrically; the F/P ratio was determined to be 1:1.25. In order to label the enkephalin binding sites, cells ($2 \times 10^6$) were suspended in 0.5-ml portions of Hanks Balanced Salt Solution (HBSS) and incubated at 4° C. for 2 h with the concentrations of MET-ENK-FITC indicated (Panels A-H). Enkephalin binding was measured by flow cytometry. Data were collected on a log digital analyzer and mean fluorescence values obtained for distributions of 10,000 cells. Data are shown (Panels A-H) as histograms depicting the fluorescence associated with 10,000 NALM 6 cells; fluorescence channel numbers determined as the means of the distributions are indicated on these panels. Nonspecific binding was measured for duplicate samples which contained 5 µM naloxone in addition to the labeled opioid (see Panel H). Cellular autofluorescence was determined for a sample exposed to buffer, alone (Panel A). In order to determine the number of bound fluorescein molecules the inventors employed fluorescence reference standards (Flow Cytometry Standards Corp., Research Triangle Park, N.C.) for direct quantitation (Panels I & J). In Panel I, the fluorescence intensities of standards were determined in the assay buffer, alone and were for (1) $1.8 \times 10^6$, (2) $4.3 \times 10^5$, and (3) $1.8 \times 10^5$ fluorescein molecules. In Panel J, the standards were analyzed in assay buffer containing 5 µM naloxone. The difference between the standards assayed with (Panel J) or without naloxone (Panel I) was no greater than 2 channels.
Figure 6B:
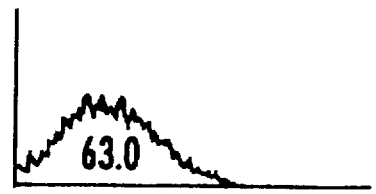
Figure 6C:
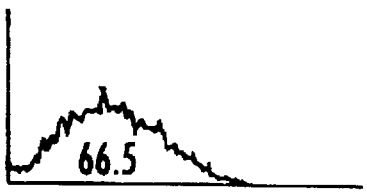
Figure 6D:
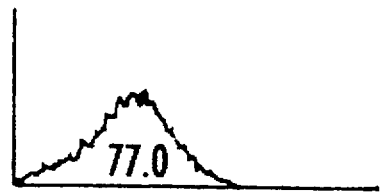
Figure 6E:
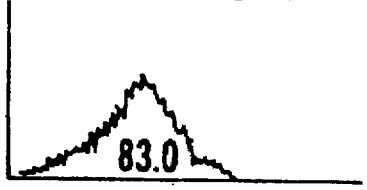
Figure 6F:
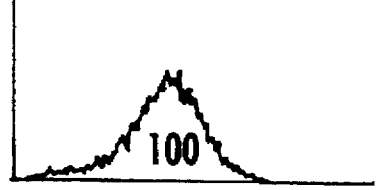
Figure 6G:
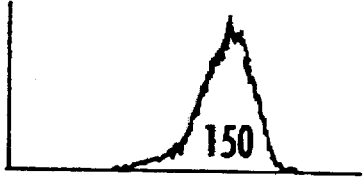
Figure 6H:
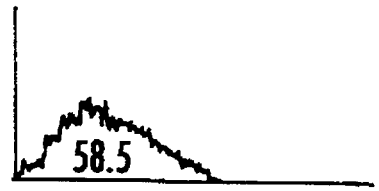
Figure 6I:
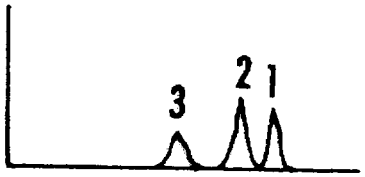
Figure 6J:
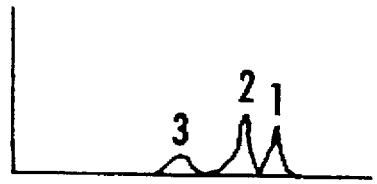

As indicated by the photographs of FIG. 5, the cell group pretreated with anti-CD9 but not CD10 mAb were immobilized at the surface of the filter (FIG. 5). This immobilizing effect was not due solely to anti-CD9 induced aggregations since many non-clumped, single cells also remained immobilized on the topside of the filters (FIG. 5).

D. DISCUSSION

In order to gain a better understanding of factors which regulate the motility of normal and abnormal human B lymphocytes the inventors have investigated the effects of opioid peptides on the migration of cultured B cell lines. The inventors' studies show that the naturally occurring opioid peptide MET-ENK and synthetic enkephalin analogs stimulate the in vitro migration of NALM 6 and LAZ 221 pre-B ALL cells (FIG. 1 and Table 1). Further, the exposure of these pre-B ALL cells to MET-ENK caused a discrete and transient increase in their expression of CD9 molecules (FIG. 3 and FIG. 4). When NALM 6 cells were preincubated with anti-CD9 but not anti-CD10 or anti-CD29 mAb their migration to MET-ENK was markedly diminished (Table 4). It is noteworthy that many human neuroblastomas and lung adenocarcinomas, like the pre-B ALL cells, express both opiate/opioid receptors and the CD9 determinant (Ikeyama et al., 1993; Rubinstein et al., 1993; Ebener, 1990; Komada et al., 1992). Although speculative, it is possible that opioid peptides act as stimulants for the locomotion of these kinds of tumor cells as well as for the leukemia cells. The inventors' findings suggest that at least for some types of leukemia cells the release of endogenous opioid peptides, and possibly, the therapeutic application of analgesics has the potential for affecting their migration and may be relevant in the clinical behavior of such cells.

Previous studies have shown that lymphocyte functions are modulated via classical (naloxone-reversible) and non-classical (naloxone-insensitive) mechanisms (Sibinga and Goldstein, 1988; Gilmore et al., 1990; Heagy et al., 1990). The inventors' data show that the NALM 6 cell chemotactic response to MET-ENK is inhibited by naloxone (Table 2 and FIG. 2). Natural (MET-ENK) and synthetic enkephalins (DADLE and DAMGO) were stimulatory; however, neither the nonanalgesic peptide Des-Tyr-LEU-ENK which is missing the N-terminal Tyr residue common to all endogenous analgesic peptides nor the neutrophil chemotactic peptide FMLP stimulated the migration of these pre-B ALL cells (Table 1). The inventors' findings suggest that the pre-B ALL cell migration to enkephalins is mediated via opiate/opioid receptors belonging to the same family of receptors expressed in the CNS.

The endogenous opioid peptides are rapidly inactivated in vivo (Paternak, 1993), and therefore, probably only briefly available for signaling to circulating leukocytes. The implications are that low doses of these peptides probably elicit a rapid cellular response which then serves to orient and direct the responding leukocyte toward the reaction site (i.e., source from which the peptide was released). It is of note that the LAZ 221 and NALM 6 pre-B ALL cells express a cell surface enzyme which hydrolyzes and inactivates the enkephalins (enkephalinase; neutral endopeptidase; CD10) (Shipp et al., 1990). This enzyme probably modulates their response to MET-ENK by either decreasing the effective concentration in the surrounding medium or down regulating the response. Local release of the opioid peptides has been difficult to quantitate because of the rapid rate at which these peptides are hydrolyzed; however, concentrations as great as $10^{-10}$M have been measured for brain tissues (Wardlaw et al., 1980). The inventors' data show that a MET-ENK dose of $10^{-11}$M which is less than the endogenous level attained in the CNS (i.e., $10^{-10}$M) stimulates the migration of NALM 6 and LAZ 221 pre-B All cells (FIG. 1).

In previous studies the inventors have shown that the addition of MET-ENK to NALM 6 cells induces a rapid rise in [$Ca^{2+}$]i; only a brief (~30 sec) lag phase preceded this response (Heagy et al., 1992). In these studies the inventors show that MET-ENK is swift acting; within five minutes of exposure to MET-ENK the NALM 6 cells underwent a morphological response (i.e., flattening and spreading) (FIG. 2). Light microscopic and electron micrograph analyses of PMNs responding to β-END or other chemotactic factors has shown that these cells undergo a series of rapid morphological responses including elongation and flattening (Falke and Fischer, 1985). The onset of the PMN morphological response to β-END was ≦2 minutes (Falke and Fischer, 1985). In these studies the inventors' document that for the NALM 6 cells only a brief exposure (≦5 minutes) to MET-ENK is sufficient for activation of responses (FIG. 2).

The inventors' data shows that the morphological response of NALM 6 cells to MET-ENK correlated with an increase in cell surface area (i.e., increase in forward and right angle light scatter) (FIG. 2). Interestingly, exposure of the NALM 6 cells to naloxone, alone shifted the baseline light scatter below that measured for the control (cells maintained in PBS alone). (FIG. 2). The significance of this light scatter response is unknown. The viability of the naloxone-treated and nontreated cells was equivalent (≧96%); therefore, naloxone was not nonspecifically cytotoxic. Other investigators have reported that naloxone inhibits the growth of some tumor cells (Zagon and McLaughlin, 1987; Maneckjee and Minna, 1992); however, the inventors have cultured NALM 6 cells with 10 μM naloxone for two weeks without any effect on their viability or doubling time (data not shown).

In these studies the inventors show that MET-ENK is a stimulus for the migration of NALM 6 and LAZ 221 (pre-B ALL) but not LAZ 388 (mature, EBV-transformed) cells (Table 1). The responsive LAZ 221 and unresponsive LAZ 388 cell lines were derived from one individual (Shipp et al., 1989), and therefore have the same genetic background. The migration of the pre-B ALL but not EBV-transformed cells to MET-ENK may be related to differences in their developmental or activation state. B cell differentiation and activation is a complex, multistep process regulated by factors in the cellular environment and a coordinated, sequential expression of specific cell surface receptors (i.e., differentiation/activation antigens) (Zola et al., 1989; Nilsson and Klein, 1982). It is possible that the LAZ 338 cells fail to migrate to MET-ENK simply because this enkephalin does not bind to the cells. This possibility is consistent with previous studies using EBV transformed cells. Other studies have identified $^{125}$I-β-END binding sites that recognize the unique carboxyl terminus of this peptide but not the N-terminal pentapeptide sequences of MET-ENK (Borboni et al., 1989). It is known that EBV- transformation renders cells unresponsive to normal activation signals (Nilsson and Klein, 1982) and it is possible, therefore, that the LAZ 388 cells are insensitive to MET-ENK by virtue of their transformation by EBV.

Previous studies have shown that the addition of anti-CD9, -VLA β1, -VLA α4, or -VLA α5 mAb to NALM 6 and other pre-B ALL cells induces the formation of homotypic cell clusters (Letarte et al., 1993). The physiological significance of such homotypic aggregations is unknown. Previously, Letarte et al (Letarte et al., 1993) analyzed a panel of pre-B-ALL cell lines for aggregation as well as their expression of many adhesion molecules. These studies led to the conclusion that the level of CD9, but not CD11a, CD18, CD19, CD44, or CD54 molecules correlated with cell adhesion (i.e., the level of homotypic aggregation) (Letarte et al., 1993). In this report the inventors show that the activation of NALM 6 or LAZ 221 cells with MET-ENK correlates with an increase in their migration (FIG. 1) and expression of CD9 (FIG. 3 and FIG. 4). The initial events in cell migration have been associated with the activation of adhesion molecules (Hemler, 1990; Springer, 1990). The inventors' findings, therefore, provide new evidence linking CD9 expression with a physiological function (cell migration) that has been shown to involve the activation of adhesion molecules.

In this study the inventors show that the preincubation of NALM 6 cells with anti-CD9 mAb inhibits their migration to MET-ENK (Table 4). This is the first report suggesting that CD9 molecules may be important in the regulation of lymphoid cell migration to chemoattractants. Previously, Miyake et al (Miyake et al., 1991) showed that the spontaneous phagokinetic tract motility of cultured human lung and gastric cancer cells was decreased by exposure to anti-CD9 mAb. In other studies (Ikeyama et al., 1993) the spontaneous motility of human or rodent tumor cells was decreased when the cells were transfected with human CD9 cDNA. All together, these findings suggest that CD9 may play an important role in the locomotion (directed and random) of many kinds of cells. There are several possible mechanisms by which CD9 may regulate cell movement. One possibility is that CD9 is instrumental in down regulating the motile response. When added to platelets anti-CD9 mAb initiate transmembrane signals involving phosphatidylinositol metabolism and protein-tyrosine phosphorylation (Yatomi et al., 1993). The activation of CD9 molecules may, via such intracellular signals, render cells refractory to the effects of additional second messengers (e.g., cAMP, $[Ca^{2+}]_i$) which are essential in other events (e.g., cytoskeletal and membrane reorganization) that take place in moving cells. If this is the case the activation of CD9 molecules may deliver negative signals that serve as a brake on cell motility.

A second plausible mechanism by which CD9 may regulate cell motility is related to the role of this transmembrane protein in adhesion. Cells move over various surfaces (e.g., membranes, culture dishes or other cells) via a series of coordinated attachments (adhesions) and detachments from the surface (Shimizu et al., 1992;Springer, 1990). Previous studies (Letarte et al., 1993; Forsyth, 1991; Slupsky et al., 1989) have shown that the antibody induced activation of CD9 molecules expressed on platelets, pre-B leukemia cells or endothelial monolayers increases the adhesion-related function(s) of these cells. It is possible that CD9 molecules participate in the transient adhesions (attachments) which mediate cell locomotion. Anti-CD9 mAb inhibit the movement of NALM 6 cells (Table 4) and lung tumor cells (Miyake et al., 1991) probably by blocking cell attachment to the substrate. Miyake et al (Miyake et al., 1991) reported that transfection of various kinds of tumor cells with human CD9 cDNA resulted in an overexpression of surface CD9 molecules and a decrease in motility. This observation is consistent with the notion that CD9 functions in the attachment processes which underlie cell motility. It is plausible that such increased expression of CD9 results in a strengthening of the forces which fasten cells to their substrate. Further, such overexpression of CD9 molecules may prolong the duration of the attachment process, and consequently, impair or retard the onset of the detachment process. Since cell locomotion is implemented by a series of attachments (transient adhesions) and detachments any event which blocks or delays the detachment process will also diminish cell movement.

Moreover, it is conceivable that CD9 molecules facilitate adhesions, however their release from the cell surface may be essential for detachment, and therefore, for locomotion. Previous studies (Forsyth, 1991) have shown that the activation of cultured endothelial cells with an anti-CD9 mAb results in a transient increase in their binding of neutrophils. This effect waned in parallel with the shedding of CD9 molecules from the activated endothelial cells until at 60 minutes the cellular expression was reduced below the detectable level (Forsyth, 1991). The inventors' studies show that the MET-ENK induction of CD9 molecules on NALM 6 cells is transient and declines by 120 minutes (FIG. 4). It is noteworthy that the presence of soluble CD9 antigen in cerebrospinal fluid, presumably shed from migrating leukemic cells, has been identified as an early diagnostic marker for CNS leukemia (Komada et al., 1992). Possibly, the release of CD9 molecules from cell membranes facilitates transmembrane migration.

How CD9 promotes or strengthens adhesions is unclear. There are no known physiological ligands which bind to CD9. Possibly, CD9 plays a direct role in adhesion (e.g., bridge-building between cells) or alternatively, it may act as a trigger for the activation of other adhesion-forming molecules (e.g., HLA-DR, GPIIb/IIIa). CD9 as well as the structurally-related transmembrane proteins TAPA-1 and M33 have been shown to form multimeric complexes with known adhesion and other kinds of cell surface receptors (Slupsky et al., 1989; Komada et al., 1992; Imai and Yoshie, 1993; Seehafer and Shaw, 1991; Mitamura et al., 1992). TAPA-1, like CD9, has been implicated in B cell adhesion-dependent processes (Bradbury et al., 1993) and TAPA-1 as well as M33 are thought to participate in the formation of HTLV-1 induced T cell syncytia (Imai and Yoshie, 1993). Studies have shown that the TAPA-1 molecules expressed on B cells form multimeric complexes with Leu 13, CD19 and HLA-DR determinants (Bradbury et al., 1993) and those on T cells associate with the M33 and CD4 or CD8 antigens (Imai and Yoshie, 1993). It has been reported that the activation of platelets with anti-CD9 mAb results in the association of CD9 with the b-3 integrin receptor GPIIb/IIIa (Slupsky et al., 1989) and with small GTP binding proteins (Seehafer and Shaw, 1991). The full significance of such supramolecular complexes is not understood but they may be involved in transmembrane signal transduction and the activation of cell surface receptors or adhesion-strengthening events (Imai and Yoshie, 1993; Bradbury et al., 1993).

The role of CD9 in the normal development and function of lymphoid populations is unknown. Early pre-B progenitor cells are distinguished from mature B lymphocytes by their high expression of CD9 and CD10 determinants, and it is possible, that these molecules are involved in developmental processes. The pre-B progenitor cells are mostly found in bone marrow in the peripheral subendosteal area of the parenchyma and decline in number near the bone center (Hermans et al., 1989). It has been suggested that during the course of development within the bone marrow B cell progenitors migrate along a radial developmental sequence (Zola et al., 1989; Hermans et al., 1989). B cell maturation and entry into peripheral circulation is accompanied by a down-regulation in both CD9 and CD10 determinants. Possibly, the CD9 and CD10 molecules expressed on progenitor B lymphocytes regulate their adhesion and migration, and in this way, direct their passage down the developmental gradient.

Stress-states may be harmful to health by acting on a number of systems or via multiple pathways. It is now recognized that a complex set of networks interconnect the sympathetic and parasympathetic nervous, immune and endocrine systems (Cunnick et al., 1992). Lymphoid organs including the thymus, lymph nodes and lymphoid tissues, spleen and bone marrow receive noradrenergic sympathetic or cholinergic parasympathetic innervation (Felten et al., 1987). Studies have shown that factors arising from the hypothalmic-pituitary-adrenal (HPA) axis including adrenocorticotropic hormone, glucocorticoids, epinephrine and opioid peptides modulate immune functions and that via a feed-back loop the cytokines released from immune cells regulate pituitary and hypothalamic functions (Cunnick et al., 1992). Stress-responses correlate with the release of hormones (e.g., opioid peptides) which have potent immunomodulatory activities (Sibinga and Goldstein, 1988; Gilmore et al., 1990). It is possible, therefore, that stress-associated hormonal factors influence host resistance to disease via immune modulation.

Opioid peptides may exert direct as well as indirect (i.e, via immune modulation) effects on metastatic processes. Previously, opioid peptides have been shown to modulate the growth of some cultured human lung carcinomas (Maneckjee and Minna, 1992). In this report the inventors have identified the endogenous opioid peptide MET-ENK as a stimulus for the in vitro migration of NALM 6 and LAZ 221 pre-B ALL cells. The inventors' findings confirm the existence of functional enkephalin receptors on leukemia cells and provide additional clues to the mechanisms by which opioid peptides may exert effects on normal and abnormal lymphoid cells.

EXAMPLE 4

Human T and B Cells Bind Opiate Receptor Agonists

Immunosuppression mediated by opiates and opioid peptides probably results, at least in part, via a direct interaction with lymphocytes; however, little attention has been given to the type receptors or signaling events which underlie lymphocyte responses to these agents. For the purpose of identifying and characterizing opiate/opioid receptors on lymphoid cells the inventors have prepared and utilized a fluorescein derivative of the physiological opioid pentapeptide methionine enkephalin. The inventors assessed the binding of this fluorescein-tagged peptide to NALM 6 (B cell leukemia) and Jurkat (T cell leukemia cell) lines with the use of flow cytometry. Specific, saturable binding was demonstrated and multiple forms of opiate/opioid receptor were identified. Two enkephalin binding sites (high and low affinity) with Kd of 1.01 and 318 nM, corresponding to $7.77 \times 10^3$ and $4.48 \times 10^4$ sites, respectively, were measured for the NALM 6 cells and $9.0 \times 10^2$ high affinity (Kd, 1.36 nM) and $3.0 \times 10^4$ low affinity (Kd, 181 nM) sites/cell were identified for the Jurkat line.

Similar findings were obtained when $^3$H-naloxone and conventional radioligand-receptor filtration assays were employed to measure the opiate binding sites expressed by NALM 6 and Jurkat cells. Nonlinear regression analyses of the data obtained with $^3$H-naloxone was best fit by the two-site model. Kd of 4.7 nM and 230 nM, ($3.3 \times 10^4$ and $1.75 \times 10^5$ sites, respectively) were measured for NALM 6 cells and $8.67 \times 10^2$ high affinity (Kd, 2.99 nM) and $1.82 \times 10^4$ low affinity (Kd, 125 nM) naloxone binding sites/cell were identified for Jurkat cells.

Synthetic opiate receptor agonists selective for δ- and κ-type opiate receptors were employed for identifying opiate/opioid receptor types expressed by the leukemia cells. Receptors of the δ- type were labeled with $^3$H-DADLE and the highly selective $\Delta_{-1}$ subtype selective ligand $^3$H-DPDPE. The κ-receptor (κ$_{-1}$ subtype) agonist $^3$H-U69,593 was used for identifying κ-type sites expressed on the leukemia cells. Specific, naloxone-reversible binding was measured with these opiate receptor ligands suggesting that the NALM 6 and Jurkat cell lines express classical opiate/opioid receptors of the δ and κ types.

Receptor-mediated $Ca^{2+}$ signaling is thought to be an important mechanism for regulating lymphocyte functions. When applied to Jurkat cells the endogenous opioid methionine enkephalin as well as synthetic and highly selective opiate receptor agonists stimulated rapid increases in $[Ca^{2+}]i$. These studies provide additional evidence for the existence of functional opioid/opiate receptors on lymphocytes and suggest that the effects of opiates and opioids on lymphoid cells are mediated via receptor-mediated $Ca^{2+}$ signaling. Further, the identification of opiate/opioid receptors on these leukemic cells raises the possibility that opiates and endogenous opioid peptides exert direct effects on such abnormal cells, and may, therefore, have relevance in oncogenesis.

In addition to having analgesic activity, opioid peptides are important participants in the regulation of autonomous functions, animal behaviors, hormone and neurotransmitter release and the immune response (Fischer, 1988; Sibinga and Goldstein, 1988; Gilmore et al., 1990; Heijnen et al., 1991). These peptides may play a crucial role in regulating the body's resistance to infectious and oncogenic diseases. Opiate addiction and stress have been linked with immune depression (Fischer, 1988; Sibinga and Goldstein, 1988; Gilmre et al., 1990; Heijnen et al., 1991). Secretion of the opioid peptides β-endorphin (β-END) and methionine enkephalin (MET-ENK) correlates with diurnal rhythms, physical activities, and stressful stimuli (Fischer, 1988; Sibinga and Goldstein, 1988; Gilmre et al., 1990; Heijnen et al., 1991). In animal studies the in vivo administration of opiates or MET-ENK has been shown to diminish immune function (Chao et al., 1990; Bryant et al., 1988; Taub et al., 1991). Opiate addiction has been documented to result in an increased susceptibility to opportunistic and bacterial infections and malignant diseases (Novick et al., 1989). Evidence obtained in vivo in animal models and in vitro with isolated human and rodent cells has shown that opiates and MET-ENK diminish NK cell activity, decrease lymphocyte proliferation, and inhibit antibody production (Fischer, 1988; Sibinga and Goldstein, 1988; Gilmore et al., 1990). Taken together, these findings have led a number of investigators to suggest that the stress induced release of opioid peptides is related to the effects of stress on the immune system (Fischer, 1988; Sibinga and Goldstein, 1988; Gilmore et al., 1990).

The binding of opiates to classical opiate receptors within the CNS is blocked by antagonists such as naloxone (Pasternak, 1988). Analgesic peptides including the enkephalins, endorphins, and dynorphins bind to these receptors as well as to other naloxone insensitive sites (Pasternak, 1988). The synthesis and use of a large panel of synthetic opiate agonists and antagonists has led to the recognition of distinct opiate receptor types (e.g., δ, μ, κ) and subtypes (e.g., δ$_{-1}$, μ$_{-1}$, μ$_{-2}$ κ$_{-1}$, κ$_2$) (Pasternak, 1988; Traynor and Elliott, 1993). Endogenous opioid peptides interact with more than one of the δ, μ, and κ sites (Pasternak, 1988; Traynor and Elliott, 1993; Corbett et al., 1984). The issue of opiate receptor multiplicity is complex and multiple receptor subtypes are expressed on single neurons (Pasternak, 1988; Traynor and Elliott, 1993). Some recent studies have suggested the existence of cross-talk or cooperation between certain of the receptor-subtypes. For example, sub-antinociceptive doses of the synthetic and highly selective δ-opioid receptor agonist DPDPE ([D-Pen$^{2,}$ $^5$]enkephalin) enhance the antinociception mediated via the opiate μ-receptor agonist morphine (Traynor and Elliott, 1993; Porreca et al., 1992).

Some evidence suggests that lymphocytes express classical (naloxone-sensitive) opiate/opioid binding sites (Madden et al., 1987; Carr et al., 1988; Radulescu et al., 1991; Heagy et al., 1990; Heagy et al., 1992); however, little is known concerning the receptor types or subtypes expressed by immune cells. $^3$H-naloxone which binds to μ, δ, and κ type opiate receptors has been shown to label human peripheral blood T cells (Madden et al., 1987). Isolated T and B lymphocytes have been reported to bind synthetic δ- and μ-selective opiate receptor ligands (Carr et al., 1988; Radulescu et al., 1991) and human peripheral blood T cells have been documented to express functional receptors of the δ and μ types (Heagy et al., 1990). Previously, the inventors (Heagy et al., 1990) have shown that opiate receptor agonists with selectivity for δ or μ receptors are potent stimulants for the migration of human T cells. In addition, the inventors (Heagy et al., 1992) have identified functional κ and μ type receptors on cultured B cell lines. When applied to the B cells, opiate receptor agonists selective for κ or μ60 receptors stimulated transmembrane $Ca^{2+}$ signaling.

The inventors have recently shown that physiologic concentrations of MET-ENK stimulate the migration of pre-B acute lymphoblastic leukemic (ALL) cell lines. The effects of MET-ENK on the migration of such pre-B leukemia lines correlated with a transient upregulation in surface expression of CD9, a leukemia cell marker thought to be important in the adhesive processes of these cells. Factors which may contribute to the clinical behavior and pathology of leukemias need further study. In order to define and characterize opiate/opioid receptors on lymphoid cells and to gain a better understanding of how opiates and opioid peptides may influence leukemic processes, the inventors have initiated studies to identify the opiate receptors expressed on cultured leukemia lines. For these studies the inventors have used cultured Jurkat (T cell leukemia) and NALM 6 (pre-B lymphoblastic leukemia) cell lines.

In order to identify and measure opiate/opioid receptors which recognize physiological opioid peptides the inventors have prepared a fluorescinated derivative (Bender et al., 1987) of the naturally occurring enkephalin pentapeptide MET-ENK (MET-ENK-FITC). For labeling the enkephalin binding sites expressed on Jurkat and NALM 6 cells the inventors incubated the cells ($2\times10^6$) in 0.5 ml portions of Hanks balanced salt solution (HBSS) containing doses of 2.5 to 400 nM MET-ENK-FITC for periods of 2 hours at 4° C. The inventors used flow cytometry for measuring cell-associated fluorescein (FIG. 6). The amount of specific binding (i.e., bound MET-ENK-FITC which was displaced in the presence of unlabeled agent) was measured using 5 μM unlabeled MET-ENK or 5 μM naloxone. The inventors' findings with the unlabeled enkephalin and the opiate receptor antagonist were equivalent.

Figure 7A:
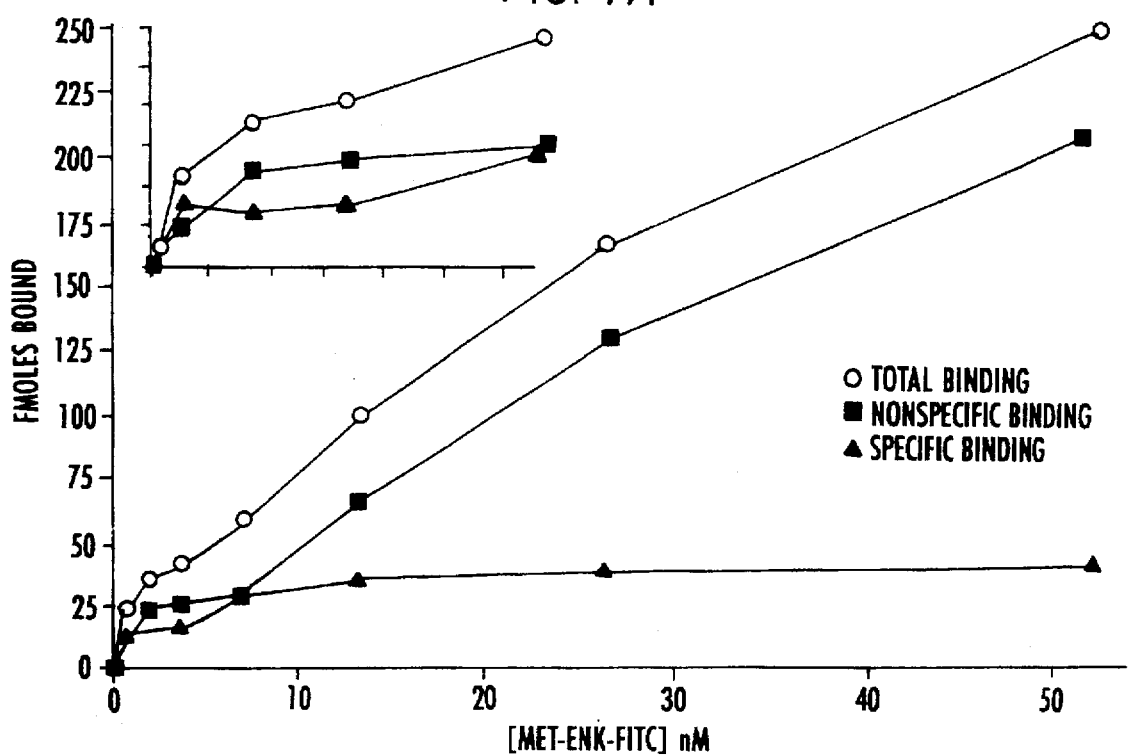
FIG. 7, Panel A with Inset and Panel B with Inset. Binding isotherms generated from flow cytometric analysis of MET-ENK-FITC equilibration with NALM 6 and Jurkat cells. Data are plotted as the concentration of MET-ENK-FITC in the samples (x-axis) vs cell bound MET-ENK-FITC (y-axis). The total binding represents the amount measured for samples incubated with MET-ENK-FITC, alone. Nonspecific binding was determined as the residual measured in the presence of 5 µM unlabeled MET-ENK. Specific binding was determined as the difference between the total and nonspecific binding components. Samples were incubated at 4∞ C in $Ca^{2+}$, $Mg^{2+}$ deficient HBSS supplemented with 1 µM thiorphan (enkephalinase inhibitor) and 0.2% sodium azide. Cells ($2 \times 10^6$) were incubated for 2 h with the indicated concentrations of MET-ENK-FITC, or with this conjugate and 5 µM unlabeled MET-ENK, and then analyzed directly in the reaction mixture. Fluorescence channel numbers expressed as means for the distributions were used to determine the concentrations of bound fluorescein. The number of fluorescein molecules associated with the cells was read from calibration curves prepared from standard fluorescent reference beads; the standards ranged from 0 to $1.8 \times 10^6$ fluorescein molecules per bead. The values read from the standard curves were corrected for autofluorescence and for an F/P ratio of 1:1.25. The moles of bound label in each sample were obtained by multiplying the number of bound molecules times the total number of cells in the sample and then dividing by Avogadro's number. Panel A, MET-ENK-FITC binding to NALM 6 cells. Panel B, MET-ENK-FITC binding to Jurkat cells. The insets depict the binding measured over the range of 0.33 and 6.8 nM MET-ENK-FITC.
Figure 7B:
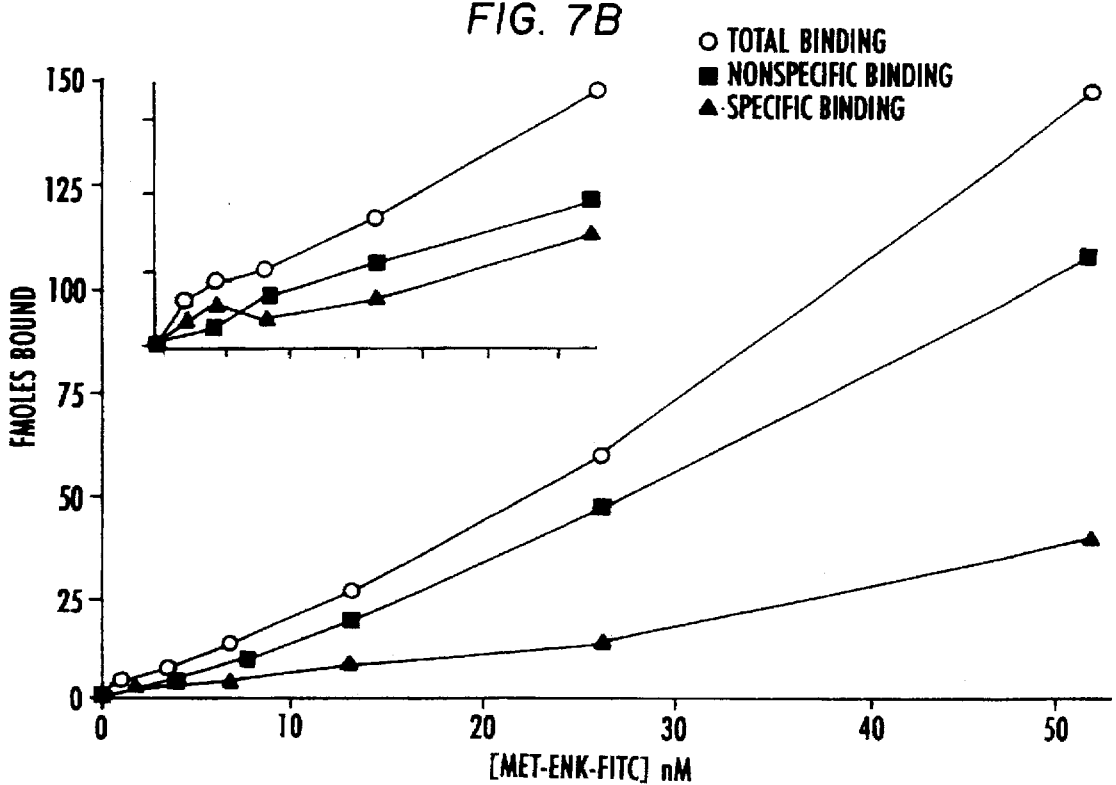

Representative binding isotherms generated from MET-ENK-FITC equilibration with the leukemia cells are presented in FIG. 7. When the binding data obtained in these studies were corrected for specific binding, transformed and subjected to Scatchard analysis the resulting plots were curvilinear indicating the presence of more than one kind of opioid/opiate binding site.

Further analysis of data using nonlinear regression analysis and the Ligand Computer Program described by Rodbard and Munson (Munson and Rodbard, 1980) showed that the Scatchard plots could be resolved into two linear components. (Scatchard plots representative of the data generated in our analysis of MET-ENK binding to the Jurkat cells are presented in FIG. 8, Panels A & B.). These findings suggest that the cells express multiple types (high and low affinity forms) of the enkephalin receptors. The Kd measured for MET-ENK binding to Jurkat cells were 1.36 and 181 nM; the high affinity sites were measured at $3.3\times10^{-12}$M ($9\times10^2$ receptors/cell) and the greater number of low affinity sites were measured at $1.01\times10^{-10}$M ($3.3\times10^4$ sites/cell) The Kd measured for MET-ENK binding to NALM 6 cells were 1.01 and 318 nM; the number of the higher affinity sites was measured at $2.59\times10^{-11}$ M ($7.77\times10^3$ sites/cell) and those with lower affinity were at $1.49\times10^{-10}$M ($4.48\times10^4$ sites/cell). These studies show that Jurkat and NALM 6 cells express binding sites with high affinity for the endogenous opioid peptide MET-ENK. Further, since in the presence of naloxone this association is decreased, indicating competition between the peptide and the opiate receptor antagonist, these studies suggest that the enkephalin binding sites are of the classical type (naloxone-sensitive). These findings are novel in that they measure naloxone-reversible binding of a naturally occurring opioid peptide to lymphoid cells. Previous studies have focused on the binding of the endogenous polypeptide β-END to freshly isolated lymphocytes and Epstein-Barr virus (EBV) transformed cell lines (Borboni et al., 1989). The binding of β-END to these kinds of lymphocytes was found to be insensitive to naloxone and not displaced by synthetic peptides containing MET-ENK residues (TYR-GLY-GLY-PHE-MET). Taken together, the data point to the conclusion that cells of the immune system, like those of the nervous system express multiple, both classical and non-classical (naloxone-sensitive and insensitive) opiate/opioid binding sites. Within the CNS the issue of opiate receptor multiplicity is complex and the findings suggest this is likely to be the case in the immune system.

Figure 9A:
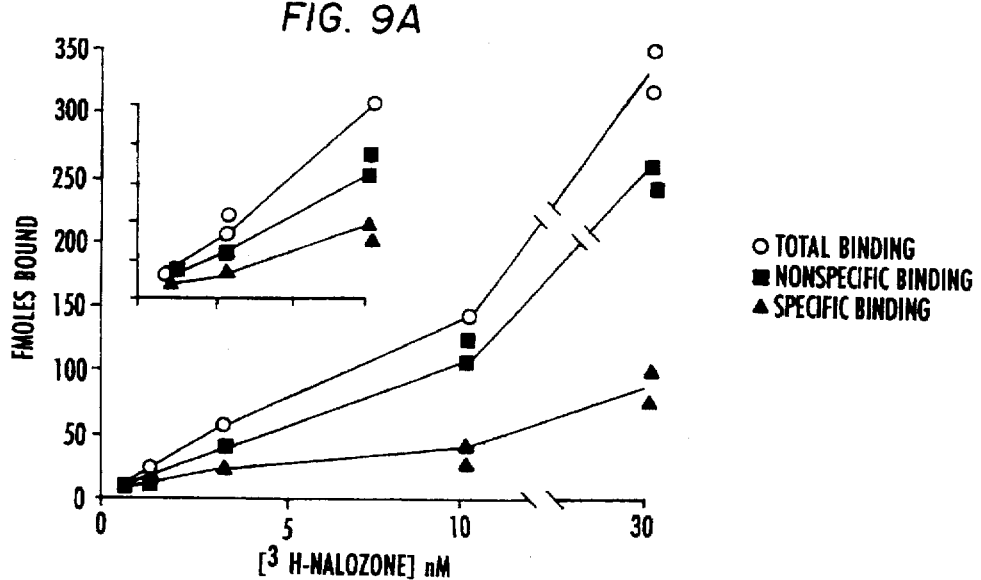
FIG. 9, Panels A-C. $^3$H-Naloxone binds to NALM 6 cell membranes. Data are plotted as the concentration of $^3$H-Naloxone (x-axis) added to the samples vs membrane bound $^3$H-Naloxone (y-axis). The total binding represents that measured for samples incubated with $^3$H-Naloxone, alone. Nonspecific binding was determined for a replicate set of samples which also contained 50 µM unlabeled naloxone. Specific binding was measured as the difference between the total and nonspecific binding components. Each data point represents the mean for triplicate samples. In Panel A, NALM 6 cell membranes were incubated on ice in 200 µl of 5 mM Tris-HCl buffer containing 0.32M sucrose, and 100 mM phenylmethylsulfonylfluoride (PMSF), pH 7.2 and the indicated concentrations of $^3$H-Naloxone (x-axis) for 4.5 h. The data of Panel A were obtained in 2 separate assays. The binding measured for $^3$H-Naloxone doses ranging between 0.33 and 3 nM is shown in the inset. In Panel B, the binding assay buffer also contained 10 mM $CaCl_2$ and in Panel C, 10 mM $MgCl_2$. Assays were carried out in 96-well polypropylene microtiter plates (Costar Corporation; Cambridge, Mass.). Each assay well contained the membrane equivalent of $5 \times 10^6$ cells. Following incubation, the membranes were transferred to Whatman GF glass fiber filters, washed with three 3-ml portions of binding assay buffer, dried and then counted in a liquid scintillant. The membranes used in these studies were prepared as previously described (Ott and Herz, 1989). Cells were harvested from culture in $Ca^{2+}$ and $Mg^{2+}$ deficient PBS, washed, resuspended in 50 mM Tris-HCl (pH 7.4), and frozen at –70° C. Frozen cell pellets (–70° C.) were thawed in 5 mM Tris-HCl (pH 7.4, 20° C.), containing 1 mM EGTA and then sonicated. The sonicate was centrifuged at 1,000 g for 10 m, the supernatant removed, and then centrifuged for an additional 20 m at 28,000 g. This pellet ($P_2$) was resuspended in 50 mM Tris-HCl containing 100 mM EGTA, 80 v/v glycerol, pH 7.4 and stored at –70° C. until used in the binding assays.
Figure 9B:
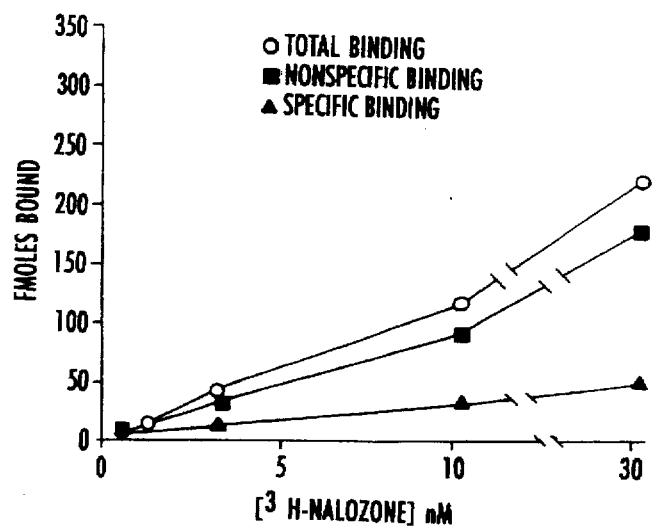
Figure 9C:
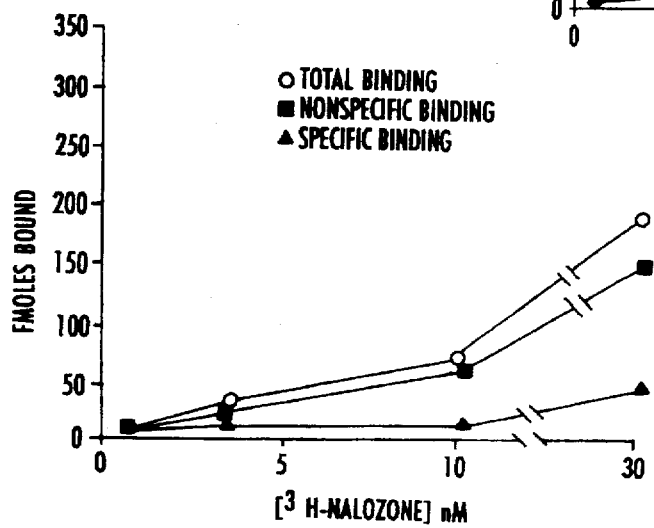

In order to further define the enkephalin-receptors expressed on Jurkat and NALM 6 cell membranes the inventors measured the binding of $^3$H-Naloxone ([N-Ally-2,3-$^3$H]Naloxone; Amersham Corporation; Arlington Heights, Ill.) to cell membranes prepared from the cells. A P2 (Ott et al., 1989) membrane fraction which the inventors prepared (see FIG. 9) and stored in 50 mM Tris-HCl with 1 mM EDTA and 8% v/v glycerol, pH 7.5 at −70° C. was used for these studies. The inventors incubated the membranes with $^3$H-Naloxone in 200 μl of a standard 5 mM Tris-HCl buffer containing 0.32M sucrose and 100 μM phenylmethylsulfonylfluoride (PMSF), pH 7.2 in 96-well polypropylene microtiter plates (Costar Corporation; Cambridge, Mass.). Each microtiter well contained the membrane equivalent for $5\times10^6$ cells. Following the incubations, nonbound $^3$H-Naloxone was separated from the membranes by rapid filtration on Whatman GF/F filters (Fischer Scientific; Pittsburgh, Pa.) and 3 washes with 3-ml portions of ice cold buffer. Liquid scintillation counting was used to measure the amount of $^3$H-Naloxone which bound to the samples. Specific binding was measured as the difference between total and nonspecific counts (i.e., the label associated with samples which were incubated with 50 μM unlabeled naloxone in addition to the labeled antagonist). The specific binding measured for concentrations of $^3$H-Naloxone between 0.3 to 3.0 nM was ~38 to 43% of the total label added to the wells. (Representative data are shown in FIG. 9, Panel A and FIG. 10, Panels A & B). Despite the fact that divalent cations have been reported to increase specific binding to the classical opiate receptors on nervous tissue (Change et al., 1978), the addition of 10 mM $MgCl_2$ or $CaCl_2$ to our standard 5 mM Tris buffer did not improve the level of specific $^3$H-Naloxone binding to NALM 6 cell membranes (FIG. 9, Panels B & C). The inventors, analysis of the association of $^3$H-Naloxone with NALM 6 membranes showed that for samples incubated at 20° C. a 4-hour incubation was sufficient to reach equilibrium conditions; the specific binding measured for 5 nM $^3$H-Naloxone at 4 hours was 42% of total which then decreased to 37% following an additional 18 hour incubation (data not shown).

Figure 11A:
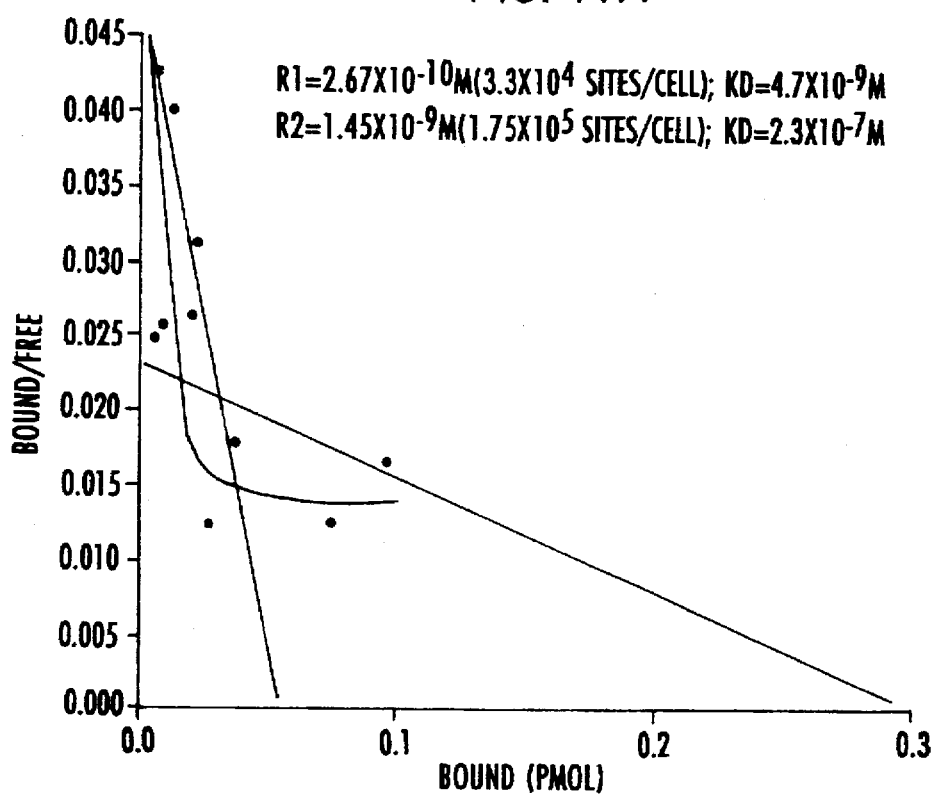
FIG. 11, Panels A and B. The opiate receptor antagonist naloxone binds to two (high and low affinity) sites on leukemia cells. When data obtained from the binding assays with $^3$H-Naloxone were replotted in Scatchard plots (bound label on the x axis vs the ratio of bound to free naloxone on the y axis) the resultant curves were nonlinear, asymptotically approaching a horizontal line. Nonlinear regression analysis performed with the aid of the Ligand Computer System (Munson et al., 1984) revealed two linear components and showed that the data best fit a two site model. Panel A, Scatchard analysis of $^3$H-Naloxone binding to NALM 6 cell membranes. Data presented were obtained in 2 separate experiments with NALM 6 cell membranes. Panel B, Scatchard analysis of $^3$H-Naloxone binding to Jurkat cell membranes. Data presented were obtained in 2 separate experiments with Jurkat cell membranes.
Figure 11B:
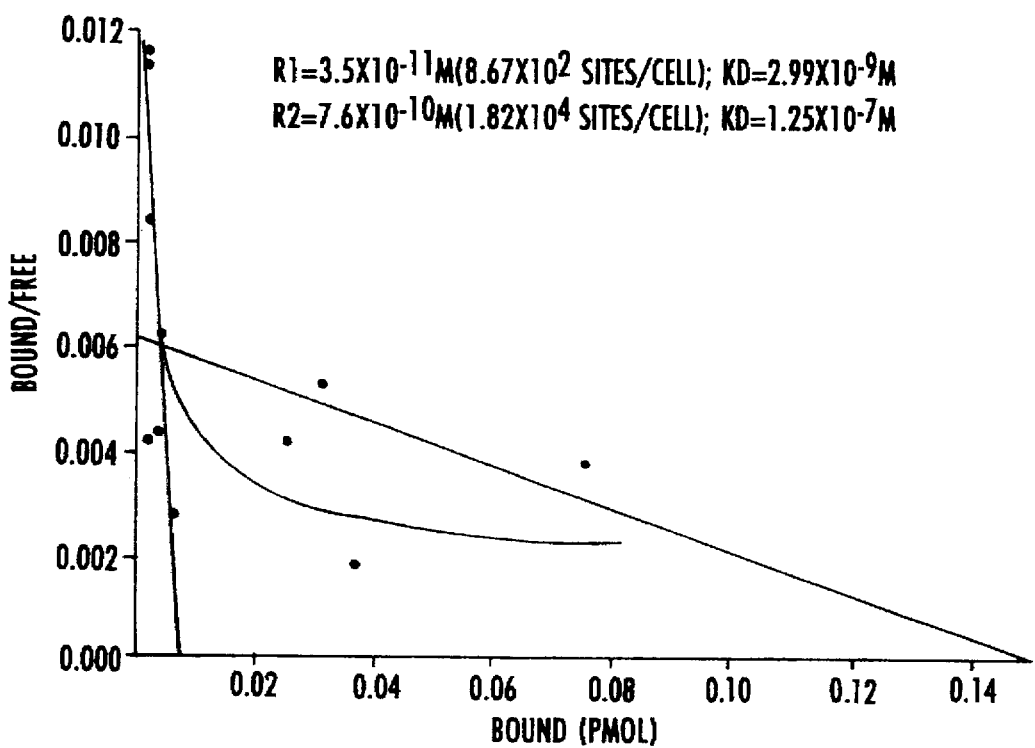

The Scatchard plots depicting $^3$H-Naloxone binding to the NALM 6 and Jurkat cells were reminiscent of those constructed from the data obtained with our MET-ENK-FITC conjugate; these plots were also curvilinear (FIG. 11, Panels A & B) and nonlinear regression analyses indicated the data to best fit the two-site model. The Kd measured for $^3$H-Naloxone binding to Jurkat cells were 2.99 and 125 nM; these studies measured 8.67×10$^2$ high affinity sites and 1.82×10$^4$ low affinity sites/cell (FIG. 11). For NALM 6 cells the Kd were measured at 4.7 and 230 nM and 3.3×10$^4$ high affinity and 1.75×10$^5$ low affinity sites/cell were detected (FIG. 11, Panels A & B). These studies provide additional evidence for the expression of multiple opiate/opioid receptor types (high and low affinity) on Jurkat and NALM 6 cells and further support the notion that these cell lines express enkephalin binding sites belonging to the family of classical opiate/opioid receptors. Previously, Madden et al. (Madden et al., 1987) identified a single type naloxone binding site of intermediate affinity (Kd=56 nM) on isolated human peripheral blood T cells. It is possible that the difference between our findings and those of Madden (Madden et al., 1987) result from the fact that the previous studies measured the receptors on human peripheral blood T cells which are comprised of heterogeneous cell populations. The inventors have utilized homogeneous lymphoid populations in our studies and measured the sites expressed on cultured CD4+T and B cell leukemia lines. Additional studies are needed to identify relationship(s) existing between various kinds of lymphoid populations (eg. CD4+, CD8+, normal, transformed) and the opiate/opioid receptors expressed by these cells.

Figure 8A:
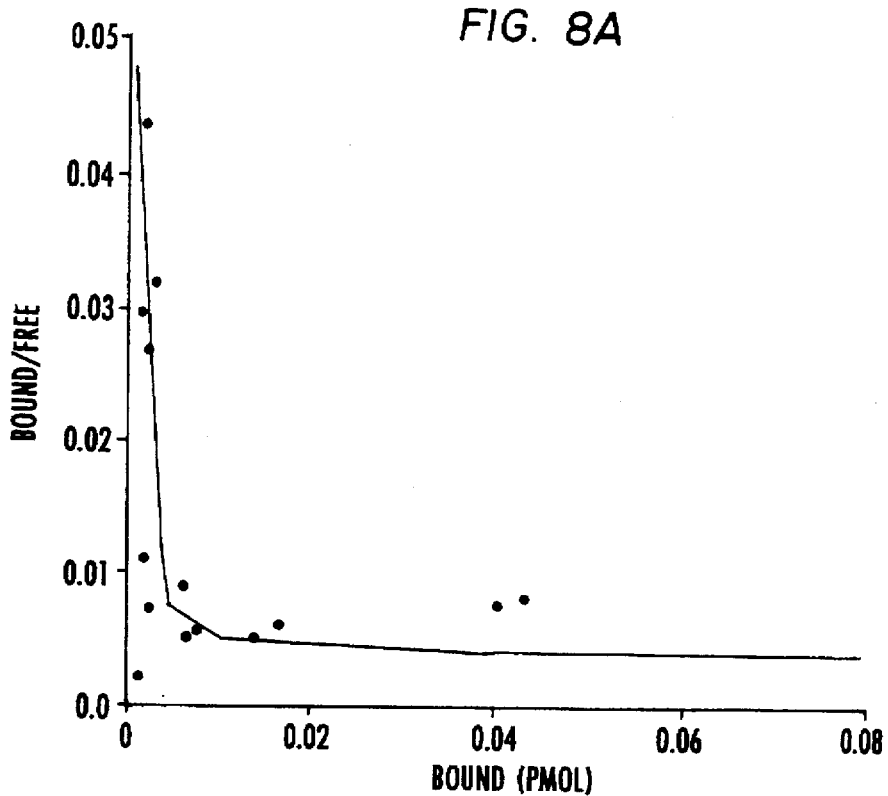
FIG. 8, Panels A and B. Methionine-enkephalin binds to two (high and low affinity) sites on leukemia cells. Data obtained from studies with the MET-ENK-FITC conjugate were replotted as ratio of bound to free MET-ENK-FITC (y-axis) vs bound concentration (x-axis) in Scatchard plots. The curves which were generated were nonlinear, asymptotically approaching a horizontal line (Panel A). In order to find the best fit and an appropriate receptor model the data were then subjected to analyses using a modified version of the Ligand Computer System. The curvilinear plots were resolved into two linear components and the analyses showed that the data best fit a two site model (Panel B). The data presented were obtained in 2 separate experiments with Jurkat cells.
Figure 8B:
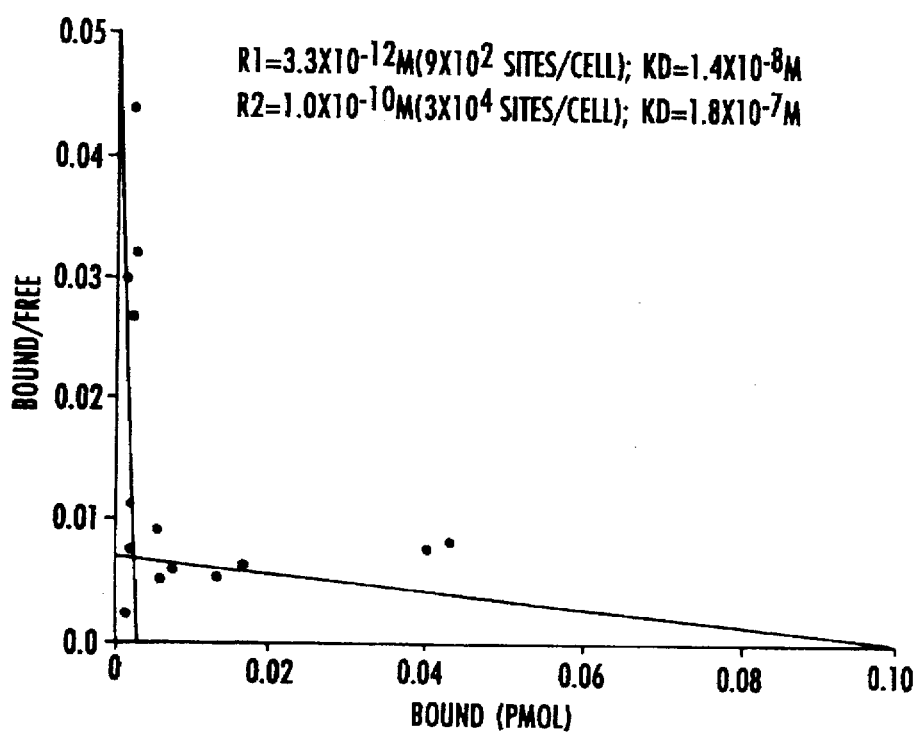
Figure 12A:
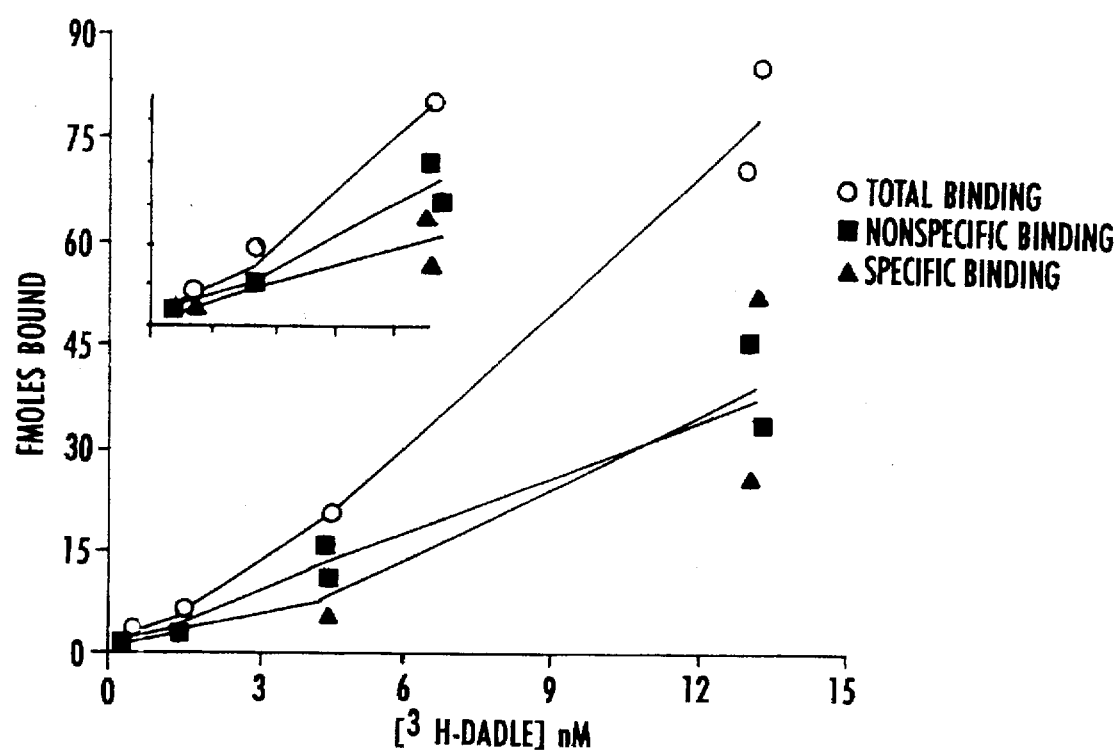
FIG. 12, Panel A with Inset, Panel B with Inset, Panel C with Inset, and Panel D with Inset. δ-opiate receptor agonists $^3$H-DADLE and $^3$H-DPDPE bind to Jurkat and NALM 6 cells. Data are plotted as the concentration of tritium-labeled δ-receptor agonist added to the cells (x-axis) vs the amount of label bound to the cells (y-axis). The total binding represents that measured for cells incubated with the labeled compound, alone. Nonspecific binding was determined for replicate samples which were incubated with the labeled compound and 50 µM unlabeled naloxone. Specific binding was measured as the difference between the total and nonspecific values. Each data point represents the mean for triplicate samples. Panel A, Jurkat cells labeled with $^3$H-DADLE. Incubations were for 4.5 h at 20° C. Panel B, Jurkat cells labeled with $^3$H-DPDPE for 4.5 h at 20° C. The data of Panels A and B represent duplicate assays run on 2 different days. Panel C, Jurkat cells labeled with $^3$H-DPDPE for 18 h at 4° C. Panel D, NALM 6 cells labeled with $^3$H-DPDPE for 4.5 h at 20° C. Insets depict the binding measured for $^3$H-DADLE or $^3$H-DPDPE within the lower dose-range (i.e., 0.3 to 1.8 or 4.4 nM). The incubations were carried out in $Ca^{2+}$, $Mg^{2+}$ deficient HBSS in 96-well polypropylene microtiter plates. Each assay well contained $5 \times 10^6$ Jurkat or NALM 6 cells. Following incubation, the cells were transferred to Whatman GF/C glass fiber filters and washed with three 3-ml portions of ice cold HBSS. Cell associated radioactivity was measured using liquid scintillation counting.
Figure 12C:
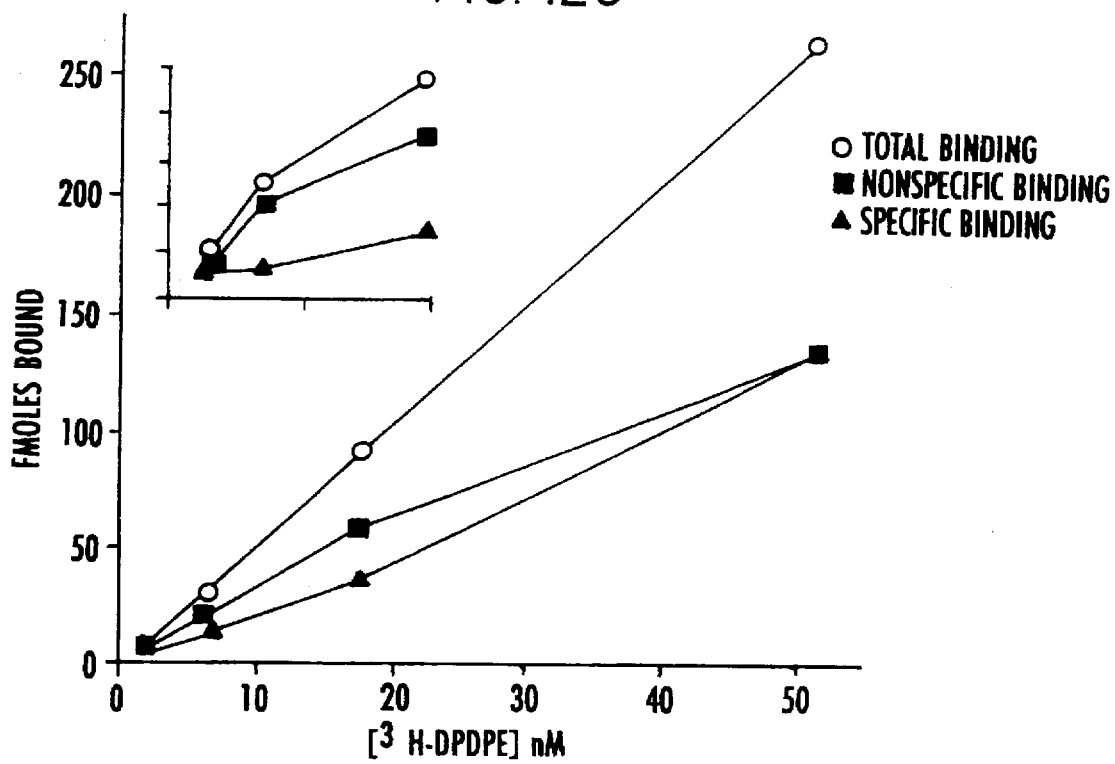
Figure 13A:
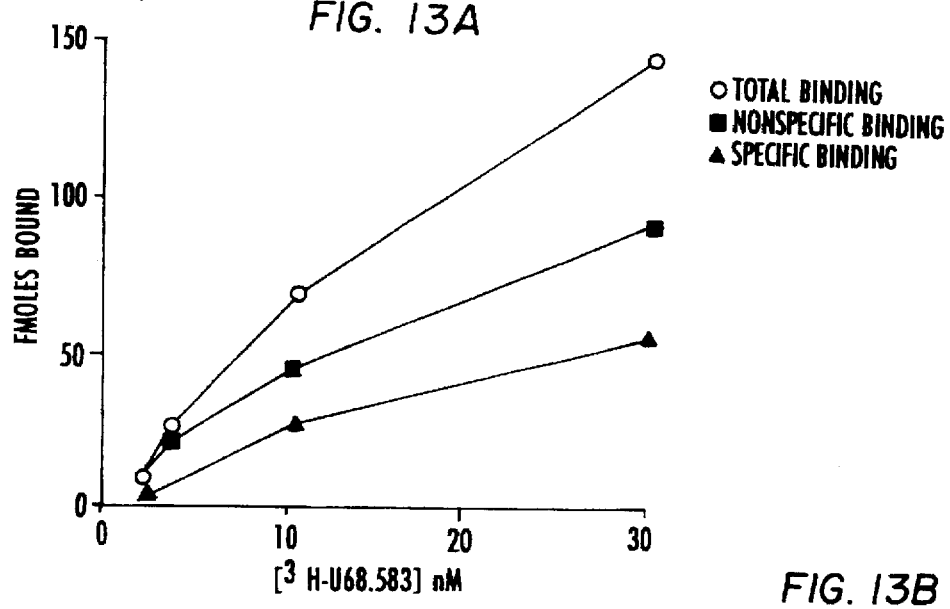
FIG. 13, Panels A-C. The κ-opiate receptor agonist $^3$H-U69,593 binds to Jurkat and NALM 6 cells. Data are plotted as the concentration of $^3$H-U69,593 (x-axis) added to the cells vs the amount of $^3$H-U69,593 bound to the cells (y-axis). The total binding represents that measured for cells incubated with $^3$H-U69,593, alone. Nonspecific binding was determined for replicate samples which were incubated with $^3$H-U69,593 and either 50 µM unlabeled naloxone or U69,593. Specific binding was measured as the difference between the total and nonspecific values. Each data point represents the mean for triplicate samples. Panel A, Jurkat cells labeled with $^3$H-U69,593, nonspecific binding measured with unlabeled naloxone. Panel B, Jurkat cells labeled with $^3$H-U69,593; nonspecific binding measured with unlabeled U69,593. Panel C, NALM 6 cells labeled with $^3$H-U69,593; nonspecific binding measured with unlabeled naloxone. The incubations were carried out in $Ca^{2+}$, Mg2+ deficient HBSS in 96-well polypropylene microtiter plates as described for FIG. 12.
Figure 13B:
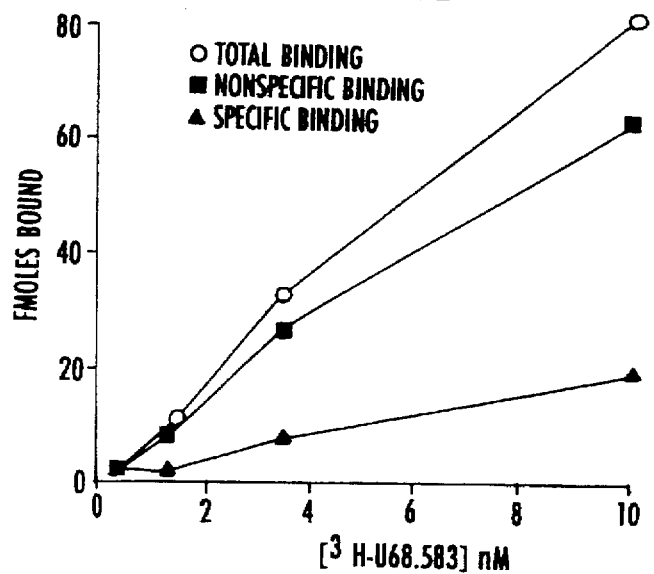
Figure 13C:
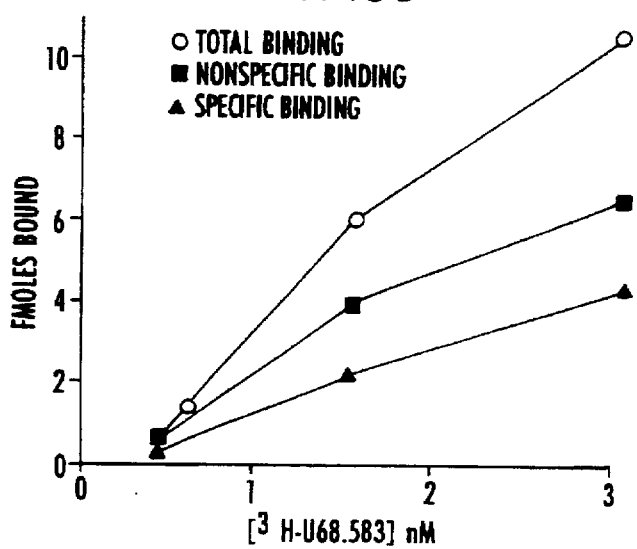

As probes for identifying the type and subtype of enkephalin binding sites expressed on the Jurkat and NALM 6 cells the inventors elected to utilize labeled opiate receptor agonists with selectivity for δ or κ type receptors. The inventors (Heagy et al., 1990; Heagy et al., 1992) have previously shown lymphocytes to have functional opioid receptors of δ and κ types. For these studies the inventors employed two δ-selective agents, the peptide agonist $^3$H-DADLE (Du Pont NEN Research Products, Boston, Mass.) and the highly δ-selective ligand $^3$H-DPDPE (Du Pont NEN Research Products, Boston, Mass.) which preferentially labels receptors of the $δ_{-1}$ subtype. $^3$H-U69,593 (Du Pont NEN Research Products, Boston, Mass.) which selectively labels classical opiate receptors of the κ-1 subtype was employed for identifying the κ-type sites on the leukemia cells. Specific binding (determined as the difference between total and nonspecific binding) was demonstrated for δ ($^3$H-DADLE, $^3$H-DPDPE) and κ ($^3$H-U69,593) selective ligands at concentrations ≤0.3 to 0.6 nM (FIG. 12 and FIG. 13). When applied to NALM 6 cells $^3$H-DPDPE or U69,593 was at concentrations s 5 nM, the specific binding constituted ~50–80% of the total (FIG. 7, Panel D; FIG. 8, Panel C). Specific binding measured for the Jurkat cells was ~50–60% at doses of 50 nM $^3$H-DPDPE or $^3$H-U69,593 and at doses of 14 nM $^3$H-DADLE (FIG. 12 and FIG. 13). The fact that a portion of the binding of these highly selective opiate receptor agonists was reversed by naloxone (FIG. 12 and FIG. 13) provides further evidence for the existence of classical type opiate receptors on the leukemia lines. The inventors' findings show that NALM 6 and Jurkat leukemia cell lines bind $^3$H-DPDPE (ligand for the $δ_{-1}$ subtype) and $^3$H-U69,593 (an agonist with selectivity for $κ_{-1}$ receptor subtype) suggest that these cells express opiate binding sites of the $δ_{-1}$ and $δ_1$ subtypes.

Figure 14A:
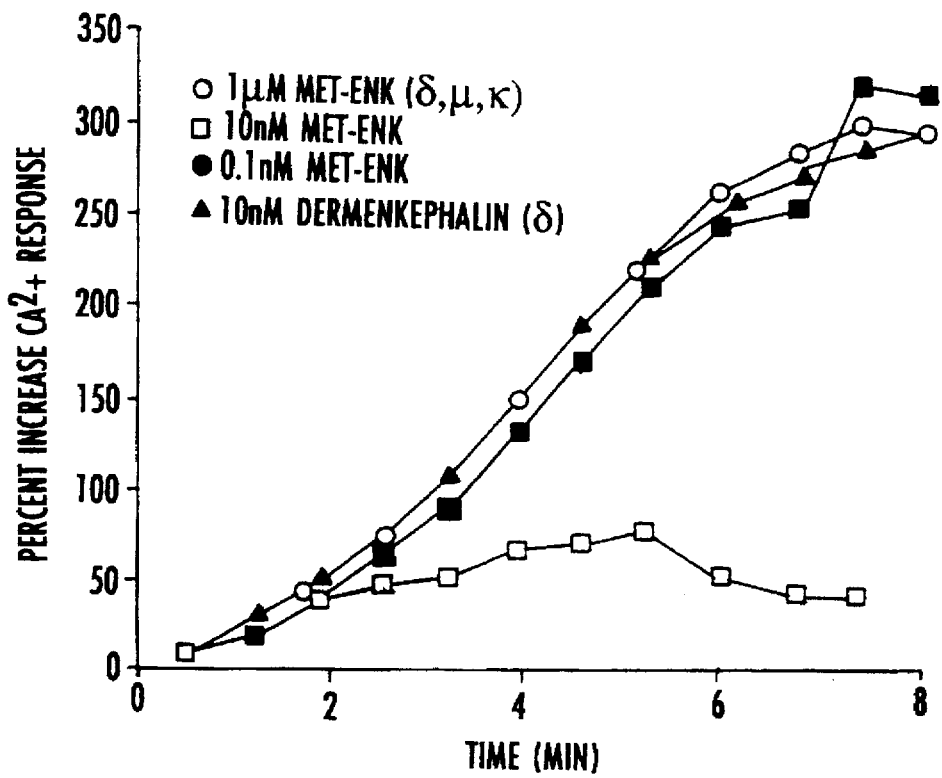
FIG. 14, Panel A and B. Methionine enkephalin and opiate receptor agonists selective for δ type receptors stimulate transmembrane signaling in Jurkat cells. Cells were labeled with Indo-1, washed twice in serum-free medium and held at 4° C. until analyzed. Indo-1 fluorescence was measured using flow cytometry as previously described (Heagy et al., 1992; Ledbetter et al., 1987; Chang et al., 1989; Rabinovitch et al., 1986). The fluorescence for nonstimulated cells (measured in medium, alone) was arbitrarily set at 1.0. Data are presented as per cent increase in the response [(r-baseline) x 100%]. Baseline [$Ca^{2+}$]i value measured for Jurkat cells (n=4) was 80±40 nM. Baseline Panel A, Jurkat cell response to MET-ENK (0.1 nM, 10 nM and 1 μM) and to the d- selective agonist Dermenkephalin (10 nM). Panel B, Jurkat cell response to the d- selective agonist (D-Pen $^{2,5}$, p Cl-Phe$^4$)-ENK (0.1 nM. 10 nM. 1 μM).
Figure 14B:
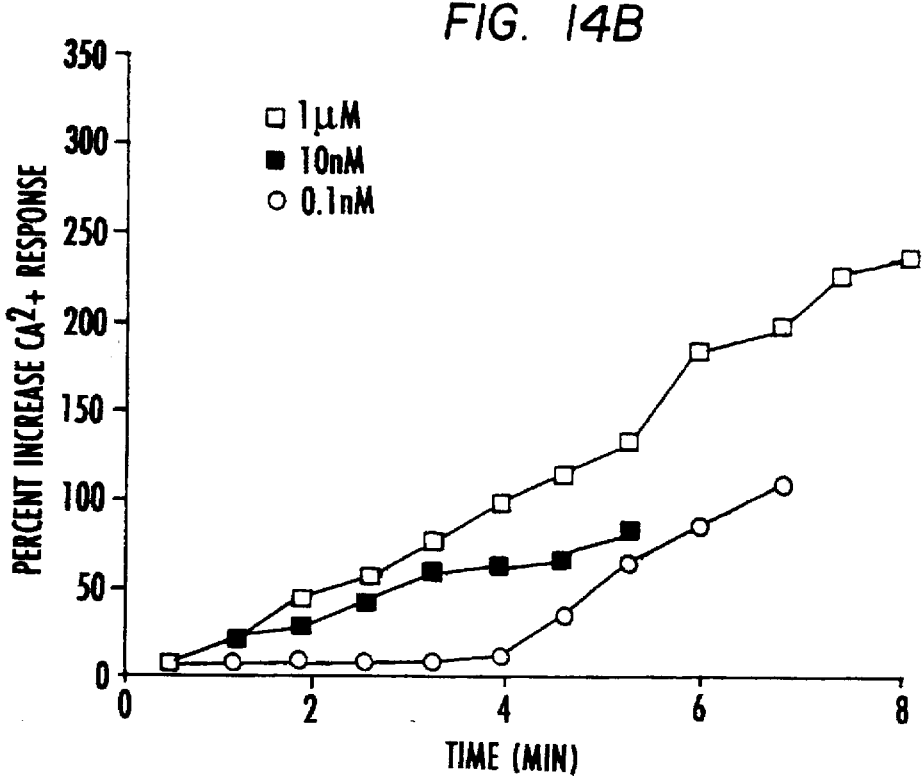

The inventors (Heagy et al., 1992) have previously shown that when applied to NALM 6 cells the $κ_{-1}$ agonist U69,953 stimulates a rapid increase in [Ca$^{2+}$]i. Taken together these findings suggest that the binding sites the inventors have identified using $^3$H-U69,593 are functional receptors which stimulate transmembrane signaling via rapid increases in [Ca$^{2+}$]i. In order to determine whether the sites the inventors have identified using the δ-selective agonists also elicit Ca$^{2+}$ responses the inventors measured the effects of opioid peptides and δ-selective agonists on the calcium response. For these studies Jurkat cells were loaded with the Ca$^{2+}$ sensitive dye indo-1 and the effects of MET-ENK and highly selective δ-opiate receptor agonists on [Ca$^{2+}$]i were measured by flow cytometry using previously described techniques (Heagy et al., 1992). When applied to Jurkat cells physiological concentrations (≦10$^{31\ 10}$M) of the endogenous opioid peptide MET-ENK elicited a rapid rise in [Ca$^{2+}$]i (FIG. 14). At slightly higher concentrations, and well within the pharmacological range (10$^{-8}$ to 10$^{-6}$M) highly selective δ-selective peptides including dermenkephalin and (D-Pen$^{2,5}$p-Cl-Phe$^4$)-ENK stimulated the Ca$^{2+}$ response (FIG. 14). These studies provide evidence that Jurkat cells have functional δ opiate receptor sites which stimulate transmembrane signaling via rapid increases in [Ca$^{2+}$]i.

In conclusion, the inventors have demonstrated that NALM 6 and Jurkat cells express specific, high affinity binding sites for the endogenous opioid pentapeptide MET-ENK. The inventors' studies suggest that these leukemic cell lines possess both high and low affinity MET-ENK binding sites. Such lymphoid receptors have not been described previously. The inventors have utilized homogeneous populations of T and B cell leukemia lines for our studies. Whether the receptors the inventors have identified are also expressed on normal human lymphoid cells or limited to leukemia and other abnormal populations remains to be determined. It is significant, however, that Taub et al (Taub et al., 1991) have shown that the addition of U69,593 and other k-selective opiate agonists to murine splenocyte cultures results in the inhibition of antibody responses. It is likely, therefore, that κ receptors are expressed on normal, murine spleen cells. In as much as different kinds of lymphocytes (eg. CD4+ vs CD8+ T cells) may express distinct forms of opiate/opioid receptors it will be necessary to use other homogeneous cell populations to address this question. Ultimately, isolation, purification and characterization at the molecular and genetic levels will be necessary for characterizing these sites.

Using opiate receptor selective ligands the inventors have identified naloxone-sensitive functional opiate receptors of the d and k types on Jurkat and NALM 6 cells (see FIG. 14). The fact that opiate receptor agonists selective for $δ_{-1}$ (DPDPE) and $κ_1$ (U69,953) subtypes bind to these cells (FIG. 12 and FIG. 13) and stimulate transmembrane Ca$^{2+}$ signaling (see FIG. 14) provides evidence to suggest that leukemia cells express functional receptors of the $δ_{-1}$ and $κ_1$ subtypes. The inventors' studies underscore the possibility that endogenous opioid peptides, via direct interaction with leukemia cells, have relevancy for leukeogenic processes and clinical course of disease.

EXAMPLE 5

Identification of a Lymphocyte Opioid receptor

A. BACKGROUND

The inventors have now identified a novel lymphocyte receptor that is expressed on activated human peripheral blood B cells, some cultured B cell lines, and to a lesser extent on human T cells, nonactivated B cells and some cultured, human T cell leukemias (e.g., Jurkat cells). Analyses of a cDNA encoding this receptor, termed EBI1, (isolated using subtractive hybridization methods) shows that it is a novel member of the R7G superfamily of transmembrane proteins having sequences homologous to those of known opiate receptors (e.g., Mor-1). Alignment of the deduced amino acid sequences of this lymphocyte R7G receptor with those reported for classical opiate receptors reveals 23–28% amino acid identity. Within the transmembrane (TM) regions there is 60–80% homology between the lymphocyte receptor and classical opioid receptors. The sequences determined for the novel lymphocyte R7G, like those for classical opioid receptors show ~30–40% homology to chemotactic receptors for fMET-LEU-PHE and IL-8. Comparison of the sequences for the lymphocyte R7G receptor and those for members of the classical opioid receptors family, show that both have Cys residues in the first and second extracellular loops that may form disulfide bridges; sites for N-linked glycosylation in the putative $NH_2$-terminal; the sequence motif S-(I/V)-D-R-(Y/F)-X-X-X-X-X (X represents consecutive hydrophobic residues) within the TM 2 domain (see Birkenbach et al., 1992, FIG. 1 text) that is thought to be essential in agonist binding; and several likely sites for phosphorylation by cAMP-dependent protein kinase and protein kinase C. Inspection of the amino acid sequence deduced for the novel lymphocyte R7G shows that there is an Asp at position 95; this feature has been demonstrated to be essential for the binding of δ-selective agents to the cloned murine δ receptor. Although the novel lymphocyte R7G shares many common properties with members of the classical opioid receptors family, it is distinct since its sequence is notably different in the regions comprising the putative amino terminus, TM 4 and 6 domains and the carboxyl terminus.

Northern analysis of human tissues has shown that this novel receptor is expressed predominantly in lymphoid cells (See Birkenbach, et al., 1992, FIG. 4). This R7G shows a different pattern of distribution (tissue specificity) than most opiate binding proteins. Classical opioid receptors are expressed predominantly in the CNS and other neuronal tissues, however recent studies have confirmed their presence in human peripheral blood and murine spleen cells. Gaveriaux-Ruff et al. (1994) using reverse transcriptase- (RT) and polymerase chain reactions (PCR) identified mRNA for the μ-type receptor in human peripheral blood cells and μ and δ type mRNA's in murine splenocytes.

The inventors have measured the effects of MET-ENK on COS cells transfected with the lymphocyte receptor cDNA. When the novel lymphocyte R7G was expressed in COS cells MET-ENK increased the level of intracellular cAMP, Table 6. As expected, the enkephalin had no effect on the cAMP produced in mock transfected controls (i.e., COS cells transfected with the vector, alone). Consistent with the specificity expected for a classical OR, the enkephalin effect on cAMP in transfectants expressing the novel lymphocyte R7G was inhibited by the opiate antagonist naloxone. Using $^3$H-DPDPE the inventors have demonstrated high affinity ($K_d$=0.2 nM), specific binding to membranes prepared from COS cells transfected with cDNA encoding the novel lymphocyte R7G (FIG. 19). These findings identify a novel lymphocyte opioid binding protein that plays a role in immunoregulation as well as other vital functions.

B. DISCUSSION

1. Opioid peptides are potent stimulants for the migration of human lymphocytes. Previously, the inventors have demonstrated that MET-ENK, β-endorphin and the synthetic opioid agonists DADLE and DAMGO are potent stimulants for the migration of isolated human T cells (Heagy et al., 1990. In recent studies the inventors have shown that physiological concentrations of MET-ENK cause the in vitro migration of pre-B acute lymphoblastoid leukemia cells (FIG. 1 and FIG. 5). Activation of the pre-B ALL cells with MET-ENK results in an increase in their migration and an augmentation in their surface expression of CD9 (FIG. 1 and FIG. 3). Other investigators have suggested that CD9 is (a) an adhesion molecule that triggers leukemia cell aggregations and (b) a tumor cell marker that regulates the spontaneous motility of certain kinds of tumor cells (Ikeyama et al., 1993). The inventors, findings suggest that opioids, possibly via their effects on CD9, may be important factors in the regulation of leukemia cell motility (See FIG. 1 and Table 1).

2. Opiates/opioids bind to specific, saturable binding sites expressed on leukemia cells. For the purpose of identifying and characterizing the opioid receptors expressed on lymphoid cells the inventors have prepared and utilized a fluorescein derivative of the physiological opioid pentapeptide MET-ENK. The inventors measured the binding of this fluorescein-tagged opioid to cultured leukemia cells using flow cytometry (FIG. 6, FIG. 7 and FIG. 8). Two enkephalin binding sites (high and low affinity) with Kd of 1.01 and 318 nM, corresponding to $7.77 \times 10^3$ and $4.48 \times 10^4$ sites, respectively, were measured for NALM 6 cells (B cell leukemia) and $9.0 \times 10^2$ high affinity (Kd, 1.36 nM) and $3.0 \times 10^4$ low affinity (Kd, 180 nM) sites/cell were identified for Jurkat cells (T cell leukemia) (See FIG. 8 and Table 5).

Similar findings were obtained when $^3$H-naloxone and conventional radioligand-receptor filtration assays were employed to measure the sites expressed on these cells. Nonlinear regression analyses of the data obtained with $^3$H-naloxone was best fit by the two-site model. Kd of 4.7 nM and 230 nM, ($3.3 \times 10^4$ and $1.75 \times 10^5$ sites, respectively) were measured for NALM 6 cells and $8.67 \times 10^2$ high affinity (Kd, 2.99 nM) and $1.82 \times 10^4$ low affinity (Kd, 125 nM) naloxone binding sites/cell were identified for Jurkat cells (See FIG. 9, FIG. 10 and FIG. 11 and Table 5).

TABLE 5

MET-ENK and naloxone bind to recognition sites on NALM 6 and Jurkat cells

| | $K_d$ (nM) | $B_{max}$ | (sites/cell) | |
|---|---|---|---|---|
| NALM 6 | | | | |
| MET-ENK | 1.01 | 318 | $7.77 \times 10^3$ | $4.48 \times 10^4$ |
| Naloxone | 4.7 | 230 | $3.3 \times 10^4$ | $1.75 \times 10^5$ |
| Jurkatk | | | | |
| MET-ENK | 1.36 | 318 | $9.0 \times 10^2$ | $3.0 \times 10^4$ |
| Naloxone | 4.7 | 230 | $3.3 \times 10^4$ | $1.75 \times 10^5$ |

Binding studies were carried out as previously described. Data presented were obtained in two separate experiments. When the data with $^3$H-Naloxone were replotted in Scatchard plots (bound label on the x axis vs the ratio of bound to free naloxone on the y axis) the resultant curves were nonlinear, asymptotically approaching a horizontal line. Nonlinear regression analysis performed with the aid of the Ligand Computer System revealed two linear components and showed that the data best fit a two site model. Panel B, Scatchard analysis of $^3$H-Naloxone binding to Jurkat cell membranes. Data presented were obtained in two experiments.

Figure 15B:
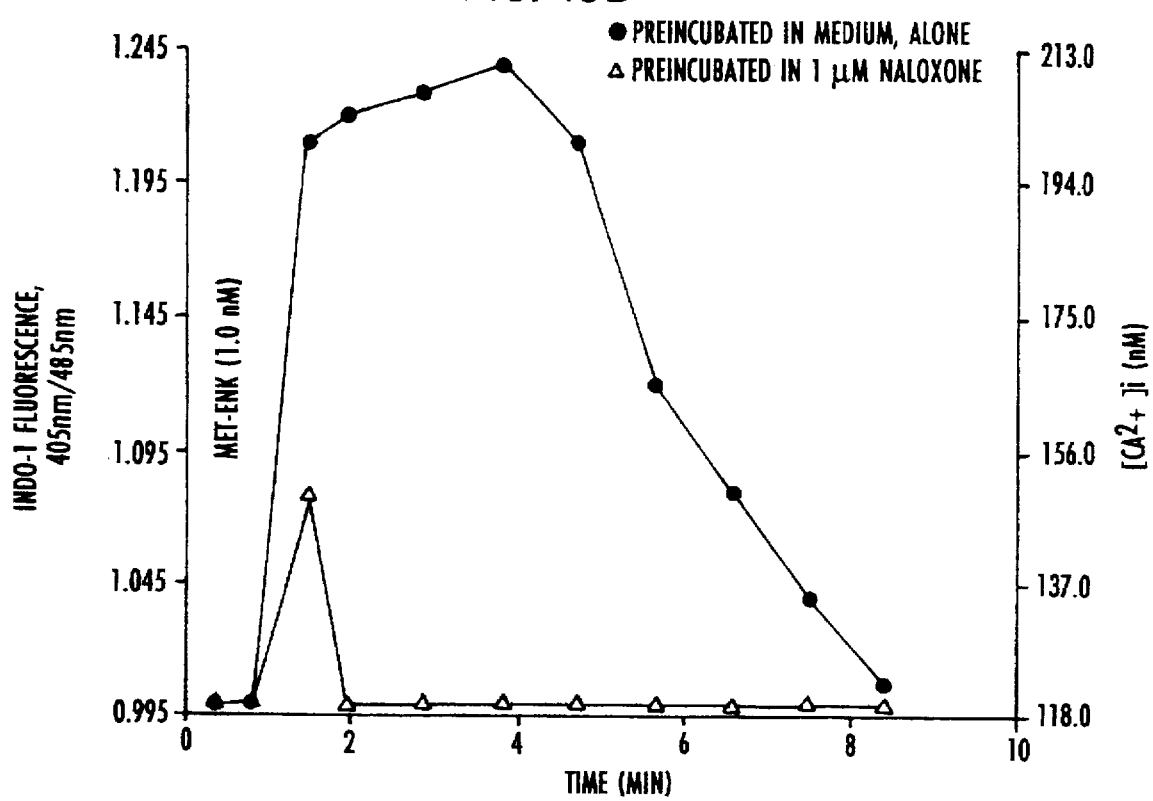
FIG. 15, Panels A-C. Binding of methionine-enkephalin to its receptors on leukemia cells results in a concentration dependent rise in [$Ca^{2+}$]i which is inhibited by naloxone. Cells were labeled with Indo-1 as previously described (Rabinovitch et al., 1986), washed twice in serum-free medium and held at 4° C. until flow cytometric analysis. The violet/blue fluorescence ratio was measured using previously described methods (Rabinovitch et al., 1986). Non-stimulated cells (measured in medium, alone) were used to establish a relative violet/blue ratio arbitrarily set at 1.0 as previously described (Rabinovitch). Calibration of [$Ca^{2+}$]$_i$ was carried out as previously described by Rabinovitch et al (1986) using the formula.
Figure 15C:
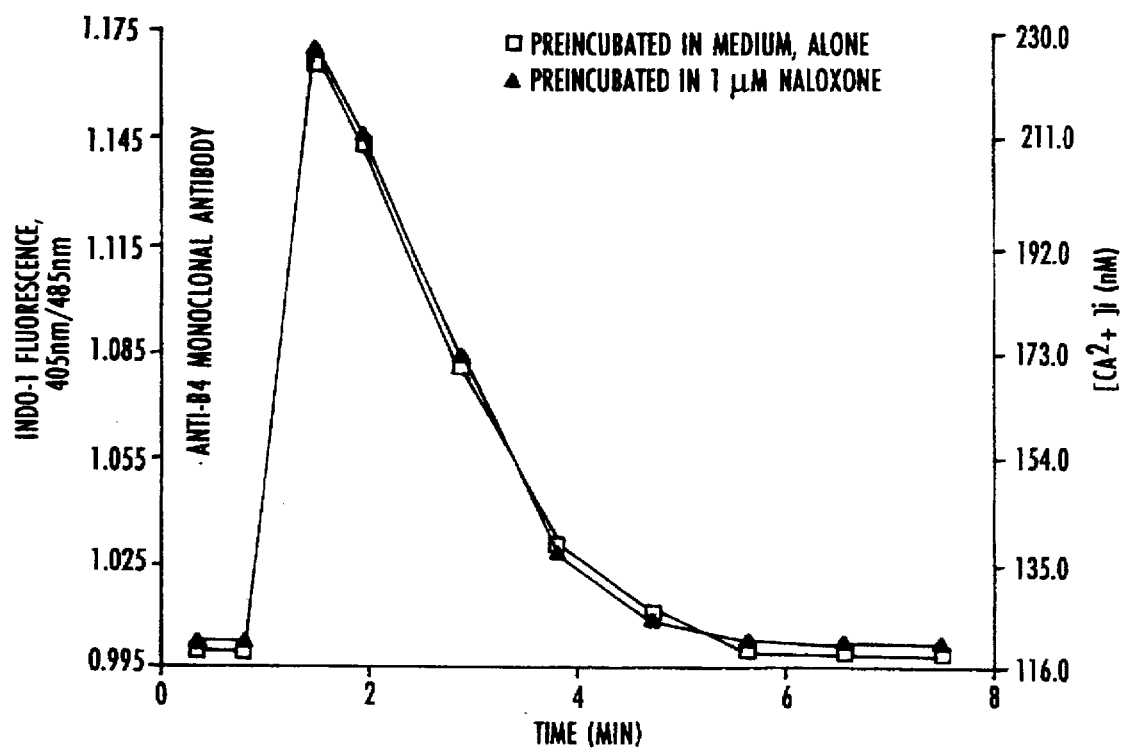

3. Opiates/Opioids activate two lymphocyte transmembrane signaling pathways. When applied to lymphocytes opiates/opioids elicit a rapid rise in $[Ca^{2+}]_i$. The application of MET-ENK or other synthetic opiates/opioids to NALM 6 cells results in a rapid rise in $[Ca^{2+}]_i$ (FIG. 14 and FIG. 15). The addition of MET-ENK to forskolin-activated NALM 6 cells results in an enhancement in the production of cAMP (FIG. 16). Receptor mediated signaling via $[Ca^{2+}]_i$ and cAMP is modulated by G proteins; therefore, these findings suggest that the opiate/opioid effects on NALM 6 cells are mediated via such regulatory G proteins.

4. Identification of a novel human lymphocyte cDNA clone that encodes an opioid binding protein. Upon inspection, this clone was found to code for a G-linked receptor having seven transmembrane domains and homology to previously identified opiate receptors. Alignment of the sequences of with those of known opioid receptors (e.g., Mor-1) showed 23–28% amino acid identity. The transmembrane regions are more highly conserved with 60–80% homology to the previously described opioid receptors.

TABLE 6

MET-ENK stimulated cAMP accumulation in COS cells transfected with EBI 1 is inhibited by naloxone.

| Treatments | COS (Vector Control) | COS (EB I 1) cAMP (fmoles/cell × $10^3$)$^a$ |
|---|---|---|
| Control-1$^b$ | 40.2 | 61.2 |
| Control-2 | 38.8 | 63.5 |
| MET-ENK$^c$ | 31.6 | 109.6 |
| Naloxone$^d$ | 31.4 | 76.4 |
| MET-ENK & Naloxone | 29.6 | 58.4 |
| Forskolin$^e$ | 130.5 | 234.8 |

$^a$Cells were preincubated for 5 minutes at 37° C. in the presence of 1 mM 3-isobutyl-1-methylxanthine. MET-ENK and naloxone were prepared as stock solutions, diluted in DME medium directly prior to assays and added to the cell samples in 10 µl volumes. Forskolin was dissolved in DMSO and added in a 10 µl volume of this solvent. Cells were then incubated for an additional 20 minutes at 37° C., the reactions stopped by addition of ice cold TCA and the TCA soluble supnatants extracted with hydrated ether. A commercial RIA kit was used for measureing the cAMP content of the samples.
$^b$Control-1 received 10 µl of DME medium, alone. Control-2 received 10 µl of the DMSO solvent.
$^c$The concentration of MET-ENK (final) was 0.01 nM.
$^d$The concentration of naloxone (final) was 10 µM.
$^e$The concentration of forskolin (final) was 0.1 µM. It should be noted that forskolin stimulation is thought to bypass the usual receptor-G protein activation process and occur via direct interaction with adenylate cyclase. In this set of studies forskolin was used as a positive control.

EXAMPLE 6

Definition of the pharmacological profile and ligand binding features of EBI1.

A. Elucidation of the pharmacological specificity of EBI1.

Ligand-receptor binding will be measured for a panel of opiate agonists, antagonists and related peptides. After transfection, COS cell membranes will be prepared and ligand binding measured using labeled opioid agonists and antagonists. Specific binding will be determined as the difference between total and non-specific (measured in the presence of excess unlabeled agonist or antagonist) binding. Kd's will be measured by nonlinear regression and Scatchard analysis. Competition assays will be carried out using high affinity labeled ligands and a panel of opiate agonists and antagonists. The pharmacological type and subtype of the lymphocyte receptor will be defined from the analyses of the relative affinities (Ki's) measured for these agents. From these studies the inventors expect to elucidate the pharmacological specificity of a EBI1.

1. Rationale

The inventors' preliminary studies show that δ-type opiate receptor ligands bind to and activate EBI1. Using the opiate receptor selective agents $^3$H-DPDPE and $^3$H-DADLE the inventors have identified specific naloxone-sensitive recognition sites on cultured lymphoid cell lines (FIG. 12). The inventors' preliminary studies demonstrate specific $^3$H-DPDPE binding (measured in the presence of excess unlabeled naloxone) to membranes prepared from COS cells transfected with cDNA encoding the lymphocyte receptor (FIG. 18). Further, in functional assays carried out with COS cell transfectants expressing the lymphocyte receptor both MET-ENK and DPDPE (δ-selective agonist) but not DAMGO (µ-agonist) or U50,488 (κ-agonist) elicited an elevation in intracellular cAMP content (data not shown). To confirm that the isolated lymphocyte cDNA clone encodes an opiate receptor and to fully define the pharmacological specificity of the protein in terms of receptor type and subtype the inventors will measure the binding of additional opiate receptor ligands to this receptor.

2. Methods

The inventors will measure and then compare the specific binding of δ-selective peptide agonists (e.g., $^3$H-DPDPE, DADLE, Deltorphin), δ-selective antagonists ($^3$H-naltrindole) and high affinity but non-selective alkaloids ($^3$H-diprenorphine) to COS cell membranes prepared from transfected COS cells. After transfection the inventors will prepare membranes from the cells, incubate the membranes with labeled opiate receptor ligands, and then measure the amount of membrane bound label. Membranes will be prepared as described (FIG. 10, Prelim. Data) from cells transfected with cDNA encoding the lymphocyte receptor and from mock transfected controls. Ligand binding to the membranes will be measured using conventional filtration assays; specific binding will be measured as previously (see FIG. 10 AND FIG. 19, Prelim. results). Binding will be quantitated over the full range of doses (e.g., 0.1 to 100 nM) and saturation isotherms evaluated. From these studies the inventors will select the appropriate ligand(s) (i.e., those yielding low Kd's and high levels of specific but low non-specific binding) to carry out competitive studies to measure Ki values for a large panel of opioid receptors and other related (e.g., somatostatin) ligands. With these competition studies the inventors will then define the specificity (pharmacological type and subtype) of the lymphocyte receptor; a large panel of agents including the endogenous opioid peptides, pharmacologically important opiates and ones known to selectively bind to distinct opiate receptor subtypes will be employed. Stereospecificity will be determined by measuring the displacement of membrane bound label in the presence of (+) and (−) naloxone. In competition studies the labeled ligand will be added at concentrations s less than the Kd (determined from saturation binding curves); unlabeled agents will be titered over a 0.6 log dose range (e.g., 001 to 1000 inM). Relative affinities (Ki's) will be measured by the Chang-Prusoff method. The data obtained in these binding assays will be used to evaluate the effects that mutations in the receptor have on ligand binding.

3. Expected results and future studies

The inventors' data may show that the rank order of affinities (Kd values) measured for the ligand- lymphocyte association are $^3$H-diprenorphine<naltrindole<Deltorphin<DADLE<DPDPE. These studies would be consistent with the pharmacological profile of a classical δ-2 type opiate receptor (Yasuda et al., 1993). A second possible outcome from these studies is that the inventors may find that the data point to a classical receptor of the δ-1 type; this will be the case if the rank order of affinities (Kd values) measured for the ligand- lymphocyte association are ³H-diprenorphine<DADLE<DPDPE<naltrindole<Deltorphin. If the inventors find that ³H-diprenorphine binding results in high levels of specific (i.e, Ka≦0.5 nM) but low non-specific binding the inventors will then use this agent for our competition studies and measure the displacement of ³H-diprenorphine by other opiate agonists, antagonists and related agents. If the lymphocyte receptor exhibits the same requirements for stereoselectivity as classical opioid receptors the inventors expect the ki value for (+) naloxone to be ≧100 times that measured for (−) naloxone. If this receptor has the binding characteristics of a δ-2 subtype the inventors expect the Ki value measured for the δ-2 selective antagonist NTB to be >than that measured for the δ-1 selective antagonist BNTX. If these are the findings the inventors will conclude that the novel lymphocyte receptor has the pharmacological profile of a classical opioid receptor of the δ-2 subtype. On the other hand if this receptor the characteristics of a classical δ-1 opioid receptor the inventors expect the $K_i$ value the δ-2 selective antagonist NTB to be > than that determined for the δ-1 antagonist BNTX. If these are the findings the inventors will conclude that the novel lymphocyte receptor has the pharmacological profile of a classical opioid receptor of the δ-1 subtype.

A third possible outcome from these studies is that the inventors find that this lymphocyte receptor is unique and exhibits a distinctive pharmacological profile. If the studies show that the rank order of affinities (Kd) are DADLE<DPDPE <Deltorphin <³H-diprenorphine <naltrindole the inventors will conclude that this receptor may be distinct from previously described opioid binding proteins. If these are the findings and ³H-DADLE is a suitable ligand for competition studies (i.e., binds with high affinity specific and low nonspecific binding) the inventors will then use this agonist for competition assays and the relative affinities of a large panel of prospective ligands will be measured. If the inventors find (a) that the ki value for (+) naloxone is equivalent to that for (−) naloxone, indicating a lack of stereoselectivity or (b) that des-TYR MET or LEU-ENK yield Ki's equivalent to the full length enkephalins the inventors will conclude that the binding requirements for this lymphocyte receptor are different from those of all previously described members of the RG7 superfamily.

From these studies the inventors will elucidate the pharmacological specificity of EBI1.

B. Mapping binding site(s) for agonists and antagonists of EBI1.

For investigating mechanisms by which agonists and antagonists interact with EBI1 the inventors will identify the residues that direct ligand binding. Amino acid substitutions will be made in extracellular, transmembrane and intracellular domains. Mutant and wild-type cDNA's will be expressed in COS cells, membranes prepared and specific binding measured using radiolabeled ligands. Binding will be measured for selective and nonselective opiate agonists and antagonists. The effects of the amino acid replacements on ligand binding will be determined by comparisons between wild-type and mutant receptors. From these studies the inventors expect to identify key structural residues in the lymphocyte receptor that define the binding requirements for selective peptide and nonpeptide agonists, non-selective agonists, and both nonselective and selective antagonists.

1. Rationale

All muscarinic receptors contain a series of conserved Ser, Thr and Tyr residues, most of which do not occur in other G protein-coupled receptors. Using a series of single point mutations in rat M3 muscarinic receptors it was shown that two Thr residues (Thr231 and Thr234) as well as four Tyr residues (Tyr148, Tyr506, Tyr529 and Tyr533) are important for high affinity acetylcholine binding (rev in Wess, 1993). Mutations at these sites diminished agonist binding but little effect on antagonist binding, indicating that different receptor subsides are involved in the binding of muscarinic receptor agonists and antagonists. Kong et al., 1993 have shown that substitution of the Asp95 residue in the cloned mouse δ-opiate receptor with an Asn reduced the affinity for δ-selective peptide and non-peptide ligands but had little effect on non-selective opiate agonists. These findings suggest that selective and nonselective agonists bind to distinct receptor domains.

It is known that opiates/opioid modulate multiple immune as well as CNS activities. The presently available opiate agonists and antagonists interact with both lymphocytes and neurons. Therapeutics for the treatment of chronic pain and other conditions (i.e., graft rejection) are needed and the development of selective receptor ligands that regulate CNS (e.g., analgesia) or immune function (e.g., migration), but not both will facilitate this goal. The deduced amino acid sequence of the lymphocyte receptor the inventors have identified is distinct from that described for all the cloned classical μ, d, k opioid receptors and it is of interest to define the ligand binding regions of this novel protein. These studies may provide insights useful for the development of selective therapeutics that interact with lymphocytes or neurons but not both.

2. Methods

Figure 10A:
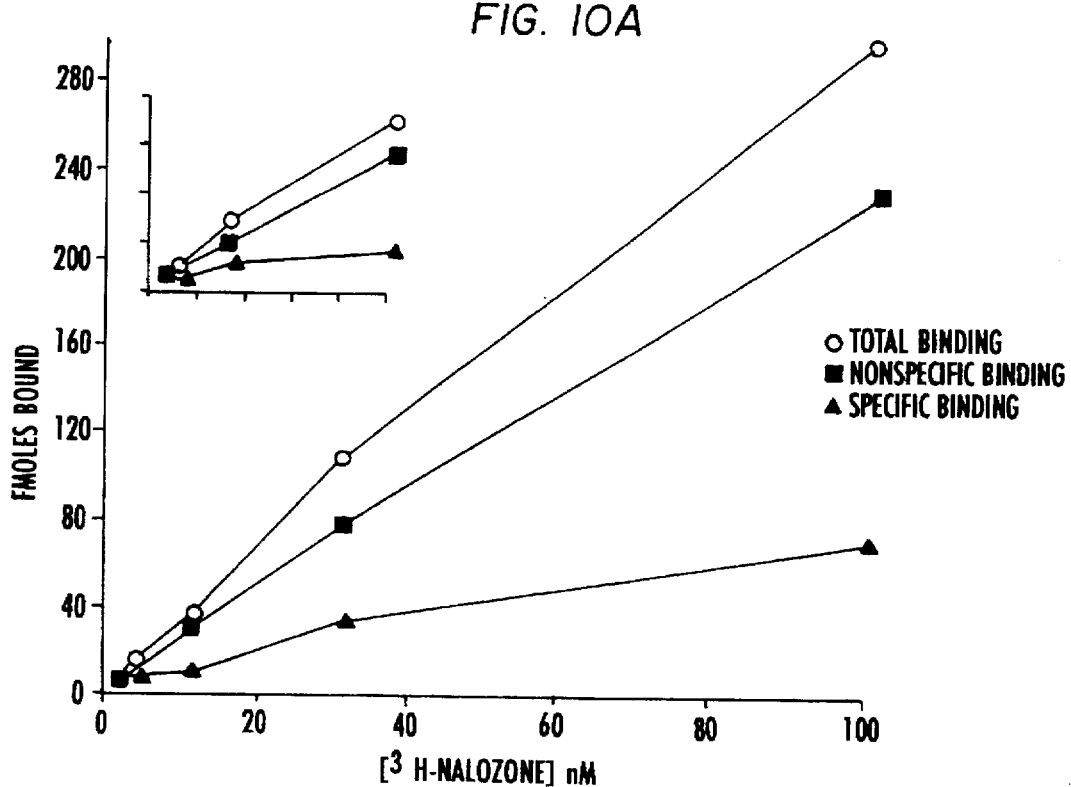
FIG. 10, Panel A with Inset and Panel B with Inset. $^3$H-Naloxone binds to Jurkat cell membranes. Data are plotted as the concentration of $^3$H-Naloxone added to the samples (x-axis) vs membrane bound $^3$H-Naloxone (y-axis). The total binding represents that measured for samples incubated with $^3$H-Naloxone, alone. Nonspecific binding was determined for a replicate set of samples which also contained 50 µM unlabeled naloxone. Specific binding was measured as the difference between the total and nonspecific binding components. Each data point represents the mean for triplicate samples. Assays were carried out in 96-well polypropylene microtiter plates (Costar Corporation; Cambridge, Mass.). Each assay well contained the membrane equivalent of $5 \times 10^6$ cells. Following incubation, the membranes were transferred to Whatman GF glass fiber filters, washed with three 3-ml portions of binding assay buffer, dried and then counted in a liquid scintillant. The membranes used in these studies were prepared from cultured Jurkat cells. Cells were harvested from culture in $Ca^{2+}$ and $Mg^{2+}$ deficient PBS, washed, resuspended in 50 mM Tris-HCl (pH 7.4), and frozen at –70° C. Frozen cell pellets (–70° C.) were thawed in 5 mM Tris-HCl (pH 7.4, 20° C.), containing 1 mM EGTA and then sonicated. The sonicate was centrifuged at 1,000 g for 10 minutes, the supernatant removed, and then centrifuged for an additional 20 minutes at 28,000 g. This pellet ($P_2$) was resuspended in 50 mM Tris-HCl containing 100 mM EGTA, 8% v/v glycerol, pH 7.4 and stored at –70° C. until used in the binding assays.
Figure 10B:
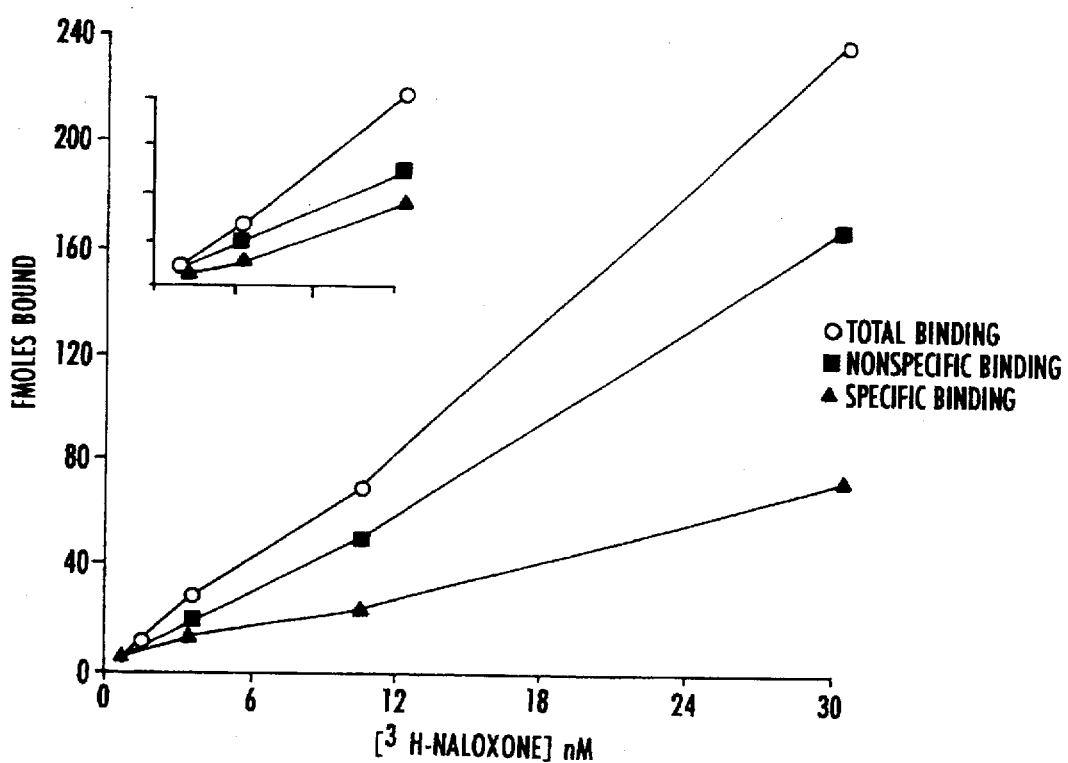

Using previously described methods (e.g., the Altered Sites in vitro mutagenesis system; Promega LKB Biotechnology Inc. (Kong et al., 1993); the inventors will induce point (single) mutations in the cloned lymphocyte receptor. Substitutions will be made in extracellular, transmembrane and intrasellar domains. These replacements will be confirmed by DNA sequencing. Mutated and wild-type cDNA will be transfected in COS cells and expression confirmed by RNA blot analysis. Membranes will be prepared as described (FIG. 10). The inventors will then (as described in IA, above) measure the specific binding of δ-selective peptide agonists (e.g., ³H-DPDPE, DADLE, Deltorphin), δ-selective antagonists (³H-naltrindole) and high affinity but non-selective alkaloids (³H-diprenorphine) to the cell membranes. The effect of amino acid replacements on ligand binding will be determined by comparisons between the Ka's measured for wild-type and mutant receptors. Subsequently, the inventors will select appropriate ligands (i.e., those which the inventors determine to show high affinity specific binding and low non-specific binding to the wild-type and/or mutant receptors) for competition studies. These initial studies are important because it is possible, at least in theory, that some of the mutants may show a shift in selectivity (e.g., shift from δ to μ or κ selectivity). If this is the case the inventors will then further evaluate the effects of the mutation using K (e.g., ³H-U50, 488) or m (³H-DAMGO) selective agents. Subsequently, competition assays will be employed for measuring and Ki's for mutant and wild-type receptors; a panel of potential receptor ligands will be studied (Table 3). By measuring and then comparing ligand binding the inventors will map the structural domains that direct selective and nonselective agonists and antagonists as well as peptide and alkaloid binding to protein.

3. Expected results and future studies

The inventors' results may or may not be similar to those of Kong et al. (1993) who found that a single substitution (Asp95) in the cloned mouse δ-receptor with an Asn reduced the affinity for δ-selective peptide and non-peptide agonists. If our studies show that the binding of selective but not nonselective agonists is diminished by a single substitution it is also likely that the inventors may identify site(s) that diminish nonselective but not selective agonist binding. Further, our studies with mutant receptors may, like previous studies with the muscarinic acetylcholine receptors identify sites that diminish agonist but not antagonist binding, indicating that different receptor subsides are involved in the binding of agonists and antagonists. Such findings will be important since they will provide key insights into the specificity of the lymphocyte receptors. Further, they will provide information that can be applied for the development of highly selective receptor antagonists and antisense probes for defining and characterizing the effects of opiates/opioids on immune function.

On the other hand our findings for the lymphocyte receptor may be unlike those of Kong et al. and the inventors may find that single substitutions have little effect on binding specificity. If this is the case the inventors will then analyze the effects of multiple replacements and thereby define the unique structural features of the lymphocyte receptor.

Once the inventors have defined the domains essential for ligand binding the inventors will then identify those which direct the second messenger systems activated via transmembrane signaling. From these studies the inventors expect to identify key structural residues in the lymphocyte receptor that define the binding requirements for selective peptide and nonpeptide agonists, non-selective agonists, and both nonselective and selective antagonists.

EXAMPLE 7

Identification of the transmembrane signaling mechanisms and activity requirements of EBI1

A. Definition of the transmembrane signaling mechanisms activated by EBI1.

In one set of studies transformed, stable CHO cell lines that express EBI1 will used for defining kinds of G-regulatory subunits that associate with this lymphocyte protein. Transformants will be stimulated with MET-ENK or other appropriate opiate agonists (i.e., those that have been shown to bind to this receptor; see Example 6, above). The effects of opiates/opioids on CHO transformants will be determined from comparisons between expressors and non-expressors of the lymphocyte R7G. In a second group of studies interactions with Gqα subunits will be defined using COS cells and co-transfection methods. In these studies COS cells will be co-transfected with cDNA encoding the lymphocyte R7G and cDNA's encoding Gqα subunits. In a third set of assays, antibodies against specific G protein subunits will be employed as probes for defining G protein-receptor coupling in lymphocytes. $^3$H-inositol labeling will be used for quantitating PI. [Ca$^{2+}$]i will be measured from Fura-2 fluorescence. cAMP will be assayed by RIA. In a fourth group of studies the inventors will solubilize the membrane receptors and then, using specific antisera directed against individual regulatory units, immunoprecipitate the receptor-G protein complexes. From these studies the inventors expect to identify (a) signaling pathways activated by the novel lymphocyte R7G and (b) G protein subunits that couple with this protein.

1. Rationale

Although many factors (e.g., cations, GTP) influence receptor-G protein interactions, the receptor sequence and specific G protein subunits expressed in different kinds of cells are critical determinants in these associations. In the studies described below the inventors will first identify G proteins which associate with the lymphocyte receptor and then define the receptor regions which are required for these associations (IIB, below).

The inventors' studies have shown that when applied to lymphocytes opiate/opioids stimulate rapid increases in [Ca$^{2+}$]$_i$ and modulate intracellular cAMP levels (see FIG. 14, FIG. 15 and FIG. 16). These findings show that the application of opiate/opioids to lymphocytes results in the activation of at least two signaling pathways. A number of other G-protein linked receptors including the thyrotrophin-releasing hormone (TRH), two subtypes of endothelin and three subtypes of tachykinin receptors been shown to stimulate the production of both cAMP and PI. The signaling pathways activated by receptors are defined by their interactions with G proteins. G proteins are usually divided into four families: G$_s$, G$_i$, G$_o$, and G$_q$ based on differences in their a subunits and in the functions they regulate. The Gs, Gi, Go type participate in the regulation of adenyl cyclase activity and those of the Gq class activate members of the β family of PLC isozymes to stimulate the release of inositols and diacylglycerol. Other investigators have found that COS 7 cells are deficient in the G protein a subunits (Gq family) necessary for lymphocyte signaling via inositol phosphates and [Ca$^{2+}$]$_i$. In our preliminary studies the inventors have shown that the addition of MET-ENK to COS cells transfected with the lymphocyte R7G cDNA increases cAMP production (Table 6). These findings are consistent with the activation of Gsα regulatory units. The inventors will now determine (a) whether the lymphocyte receptor associates with the Gq family of G proteins and (b) whether the receptor signals via PI and [Ca$^{2+}$]$_i$. The inventors have chosen to use CHO cells for these studies because they, unlike COS 7 cells, have G protein a subunits that initiate phosphoinositol hydrolysis (G$_q$) as well as those that regulate adenyl cyclase activity (G$_s$, G$_i$, G$_o$). The inventors will confirm our findings for the CHO cells in additional studies that identify the receptor-G protein associations that occur in T and B lymphocytes.

2. Methods

Transformed, stable CHO cell lines that express the novel lymphocyte R7G will be stimulated with MET-ENK and other appropriate opiate receptor agonists. The inventors will measure (a) the release of PI, (b) [Ca$^{2+}$]$_i$ and (c) the production of cAMP. PI and [Ca$^{2+}$]$_i$ will be quantitated as described previously (Aramori and Nakamishi, 1992; Nakajmi et al., 1992). For measuring phosphoinositol hydrolysis the inventors will label the cells with $^3$H-inositol; subsequently, the separation of $^3$H-inositol phosphates will be accomplished on Bio-Rad AG 1-x8 columns. [Ca$^{2+}$]$_i$ will be measured for cells grown on cover slips and loaded with the Ca$^{2+}$ sensitive dye Fura 2. Fura-2 fluorescence will be imaged using a microscope equipped with epifluorescence optics. The levels of cAMP produced in the cells will be measured by RIA as described for FIG. 16 and Table 6. The effects of opiate/opioid stimulation on these second messenger systems will be determined from comparisons between transformed cells that express the lymphocyte receptor and mock transformed controls.

3. Expected Results and Future Studies

If the studies show that MET-ENK stimulates the production of cAMP the inventors will conclude that the lymphocyte receptor probably associates with G proteins composed of α subunits of the $G_{\alpha_s}$ family. On the other hand, if the studies show that opioids diminish the level of cAMP produced in forskolin-activated cells the inventors will conclude that G proteins having α subunits of the $G_i$ type associate with this receptor. If the inventors find that following stimulation with MET-ENK the cells expressing the receptor exhibit (a) an increase in PI and (b) an elevation in $[Ca^{2+}]_i$ the inventors will conclude that activation of the lymphocyte receptor stimulates phosphoinositol hydrolysis and this response is probably regulated via G protein α subunits of the Gq class. If these are the findings the inventors will then determine whether the lymphocyte receptor transduces signals through any of the known Gq family members. The inventors will transfect COS cells with cDNA encoding the lymphocyte R7G alone or together with cDNAs encoding G proteins. Five cDNAs that encode α subunits of the Gq class have been characterized (Gαq, Gα11, Gα14, Gα15, and Gα16) and the inventors will use these for cotransfection. A similar approach was recently used to map the signaling paths activated by IL-8 receptors (Wu et al., 1993). COS cells expressing the lymphocyte R7G & one class of Gqα subunit will be stimulated with MET-ENK or other opiate/opioid. Coupling between the receptor and Gqα subunits will be identified by measuring the level of PI and $[Ca^{2+}]_i$. Controls for this set of studies will include mock transfections as well as cells transfected with cDNA encoding the lymphocyte R7G, alone (i.e., ones in which the cDNAs encoding G proteins were not applied).

To further, define the G-protein associations with this lymphocyte R7G the inventors will employ antibodies against specific G-protein subunits and determine whether these antibodies block receptor function (PI and cAMP formation). A number of laboratories have described antibodies that recognize specific G protein subunits and many are now commercially available. Such antibodies have been used to study the interaction of the thyrotrophin-releasing hormone (TRH) receptor with specific Gαq and Gsα subunits. The inventors' studies will be carried out using membranes prepared from CHO cell transformants and from human T and B lymphocytes. Aliquots of the membranes (prepared as described for FIG. 10 and elsewhere) will be incubated (a) with and without antisera to specific G-protein subunits and (b) with MET-ENK, DPDPE and other opiate/opioid ligands. PI and cAMP will be quantitated for the samples and the effects of the antibodies on these second messengers determined by comparisons between the antibody treated and nontreated controls. Basal levels will be measured for samples incubated in buffer, alone and non-stimulated (but antibody-treated) controls.

In follow-up studies the inventors will use an immuno-precipitation approach employing antisera directed against G-protein subunits to identify the specific G proteins that co-precipitate with the lymphocyte receptor in CHO transfectants and in T and B lymphocytes. Since it is possible that the G proteins expressed in lymphocytes are different from those in CHO cells our studies will include T and B cells as well as the transfected CHO cells. For these studies it will be necessary to first demonstrate ligand- binding to solubilized receptors. For this purpose cells will be disrupted and solubilized in CHAPs containing buffer, and then following steps to concentrate the membrane receptors and remove the detergent, receptor-binding will be measured using an appropriate labeled ligand (e.g., $^{125}$I-DADLE). Controls for these studies will include membranes prepared from mock transformed CHO cells and lymphocytes which do not express the lymphocyte receptor (defined from RNA blot analysis and receptor-ligand assays). If specific binding is demonstrated (i.e., high affinity binding for the preparations obtained from cells that express the receptor and low non-specific binding obtained with preparations from nonexpressing cells) the inventors will then immunoprecipitate the receptor-G protein complexes. Aliquots of the receptor preparations will be incubated with specific anti-sera against the G proteins. Receptor binding will then be quantitated for the precipitates. Western blotting will be employed for confirming the presence or absence of G-protein subunits in precipitates. This technique has been employed to show that Giα3 and Goα associate with somatostatin receptors of the SSTR2 subtype (Law et al). Once the inventors have produced monoclonal antibodies to the lymphocyte receptor the inventors will employ these antibodies for immunoprecipitations of the lymphocyte-G protein complexes.

From these studies the inventors expect to (a) determine whether the novel lymphocyte R7G signals via phosphoinositol hydrolysis and $[Ca^{2+}]_i$ and (b) define its activity in terms of the association(s) with G-proteins. These studies will identify the classes of G-proteins that couple to the receptor. This information is needed to correlate the protein sequences of the receptor (i.e., those which make-up the cytoplasmic loops) with the classes of G-proteins that associate with it.

B. Mapping of regions within the EBI1 receptor that define its association(s) with G proteins.

Amino acid substitution will be carried out in regions of EBI1 which do not interfere with receptor-ligand binding. After transfection in COS or other mammalian cells opiate/opioids will be applied and second messengers assayed. PI will be assessed from $[Ca^{2+}]i$. and cAMP will be measured. PI will be measured from $^3$H-inositol labeling, cAMP by RIA and $[Ca^{2+}]i$ from Fura-2 fluorescence. The effect of mutations on function (s) will be determined by comparisons between the mutant and wild-type proteins. Receptor domains that direct interaction with the Gqα subunits (PI and $[Ca^{2+}]_i$ signaling) and Gαs or Gi subunits (cAMP formation) will be identified; specific amino acid substitutions will be correlated with decreased function. From these studies the inventors expect to map regions within the novel lymphocyte R7G that direct its association(s) with G proteins.

1. Rationale

Considerable evidence suggests that a conserved Asp residue present in the TM2 of most G protein-coupled receptors plays a pivotal role in mediating the conformational changes associated with receptor activation (Milligan). Recent studies have linked mutations in G-protein coupled receptors with the development of certain tumors and inherited diseases. For example, Parma et al. (1993) described mutations in two different residues (Asp619 and Ala 623) within the carboxyl-terminal portion of the third cytoplasmic loop of the thyrotropin receptor that confers constitutive activation of adenylyl cyclase; such mutations are thought to be responsible for the development of some hyperfunctioning thyroid adenomas. In another study Shenker et al. (1993) reported that a point mutation in the sixth transmembrane region of the luteinizing hormone receptor results in the substitution of Asp 578 to Gly and constitutive upregulation in adenylyl cyclase activity; this aberrant activity has been correlated with the gonadotropin-independent disorder familial male precocious puberty. These recent findings highlight the profound effects that can be affected by single point mutations and underscore the importance of carrying out studies to identify the functional domains of G-protein-associated receptors.

2. Methods

Using methods similar to those described above for example 6 (e.g., the Altered Sites in vitro mutagenesis system; Promega LKB Biotechnology Inc.; Kong et al., 1993) the inventors will induce point (single) mutations in the cloned lymphocyte receptor. Substitutions will be made at sites which leave intact the binding domains which the inventors have previously identified. These replacements will be confirmed by DNA sequencing. Mutated and wild-type cDNA will be transfected in COS and/or CHO cells and expression confirmed by RNA blot analysis. After transfection, the cells will be stimulated with MET-ENK and a panel of other appropriate opiate receptor agonists (i.e., those that our studies show to bind to this receptor, see IA, above). In subsequent studies receptor antagonists will be employed to map the inhibitory activity that these agents exert on mutant receptors; opiate/opioid effects will be measured in the presence of inhibitors (e.g., naloxone, naltrindole). The inventors will measure (a) the release of inositol phosphates, (b) $[Ca^{2+}]_i$ and (c) adenylyl cyclase activity as described above for IIA. The effects of the mutations on activity will be determined from comparisons between cells transfected with wild-type and mutant receptors. The receptor domains that direct interactions with the Gqa subunits will be identified by the correlation of specific substitutions and a decrease in inositol phosphates and $[Ca^{2+}]_i$ signaling. Similarly, the receptor structure that directs the interactions with Gas subunits will be identified by correlation of sequence and a decrease in cAMP production.

3. Expected results and future studies

It should be noted that it is possible that some replacements could, at least in theory, result in alterations in the receptor specificity for G proteins. For example, it is possible that the studies will show that the wild-type receptor associates with Gαs subunits but that certain mutant receptors interact with Gi or Go subunits. Such interactions would be indicated in our assays by opiate/opioid induced inhibition of adenylyl cyclase (i.e., decrease in cAMP content). If the inventors find that opiate/opioid activation of any mutant receptor results in the decrease in cAMP content the inventors will then identify the G protein subunits that associate with the mutant and compare these findings with those for the wild-type. The G-protein associations with the mutant receptor(s) will be further defined using antibodies against specific G-protein subunits. Using methods described above the inventors will prepare membranes from cells transfected with wild-type and mutant cDNA's. Aliquots of these membranes will then be incubated (a) with and without antisera to the specific G-protein subunits and (b) with MET-ENK, DPDPE and other opiate/opioid ligands. cAMP will be assayed and the effects of the antibodies on these second messengers determined by comparisons between the antibody treated and nontreated controls. Once studies using immunoprecipitation with specific antisera directed against the G-protein subunits have been successful in identifying the G proteins that associate with the wild type receptor the inventors will then also utilize this approach for defining the G proteins that associate (co-precipitate) with the mutant receptors.

From these studies the inventors expect to map regions within the novel lymphocyte receptor that direct its association with G proteins.

EXAMPLE 8

Cloning of other novel opioid binding proteins and elucidation of their nucleotide and peptide structures.

Three general approaches utilizing reverse-transcriptase (RT)/polymerase chain reactions (PCR) will be employed. Pairs of degenerate, synthetic oligonucleotides corresponding to sequences of EBI1 will be used as primers. The first approach will employ poly (A)+ RNA from distinct lymphoid sources (e.g., activated and nonactivated $CD4^+$ lymphocytes). In the second approach PCR methods will be used for the amplification of mouse and human cDNA libraries. For the third approach human and mouse genomic DNA and low stringency PCR amplification will be employed. With all three approaches PCR products (prospective clones) will be sequenced. Clones of interest will be analyzed, cloned into expression vectors, and expressed in mammalian cells. Protein binding specificity and signaling pathways will be identified using the methods described above for examples 6 and 7. From these studies the inventors expect to identify additional novel members of a lymphocyte R7G family of opioid/opiate binding proteins.

1. Rationale

The human genome may have as many as 1000 genes that encode G protein coupled receptors. All members of this superfamily are thought to share certain structural features (i.e., all have seven transmembrane domains). Graul and Sadee have proposed that the R7G genes encoding this R7G superfamily are composites of ancestral gene fragments that were joined as multiple repeats and subsequently shuffled giving rise to a number of diverse subfamilies. Their examination of known receptor sequences supports the notion that gene segments have been exchanged between rather distantly related subfamilies. If this hypothesis is correct then one would predict the existence of chimeras composed of the parts of two or more other receptor subfamilies. Such hybrid receptors could, at least in theory have extracellular binding sites homologous to one subfamily (e.g., opiate receptor) but the intracellular regions similar to another subfamily (e.g., angiotensin receptor). This hypothesis may help to explain the rather marked similarities that have been observed for the sequences identified for CNS opioid receptors and those ascertained for the chemotactic (e.g., fMET-LEU-PHE, IL-8) receptors of immune cells.

The inventors have a identified a novel lymphocyte R7G receptor which has some degree of similarity to opiate receptors, IL-8 receptors and to angiotensin receptors. This novel receptor may be only one member of a large family of closely related receptors that have important roles in immune regulation as well as other physiological functions. For these reasons the inventors propose to clone other closely related receptors. The availability of cDNA and genomic libraries as well as the advances in reverse transcriptase (RT)/polymerase chain reactions (PCR) methods make this a feasible goal. The inventors will employ three different approaches for the identification of new members of this lymphocyte R7G family; these methods have been used successfully by other investigators for the cloning of other members of this superfamily.

2. Methods

All three general approaches will be employed. In the first approach amplify poly(A)+ RNA will be prepared from distinct lymphocyte populations (e.g., activated and nonactivated human peripheral blood and murine spleen CD4 and CD8 lymphocytes and B cells) and amplified using PCR methods. These PGR products will then be reverse transcribed by reverse transcriptase and PCR carried out on single stranded cDNA. The PCR products will be treated with T4 DNA polymerase and digested with EcoRI. DNA will be kinased and cloned into pBluescript. Recombinant clones will be analyzed by sequencing. Appropriate clones will be selected, then $^{32}$P-labeled for use as probes and the screening of commercially available genomic libraries. The inventors will use hybridization and Southern blot analysis to identify prospective clones. For subcloning, and additional analysis the DNA's of interest will be inserted into pUC18 and nucleotide sequence analysis will be carried out.

In the event that the inventors are unsuccessful in this first approach the inventors will then employ PCR methods to amplify mouse and human lymphocyte cDNA libraries. PCR products will be size-selected and cloned in M13 mp18 and sequenced. The PCR products encoding lymphocyte-like receptor sequences will then be $^{32}$P-labeled and used to screen the lymphocyte libraries. Prospective clones will be identified using standard hybridization methods.

If neither of the above methods yield promising results the inventors will then employ a third approach. The inventors will use human and mouse genomic DNA and low stringency PCR amplification. PCR products will be cloned into phage M13 and sequenced. PCR products of interest will then be $^{32}$p labeled and used as probes for screening lymphocyte cDNA libraries. Prospective clones will be selected using standard hybridization methods.

Once the inventors have identified a prospective receptor clone the inventors will then define its properties. Such prospective receptor clones will be subjected to sequence analysis; nucleotide sequences will be determined and compared with known sequences for other proteins. Based upon these analyses the inventors will then make predictions about protein structure and function. Subsequently, HindIII-Pst1 fragments that contain the coding regions receptors will be subcloned into plasmids (e.g., pSVL) for transfecting COS-7 cells and/or subcloned into pRc/CMV for transforming CHO cells. Ligand-receptor binding and signaling functions will be defined using a panel of potential ligands (e.g., opiates/opioids, somatostatin, other neuropeptides, IL-8 angiotensin).

The inventors expect these studies to identify novel members of a lymphocyte R7G family of opioid/opiate binding proteins. In future studies the inventors will define the ligand binding and functional domains of these novel proteins.

In other studies the inventors will produce monoclonal antibodies specific for the novel lymphocyte R7G and any other such receptors identified. Also, the inventors will define the functional effect(s) e.g., migration, differentiation, proliferation that opiates/opioids mediate via this family of lymphocyte receptors and determine how their expression regulates immune responses to other stimuli i.e., lectins, antigens, lymphokines.

REFERENCES

Aramori, I. and S. Nakanishi, S. 1992. Coupling of two endothelin receptor subtypes to differing signal transduction in transfected Chinese hamster ovary cells. *J. Biol. Chem.* 267(18):12468-74.

Adelman et al. (1983) *DNA* 2: 183.

Bender, J. G., D. E. v. Epps and D. E. Chemoweth. 1987. Independent regulation of human neutrophil chemotactic receptors after activation. *J. Immunol.* 139: 3028-3033.

Bergelson, J. M., M. P. Shepley, B. M. C. Chan, M. E. Hemler and R. W. Finberg. 1992. Identification of the integrin VLA-2 as a receptor for Echovirus, 1. *Science.* 255: 1718.

Birkenbach, M., K. Josefsen, R. Yalamanchili, G. Lenoir and E. Kieff. 1993. Epstein-barr virus-induced genes: first lymphocyte-specific G protein coupled peptide receptors. *J. Virol.* 67: 2209-2220.

Bolivar et al. (1977) *Gene*, 2: 95.

Borboni, P., G. D. G. Sesti, M. A. Marini, P. D. Porto, M. S. G. Montani, R. Lauro and R. D. Pirro. 1989. b-endorphin receptors on cultured and freshly isolated lymphocytes from normal subjects. *Biochem. Biophys. Res. Commun.* 163: 642-648.

Boshart et al. (1985) *Cell* 41: 521.

Bradbury, L. E., V. S. Goldmacher and T. F. Tedder. 1993. The CD19 signal transduction complex of B lymphocytes: deletion of the CD19 cytoplasmic domain alters signal transduction but not complex formation with TAPA-1 and Leu 13. *J. Immunol.* 151: 2915.

Bryant, H. U., B. C. Yoburn, C. E. Intunisi, E. W. Bernton and J. W. Holaday. 1988. Morphine-induced immunomodulation is not related to serum morphine concentrations. E. *J. Pharmacol* 6: 165.

Carr, D. J. J., C. H. Kim, B. d. Costa, A. E. Jacobson, K. C. Rice and J. E. Blalock. 1988. Evidence for a d-class opioid receptor on cells of the immune system. *Cell. Immunol.* 116: 44-51.

Chang et al. (1978) *Nature*, 375: 615.

Chang, H. C., P. Moingeon, P. Lopez, H. Krasnow, C. Stebbins and E. L. Reinherz. 1989. Dissection of the human CD2 intracellular domain. *J. Exp. Med.* 169: 2073-2083.

Chang, K. J., R. J. Miller and P. Cuatrecasas. 1978. Interaction of enkephalin with opiate receptors in intact cultured cells. *Mol. Pharmoc.* 14: 961-970.

Chao, C. C., B. M. Sharp, C. Pomeroy, G. A. Filice and P. K. Peterson. 1990. Lethality of Morphine in Mice infected with Toxoplasma gondii. *J. Pharmacol. Exp. Ther.* 252: 605-609.

Cook, S. J. and F. McCormick. 1993. Inhibition by cAMP of ras-dependent activation of raf. *Science* 262: 1069-72.

Corbett, A. D., M. G. C. Gillan, H. W. Kosterlitz, A. T. McKnight, S. J. Paterson and L. E. Robson. 1984. Selectivities of opioid peptide analogues as agonists and antagonists at the d-receptor. *Br. J. Pharmacol* 83: 271.

Crea et al. (1978) *Proc. Natl. Acad. Sci. U.S.A*, 75: 5765.

Cunnick, J., E., D. Lysle, B. Kucinski and B. Rabin. 1992. Stress-induced alteration of immune function. Diversity of effects and mechanisms. *Ann. N. Y. Acad. Sci.* 650: 283.

Ebener, U., S. Wehner, J. Cinatl, E. S. Gussetis and B. Kornhuber. 1990. Expression of markers shared between human hematopoietic cells and neuroblastoma cells. *Anticancer Res.* 10: 887.

Falke, N. E. and E. G. Fischer. 1985. Cell shape of polymorphonuclear leukocytes is influenced by opioids. *Immunobiology.* 169: 532.

Felten, D. L., S. Y. Felten, D. L. Bellinger and e. al. 1987. Noradrenergic sympathetic neural interactions with the immune system: structure and function. *Immunol. Rev.* 100: 225.

Ferruti and Tanzi (1986) *Cris. Rev. Ther. Drug Carrier Syst.* 2: 117-136.

Fiers et al. (1978) *Nature* 273: 113.

Fischer, E. G. 1988. Opioid peptides modulate immune functions. *Immunopharmacol. Immunotoxicol.* 10: 265-326.

Fischer, E. G. 1988. Opioid peptides modulate immune functions. *Immunopharmacol. Immunotoxicol.* 10: 265.

Foris, G., G. A. Medgyesi, J. T. Nagy and Z. Varga. 1987. Concentration-dependent effect of met-enkephalin on human polymorphonuclear leukocytes. *Ann. N.Y. Acad. Sci.* 496: 151.

Forsyth, K. D. 1991. Anti-CD9 antibodies augment neutrophil adherence to endothelium. *Immunol.* 72: 292.

Gabizon et al. (1990) *Cancer Res.* 50: 6371–6378.

Gilmore, W., M. Moloney and L. P. Weiner. 1990. The role of opioid peptides in immunomodulation. *Ann. N.Y. Acad. Sci.* 597: 252–263.

Goeddel et al. (1980) *Nucleic Acids Res.,* 8: 4057.

Goeddel et al. (1979) *Nature,* 281: 544.

Heagy, W., M. A. Shipp and R. W. Finberg. 1992. Opioid receptor agonists and $Ca^{2+}$ modulation in human B cell lines. *J. Immunol.* 149: 4074–4081.

Heagy, W., M. Laurance, E. Cohen and R. Finberg. 1990. Neurohormones regulate T cell function. *J. Exp. Med.* 171: 1625–1633.

Heagy, W., K. Duca and R. Finberg. Opioid peptides: Chemotactic factors which modulate expression of CD9 on pre-B leukemic cells. manuscript in preparation.

Heijnen, C. J., A. Kavelaars and R. E. Ballieux. 1991. B-endorphin: cytokine and neuropeptide. *Immunol Rev* 119: 41–63.

Hemler, M., 1990. VLA proteins in the integrin family: structures, functions and their role in leukocytes. *Ann. Rev. Immunol.* 8: 365.

Hermans, M. H. A., H. Hartsuiker and D. Opstelten. 1989. An in situ study of B-lymphocytopoiesis in rat bone marrow. Topographical arrangement of terminal deoxynucleotidyl transferase-positive Cells. *J. Immunol.* 142: 67.

Hess et al. (1968) *J. Adv. Enzyme Reg.* 7: 149.

Hitzeman et al. (1980) *J. Biol. Chem.* 255: 2073.

Holland et al. (1978) *Biochemistry* 17: 4900.

Ikeyama, S., M. Koyama, M. Yamaoko, R. Sasada and M. Miyake. 1993. Suppression of cell motility and metastasis by transfection with human motility-related protein (MRP-1/CD9) DNA. *J. Exp. Med.* 177: 1231.

Imai, T. and O. Yoshie. 1993. C33 antigen and M38 antigen recognized by monoclonal antibodies inhibitory to syncytium formation by human T cell leukemia virus type 1 are both members of the transmembrane 4 superfamily and associate with each other and with CD4 or CD8 in T cells. *J. Immunol.* 151: 6470.

Itakura et al. (1977) *Science,* 198: 1056.

Jones (1977) *Genetics* 85: 12.

Kharkevich, D. D. and Z. G. Kadagidze. 1989. The effect of the stimulation of opioid receptors on lymphocyte functional activity in vivo. *Biulleten Eksperimentalnoi Biologii I Meditsinyy.* 108: 315.

Kingsman et al. (1979) *Gene* 7: 141.

Komada, Y., H. Ochiai, K. Shimizu, E. Azuma, H. Kamiya and M. Sakurai. 1992. Shedding of CD9 antigen into cerebrospinal fluid by acute lymphoblastic leukemia cells. *Blood.* 76: 112.

Kong, H., K. Raynor, K. Yasuda, S. T. Moe, P. S. Protoghese, G. I. Bell and T. Reisine. 1993. A single residue, aspartic acid 95, in the δ opioid receptor specifies selective high affinity agonist binding. *J. Biol. Chem.* 268(331): 23055–58.

Kruse and Patterson, eds. (1973) Tissue Culture, Academic Press.

Kyte and Doolittle (1982) *J. Mol. Biol.* 157: 105.

Ledbetter, J. A., C. H. June, L. S. Grosmaire and P. S. Rabinovitch. 1987. Crosslinking of surface antigens causes mobilization of intra-cellular ionized calcium in T-lymph. *Proc. Natl. Acad. Sci. USA* 84: 1384–1388.

Letarte, M., J. G. Seehafer, A. Greaver, A. Masellis-Smith and A. R. E. Shaw. 1993. Homotypic aggregation of pre-B leukemic cell lines by antibodies to VLA integrins correlates with their expression. *Leukemia.* 7: 93.

Lu, F. C., W. A. Mannell, H. C. Grice and M. G. Allmark. 1960. The effects of agranulocytic and nonagranulocytic drugs in rabbits concurrently treated with busulfan (myleran) III. Thiouracil, morphine, and penicillin. *Toxicology and Applied Pharmacology.* 2: 171.

Madden, J. J., R. M. Donahne, J. Zwemir-Collins, D. A. Shafer and A. Falek. 1987. Binding of naloxone to human T-lymphocytes. *Biochem. Pharmacol.* 36: 4103–4109.

Maneckjee, R. and J. D. Minna. 1992. Nonconventional opioid binding sites mediate growth inhibitory effects of methadone on human lung cancer cells. *Proc. Natl. Acad. Sci. USA.* 89: 1169.

Manzanares, J., K. J. Lookingland and K. E. Moore. 1990. Kappa-opioid-receptor-mediated regulation of a-melanocyte-stimulating hormone secretion and tuberohypophyseal dopaminergic neuronal activity. *Neuroendocrinology.* 52: 200.

Messing et al. (1981) *Third Cleveland Symposium on Macromolecules and Recombinant DNA,* Walton, Ed. (Elsevier, Amsterdam).

Mitamura, T., R. Iwamoto, T. Umata, T. Yomo, I. Urabe and M. Tsuneoka. 1992. The 27-kD diphtheria toxin receptor-associated protein (DRAP27) from vero cells is the monkey homologue of human CD9 antigen: expression of DRAP27 elevates the number of diphtheria toxin receptors on toxin-sensitive cells. *J. Cell. Biol.* 1992: 1389.

Miyake, M., M. Koyama, M. Seno and S. Ikeyama. 1991. Identification of the motility-related protein (MRP-1), recognized by monoclonal antibody M31-15, which inhibits cell motility. *J. Exp. Med.* 174: 1347.

Moore, T. C. 1984. Modification of lymphocyte traffic by vasoactive neurotransmitter substances. *Immunol.* 52: 511.

Munson, P. J. and D. Rodbard. 1980. Ligand: A versatile computerized approach for characterization of ligand binding systems. *Anal. Biochem.* 107: 220–239.

Munson, P. J., Heterogenous receptors and binding analysis in neurobiology. P. J. Marangos, I. C. Campbell, R. M. Cohen, Eds., Brain Receptor Methodologies (Academic Press, New York, 1984).

Nakajima, Y., K. Tsuchida, M. Negishi, S. Ito and S. Nakanishi. 1992. Direct linkage of three tachykinin receptors to stimulation of both phosphatidylinositol hydrolysis and cyclic AMP cascade in transfected Chinese hamster ovary cells. *J. Biol. Chem.* 267: 2437–2442.

Nilsson, K. and G. Klein. 1982. Phenotypic and cytogenetic characteristics of human B-lymphoid cell lines and their relevance for the etiology of Burkitt's lymphoma. *Adv. Cancer Res.* 37: 319.

Novick, D. M., M. Ochshorn, V. Ghali, T. S. Croxson, W. D. Mercer, N. Chiorazzi and M. J. Kreek. 1989. Natural killer cell activity and lymphocyte subsets in parenteral heroin abusers and long-term methadone maintenance patients. *J. Pharmacol. Exp. Ther.* 250: 606–610.

Okayama et al. (1983) *Mol. Cell Biol.* 3: 280.

Ott, S., T. Costa and A. Herz. 1989. Opioid receptors of neuroblastoma cells are in two domains of the plasma membrane that differ in content of G proteins. *J. Neurochem.* 52: 619–626.

Parma, J., L. Duprez, J. Van Sande, P. Cochaux, C. Gervy, J. Mockel, J. Dumont and G. Vassart. 1993. Somatic mutations in the thyrotropin receptor gene cause hyperfunctioning thyroid adenomas. *Nature* 365: 649–651.

Pasternak, G. W. 1993. Pharmacological mechanisms of opioid analgesics. *Clin. Neuropharmacol.* 16: 1.

Pasternak, G. W. 1988. Multiple morphine and enkephalin receptors and the relief of pain. *J. Am. Med. Assoc.* 259: 1362–1366.

Porreca, F., A. E. Takemori, M. Sultana, P. S. Portoghese, W. D. Bowen and H. I. Mosberg. 1992. Modulation of μ-mediated antinociception in the mouse involves opioid d-2-receptors. *J. Pharmacol. Exp. Ther.* 263: 147–152.

Rabinovitch, P. S., C. H. June, A. Grossmann and J. A. Ledbetter. 1986. Heterogeneity among T cells in intracellular free calcium responses after mitogen stimulation with PHA or anti-CD3. Simultaneous use of indo-1 and immunofluorescence with flow cytometry. *J. Immunol.* 137: 952–961.

Radulescu, R. T., B. R. DeCosta, A. E. Jacobson, K. C. Rice, J. E. Blalock and D. J. J. Carr. 1991. Biochemical and functional characterization of a μ-opioid receptor binding site on cells of the immune system. *Prog in NeuroEndocrinImmunology* 4: 166–179.

Ranade (1989) *J. Clin. Pharmacol.* 29: 685–694.

Rubinstein, E., P. Benoit, M. Billard, S. Plaisance, M. Prenant, G. Uzan and C. Boucheix. 1993. Organization of the human CD9 gene. *Genomics.* 16: 132.

Ruff, M. R. and C. B. Pert, 1987. Human monocyte chemotaxis to neuropeptides. In Hypothalamic Dysfunction in Neuropsychiatric Disorders. D. Nerozzi, F. Goodwin and E. Costa, editors. Raven Press. New York. 247–260.

Saland, L. C., D. E. V. Epps, E. Ortiz and A. Samora. 1983. Acute injections of opiate peptides into the rat cerebral ventricle: a macrophage-like cellular response. *Res. Bulletin.* 10: 523.

Sambrook et al. (1989) Molecular Cloning: A Laboratory Manual (Cold Spring Harbor Laboratory Press, Cold Spring Harbor, N.Y.). Seeburg (1982) *DNA* 1: 239.

Seehafer, J. G. and A. R. Shaw. 1991. Evidence that the signal-initiating membrane protein CD9 is associated with small GTP-binding proteins. *Biochem. Biophys. Res. Commun.* 179: 401.

Shavit, Y., G. W. Terman, F. C. Martin, J. W. Lewis, J. C. Lieberkind and R. P. Gale. 1985. Stress, opioid peptides, the immune system, and cancer. *J. Immunol. (Suppl).* 135: 834.

Shenker, A., L. Laue, S. Kosugi, J. J. Merendino, Jr., T. Minegishi and G. B. Cutler, Jr. 1993. A constitutively activating mutation of the luteinizing hormone receptor in familial male precocious puberty. *Nature* 365: 652–54.

Shimizu, Y., W. Newman, Y. Tanaka and S. Shaw. 1992. Lymphocyte interactions with endothelial cells. *Immunol. Today.* 13: 106.

Shipp, M. A., J. Vijayaraghavan, E. V. Schmidt, E. L. Masteller, L. D'Adamio, L. B. Hersh and E. L. Tempel. 1989. Common acute lymphoblastic leukemia antigen (CALLA) is active neutral endopeptidase 24.11 ("enkephalinase"): direct evidence by cDNA transfection analysis. *Proc. Natl. Acad. Sci. USA.* 86: 297.

Shipp, M. A., G. B. Stefano, L. D'Adamio, S. N. Swetzer, F. D. Howard, J. Sinisterra, B. Scharrer and E. L. Reinherz. 1990. Down regulation of enkephalin-mediated inflammatory responses by CD10/neutral endopeptidase 24.11. *Nature.* 347: 394.

Sibinga, N. E. S. and A. Goldstein. 1988. Opioid peptides and opioid receptors in cells of the immune system. *Ann. Rev. Immunol.* 6: 219–249.

Siebwenlist et al. (1980) *Cell* 20: 269.

Sklar, L. A., Z. G. Oades and D. A. Finney. 1984. Neutrophil degranulation detected by right angle light scattering: spectroscopic methods suitable for simultaneous analyses of degranulation or shape change, elastase release, and cell aggregation. *J. Immunol.* 133: 1483.

Slupsky, J. R., J. G. Seehafer, S. C. Tang, A. Masellis-Smith and A. R. E. Shaw. 1989. Evidence that monoclonal antibodies against CD9 antigen induce specific association between CD9 and the platelet glycoprotein IIb-IIIa complex. *J. Biol. Chem.* 264: 12289.

Springer, T. A. 1990. Adhesion receptors of the immune system. *Nature.* 346: 425.

Stein, C., A. H. S. Hassan, K. Lehrberger, J. Giefing and A. Yassouridis. 1993. Local analgesic effect of endogenous opioid peptides. *The Lancet.* 342: 321.

Stinchcomb et al., (1979) *Nature*, 282: 39.

Taub, D. D., T. K. Eisenstein, E. B. Geller, M. W. Adler and T. J. Rogers. 1991. Immunomodulatory activity of mu- and kappa-selective opioid agonists. *Proc. Natl. Acad. Sci. USA* 88: 360–364.

Thomsen et al. (1984) *PNAS* 81: 659.

Traynor, J. R. and J. Elliott. 1993. d-opioid receptor subtypes and cross-talk with p-receptors. *Trends in Pharmac. Sci.* 14: 84–86.

Tschemper et al., (1980) *Gene* 10: 157.

Vaughn, L. K., W. S. Wire, P. Davis, Y. Shimohigashi, G. Toth, R. J. Knapp, V. J. Hruby, T. F. Burks and H. I. Yamamura. 1990. Differentiation between rat brain and mouse vas deferens d opioid receptors. *European J. Pharmacol.* 177: 99.

Wardlaw, S. L., W. B. Wehrenberg, M. Ferin, P. W. Carmel and A. G. Frantz. 1980. High levels of b-endorphin in hypophyseal portal blood. *Endocrinology.* 106: 1323.

Wess, J. 1993. Molecular basis of muscarinic acetylcholine receptor function. *TIPS.*

Wu, D., G. J. LaRosa and M. I. Simon. 1993. G protein-coupled signal transduction pathways of interleukin-8. *Science* 261: 101–3.

Wybran, J. T., T. Appelboom, J. P. Famaey and A. Govaerts. 1979. Suggestive evidence for receptors for morphine and methionine-enkephalin on normal human blood T lymphocytes. *J. Immunol.* 123: 1068.

Yasada, K., K. Raynor, H. Kong, C. Breder, J. Takeda, T. Reisine and G. Bell. 1993. Cloning and functional comparison of κ and δ opioid receptors from mouse brain. *Proc. Natl. Acad. Sci. USA* 90: 6737–6740.

Yatomi, Y., Y. Ozaki, K. Satoh and S. Kume. 1993. Anti-CD9 monoclonal antibody elicits staurosporine inhibitable phosphatidylinositol 4,5-bisphosphate hydrolysis, phosphatidylinosital 3,4-bisphosphate synthesis, and protein-tyrosine phosphorylation in human platelets. *FEBS Lett.* 322: 285.

Ye, S., R. R. Applegreen, J. M. Davis and H. T. Cheung. 1989. Modulation of lymphocyte motility by b-endorphin and metenkephalin. *Immunopharmnacology.* 17: 81.

Zagon, I. S. and P. J. McLaughlin. 1987. Modulation of murine neuroblastoma in nude mice by opioid antagonists. *J. Natl. Cancer Inst.* 78: 141.

Zola, H., V. Furness, S. Barclay, H. Zowtyj, M. Smith, J. V. Melo, S. H. Neoh and J. Bradley. 1989. The p24 leucocyte membrane antigen: modulation associated with lymphocyte activation and differentiation. *Immunol. Cell. Biol.* 67: 63.

What is claimed is:

1. A process of screening a candidate substance for its ability to interact with a lymphocyte receptor said process comprising:

a) providing a lymphocyte receptor protein having an amino acid sequence as contained in SEQ ID NO:2;

b) selecting a candidate substance having a chemical structure or biological activity suggestive of an ability to mimic the biological activity of an opiate, opioid drug or opioid peptide having a known binding affinity to the lymphocyte receptor protein; and c) testing the ability of a selected candidate substance to interact with said lymphocyte receptor protein.

2. A process of screening a candidate substance for its ability to interact with a lymphocyte receptor, said process comprising:

a) providing a lymphocyte receptor protein by (i) transfecting a host cell with a nucleotide sequence contained in SEQ ID NO:1 so as to form a transformed cell effective for encoding a lymphocyte receptor polypeptide, and (ii) maintaining said transformed cell under biological conditions sufficient for translation of said nucleotide sequence so as to express said lymphocyte receptor polypeptide:

b) selecting a candidate substance having a chemical structure or biological activity suggestive of an ability to mimic the biological activity of an opiate, opioid drug or opioid peptide having a known binding affinity to the lymphocyte receptor protein; and c) testing the ability of a selected candidate substance to interact with said lymphocyte receptor protein.

3. The process according to claim 1, wherein providing said lymphocyte receptor polypeptide having an amino acid sequence as contained in SEQ ID NO 2, comprises (i) transfecting a host cell with a polynucleotide that encodes the lymphocyte receptor polypeptide having an amino acid sequence as contained in SEQ ID NO.2 to form a transformed cell, and (ii) maintaining said transformed cell under biological conditions sufficient for expression of said lymphocyte receptor polypeptide.

4. A process of making a product having an ability to interact with a lymphocyte receptor said process comprising:

a) providing a lymphocyte receptor polypeptide having an amino acid sequence as contained in SEQ ID NO:2;

b) selecting a candidate substance having a chemical structure or biological activity suggestive of an ability to mimic the biological activity of an opiate, opioid drug or opioid peptide having a known binding affinity to the lymphocyte receptor polypeptide:

c) testing the ability of selected candidate substance to interact with said lymphocyte receptor polypeptide; and d) providing a product of a candidate substance established in step c to interact with the lymphocyte receptor polypeptide.

5. The process according to claim 4, wherein providing said lymphocyte receptor polypeptide having an amino acid sequence as contained in SEQ ID NO:2, comprises (i) transfecting a host cell with a polynucleotide that encodes the lymphocyte receptor polypeptide having an amino acid sequence as contained in SEQ ID NO:2 to form a transformed cell and (ii) maintaining said transformed cell under biological conditions sufficient for expression of said lymphocyte receptor polypeptide having an amino acid sequence as contained in SEQ ID NO 2.

6. A process of making a product having an ability to interact with a lymphocyte receptor, said process comprising:

a) providing a lymphocyte receptor protein by (i) transfecting a host cell with a nucleotide sequence contained in SEQ ID NO:1 so as to form a transformed cell effective for encoding a lymphocyte receptor polypeptide, and (ii) maintaining said transformed cell under biological conditions sufficient for translation of said nucleotide sequence and expression of said lymphocyte receptor polypeptide;

b) selecting a candidate substance having a chemical structure or biological activity suggestive of an ability to mimic the biological activity of an opiate, opioid drug or opioid peptide having a known binding affinity to the lymphocyte receptor polypeptide;

c) testing the ability of a selected candidate substance to interact with said lymphocyte receptor polypeptide; and d) providing a product of a candidate substance established in step c to interact with the lymphocyte receptor polypeptide.

7. A process of screening a substance for its ability to interact with an immune-cell specific lymphocyte receptor and a neuronal type opioid receptor, said process comprising:

a) providing an immune-cell specific lymphocyte receptor polypeptide having an amino acid sequence as contained in SEQ ID NO:2.

b) testing the ability of a substance to interact with said immune-cell specific lymphocyte receptor;

c) providing a neuronal type opioid receptor polypeptide; and d) testing the ability of said substance to interact with said neuronal type opioid receptor polypeptide.

8. A process of screening a substance for its ability to interact with an immune-cell specific lymphocyte receptor and a neuronal type opioid receptor, said process comprising:

a) providing an immune-cell specific lymphocyte receptor polypeptide by (i) transfecting a host cell with a nucleotide sequence contained SEQ ID NO:1 so as to form a transformed cell effective or encoding an immune-cell specific lymphocyte receptor polypeptide and (ii) maintaining said transformed cell under biological conditions sufficient for translation of the nucleotide sequence and expression of said immune-cell specific lymphocyte receptor polypeptide;

b) testing the ability of a substance to interact said immune-cell specific lymphocyte receptor;

c) providing a neuronal type opioid receptor polypeptide; and d) testing the ability of said substance to interact with said neuronal type opioid receptor polypeptide.

9. The process according to claim 8, wherein the expressed immune-cell specific lymphocyte receptor polypeptide has an amino acid sequence a contained in SEQ ID NO:2.

10. The process according to claim 8, wherein the polynucleotide has a nucleotide sequence as contained in SEQ ID NO:1.

11. The process according to claim 7, wherein the neuronal type opioid receptor is a κ, μ, or δ opioid receptor.

12. The process according to claim 7, wherein the step of providing said neuronal type opioid receptor polypeptide comprises (i) transfecting a host cell with a polynucleotide that encodes the neuronal type opioid receptor polypeptide to form a transformed cell, and (ii) maintaining said transformed cell under biological conditions sufficient for expression of said neuronal type opioid receptor polypeptide.

13. The process according to claim 1 wherein the candidate substance is screened for its ability to act as an agonist or antagonist to said lymphocyte receptor protein.

14. The process according to claim 7 wherein the candidate substance is screened for its ability to act as an agonist or antagonist to said immune-cell specific lymphocyte receptor polypeptide.

15. The process according to claim 7 wherein the candidate substance is screened for its ability to act as an agonist or antagonist to said neuronal type opioid receptor polypeptide.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2154 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA"

( i x ) FEATURE:
        ( A ) NAME/KEY: CDS
        ( B ) LOCATION: 64..1197

( x i ) SEQUENCE DESCRIPTION: SEQ ID NO:1:

```
GGAATTCCGT AGTGCGAGGC CGGGCACAGC CTTCCTGTGT GGTTTTACCG CCCAGAGAGC        60

GTC ATG GAC CTG GGG AAA CCA ATG AAA AGC GTG CTG GTG GTG GCT CTC        108
    Met Asp Leu Gly Lys Pro Met Lys Ser Val Leu Val Val Ala Leu
    1               5                  10                  15

CTT GTC ATT TTC CAG GTA TGC CTG TGT CAA GAT GAG GTC ACG GAC GAT        156
Leu Val Ile Phe Gln Val Cys Leu Cys Gln Asp Glu Val Thr Asp Asp
                20                  25                  30

TAC ATC GGA GAC AAC ACC ACA GTG GAC TAC ACT TTG TTC GAG TCT TTG        204
Tyr Ile Gly Asp Asn Thr Thr Val Asp Tyr Thr Leu Phe Glu Ser Leu
                35                  40                  45

TGC TCC AAG AAG GAC GTG CGG AAC TTT AAA GCC TGG TTC CTC CCT ATC        252
Cys Ser Lys Lys Asp Val Arg Asn Phe Lys Ala Trp Phe Leu Pro Ile
        50                  55                  60

ATG TAC TCC ATC ATT TGT TTC GTG GGC CTA CTG GGC AAT GGG CTG GTC        300
Met Tyr Ser Ile Ile Cys Phe Val Gly Leu Leu Gly Asn Gly Leu Val
65                  70                  75

GTG TTG ACC TAT ATC TAT TTC AAG AGG CTC AAG ACC ATG ACC GAT ACC        348
Val Leu Thr Tyr Ile Tyr Phe Lys Arg Leu Lys Thr Met Thr Asp Thr
80                  85                  90                  95

TAC CTG CTC AAC CTG GCG GTG GCA GAC ATC CTC TTC CTC CTG ACC CTT        396
Tyr Leu Leu Asn Leu Ala Val Ala Asp Ile Leu Phe Leu Leu Thr Leu
                100                 105                 110

CCC TTC TGG GCC TAC AGC GCG GCC AAG TCC TGG GTC TTC GGT GTC CAC        444
Pro Phe Trp Ala Tyr Ser Ala Ala Lys Ser Trp Val Phe Gly Val His
                115                 120                 125

TTT TGC AAG CTC ATC TTT GCC ATC TAC AAG ATG AGC TTC TTC AGT GGC        492
Phe Cys Lys Leu Ile Phe Ala Ile Tyr Lys Met Ser Phe Phe Ser Gly
        130                 135                 140

ATG CTC CTA CTT CTT TGC ATC AGC ATT GAC CGC TAC GTG GCC ATC GTC        540
Met Leu Leu Leu Leu Cys Ile Ser Ile Asp Arg Tyr Val Ala Ile Val
145                 150                 155

CAG GCT GTC TCA GCT CAC CGC CAC CGT GCC CGC GTC CTT CTC ATC AGC        588
Gln Ala Val Ser Ala His Arg His Arg Ala Arg Val Leu Leu Ile Ser
160                 165                 170                 175

AAG CTG TCC TGT GTG GGC AGC GCC ATA CTA GCC ACA GTG CTC TCC ATC        636
Lys Leu Ser Cys Val Gly Ser Ala Ile Leu Ala Thr Val Leu Ser Ile
                180                 185                 190

CCA GAG CTC CTG TAC AGT GAC CTC CAG AGG AGC AGC AGT GAG CAA GCG        684
Pro Glu Leu Leu Tyr Ser Asp Leu Gln Arg Ser Ser Ser Glu Gln Ala
                195                 200                 205

ATG CGA TGC TCT CTC ATC ACA GAG CAT GTG GAG GCC TTT ATC ACC ATC        732
```

```
        Met  Arg  Cys  Ser  Leu  Ile  Thr  Glu  His  Val  Glu  Ala  Phe  Ile  Thr  Ile
                  210                     215                     220

CAG  GTG  GCC  CAG  ATG  GTG  ATC  GGC  TTT  CTG  GTC  CCC  CTG  CTG  GCC  ATG         780
        Gln  Val  Ala  Gln  Met  Val  Ile  Gly  Phe  Leu  Val  Pro  Leu  Leu  Ala  Met
             225                     230                     235

AGC  TTC  TGT  TAC  CTT  GTC  ATC  ATC  CGC  ACC  CTG  CTC  CAG  GCA  CGC  AAC         828
        Ser  Phe  Cys  Tyr  Leu  Val  Ile  Ile  Arg  Thr  Leu  Leu  Gln  Ala  Arg  Asn
        240                      245                     250                     255

TTT  GAG  CGC  AAC  AAG  GCC  ATC  AAG  GTG  ATC  ATC  GCT  GTG  GTC  GTG  GTC         876
        Phe  Glu  Arg  Asn  Lys  Ala  Ile  Lys  Val  Ile  Ile  Ala  Val  Val  Val  Val
                            260                     265                     270

TTC  ATA  GTC  TTC  CAG  CTG  CCC  TAC  AAT  GGG  GTG  GTC  CTG  GCC  CAG  ACG         924
        Phe  Ile  Val  Phe  Gln  Leu  Pro  Tyr  Asn  Gly  Val  Val  Leu  Ala  Gln  Thr
                       275                     280                     285

GTG  GCC  AAC  TTC  AAC  ATC  ACC  AGT  AGC  ACC  TGT  GAG  CTC  AGT  AAG  CAA         972
        Val  Ala  Asn  Phe  Asn  Ile  Thr  Ser  Ser  Thr  Cys  Glu  Leu  Ser  Lys  Gln
                  290                     295                     300

CTC  AAC  ATC  GCC  TAC  GAC  GTC  ACC  TAC  AGC  CTG  GCC  TGC  GTC  CGC  TGC        1020
        Leu  Asn  Ile  Ala  Tyr  Asp  Val  Thr  Tyr  Ser  Leu  Ala  Cys  Val  Arg  Cys
             305                     310                     315

TGC  GTC  AAC  CCT  TTC  TTG  TAC  GCC  TTC  ATC  GGC  GTC  AAG  TTC  CGC  AAC        1068
        Cys  Val  Asn  Pro  Phe  Leu  Tyr  Ala  Phe  Ile  Gly  Val  Lys  Phe  Arg  Asn
        320                      325                     330                     335

GAT  ATC  TTC  AAG  CTC  TTC  AAG  GAC  CTG  GGC  TGC  CTC  AGC  CAG  GAG  CAG        1116
        Asp  Ile  Phe  Lys  Leu  Phe  Lys  Asp  Leu  Gly  Cys  Leu  Ser  Gln  Glu  Gln
                            340                     345                     350

CTC  CGG  CAG  TGG  TCT  TCC  TGT  CGG  CAC  ATC  CGG  CGC  TCC  TCC  ATG  AGT        1164
        Leu  Arg  Gln  Trp  Ser  Ser  Cys  Arg  His  Ile  Arg  Arg  Ser  Ser  Met  Ser
                       355                     360                     365

GTG  GAG  GCC  GAG  ACC  ACC  ACC  ACC  TTC  TCC  CCA  TAGGCGACTC  TTCTGCCTGG        1217
        Val  Glu  Ala  Glu  Thr  Thr  Thr  Thr  Phe  Ser  Pro
                  370                     375

ACTAGAGGGA    CCTCTCCCAG    GGTCCCTGGG    GTGGGGATAG    GGAGCAGATG    CAATGACTCA      1277

GGACATCCCC    CCGCCAAAAG    CTGCTCAGGG    GAAAAAGCAG    CTCTCCCCTC    AGAGTGCAAG      1337

CCCCTGCTCC    AGAAGATAGC    TTCACCCCAA    TCCCAGCTAC    CTCAACCAAT    GCCAAAAAAA      1397

GACAGGGCTG    ATAAGCTAAC    ACCAGACAGA    CAACACTGGG    AAACAGAGGC    TATTGTCCCC      1457

TAAACCAAAA    ACTGAAAGTG    AAAGTCCAGA    AACTGTTCCC    ACCTGCTGGA    GTGAAGGGGC      1517

CAAGGAGGGT    GAGTGCAAGG    GGCGTGGGAG    TGGCCTGAAG    AGTCCTCTGA    ATGAACCTTC      1577

TGGCCTCCCA    CAGACTCAAA    TGCTCAGACC    AGCTCTTCCG    AAAACCAGGC    CTTATCTCCA      1637

AGACCAGAGA    TAGTGGGGAG    ACTTCTTGGC    TTGGTGAGGA    AAAGCGGACA    TCAGCTGGTC      1697

AAACAAACTC    TCTGAACCCC    TCCCTCCATC    GTTTTCTTCA    CTGTCCTCCA    AGCCAGCGGG      1757

AATGGCAGCT    GCCACGCCGC    CCTAAAAGCA    CACTCATCCC    CTCACTTGCC    GCGTCGCCCT      1817

CCCAGGCTCT    CAACAGGGGA    GAGTGTGGTG    TTTCCTGCAG    GCCAGGCCAG    CTGCCTCCGC      1877

GTGATCAAAG    CCACACTCTG    GGCTCCAGAG    TGGGGATGAC    ATGCACTCAG    CTCTTGGCTC      1937

CACTGGGATG    GGAGGAGAGG    ACAAGGGAAA    TGTCAGGGGC    GGGGAGGGTG    ACAGTGGCCG      1997

CCCAAGGCCA    CGAGCTTGTT    CTTTGTTCTT    TGTCACAGGG    ACTGAAAACC    TCTCCTCATG      2057

TTCTGCTTTC    GATTCGTTAA    GAGAGCAACA    TTTTACCCAC    ACACAGATAA    AGTTTTCCCT      2117

TGAGGAAACA    ACAGCTTTAA    AAAAAAAAA    GGAATTC                                      2154
```

( 2 ) INFORMATION FOR SEQ ID NO:2:

( i ) SEQUENCE CHARACTERISTICS:

( A ) LENGTH: 378 amino acids ( B ) TYPE: amino acid
( D ) TOPOLOGY: linear ( i i ) MOLECULE TYPE: protein ( x i ) SEQUENCE DESCRIPTION: SEQ ID NO:2:

| Met | Asp | Leu | Gly | Lys | Pro | Met | Lys | Ser | Val | Leu | Val | Ala | Leu | Leu |
| 1 | | | | 5 | | | | | 10 | | | | | 15 |

| Val | Ile | Phe | Gln | Val | Cys | Leu | Cys | Gln | Asp | Glu | Val | Thr | Asp | Tyr |
| | | | 20 | | | | 25 | | | | | 30 | | |

| Ile | Gly | Asp | Asn | Thr | Thr | Val | Asp | Tyr | Thr | Leu | Phe | Glu | Ser | Leu | Cys |
| | | 35 | | | | | 40 | | | | | 45 | | | |

| Ser | Lys | Lys | Asp | Val | Arg | Asn | Phe | Lys | Ala | Trp | Phe | Leu | Pro | Ile | Met |
| | 50 | | | | | 55 | | | | | 60 | | | | |

| Tyr | Ser | Ile | Ile | Cys | Phe | Val | Gly | Leu | Leu | Gly | Asn | Gly | Leu | Val | Val |
| 65 | | | | | 70 | | | | | 75 | | | | | 80 |

| Leu | Thr | Tyr | Ile | Tyr | Phe | Lys | Arg | Leu | Lys | Thr | Met | Thr | Asp | Thr | Tyr |
| | | | | 85 | | | | | 90 | | | | | 95 | |

| Leu | Leu | Asn | Leu | Ala | Val | Ala | Asp | Ile | Leu | Phe | Leu | Leu | Thr | Leu | Pro |
| | | | 100 | | | | | 105 | | | | | 110 | | |

| Phe | Trp | Ala | Tyr | Ser | Ala | Ala | Lys | Ser | Trp | Val | Phe | Gly | Val | His | Phe |
| | | | 115 | | | | | 120 | | | | | 125 | | |

| Cys | Lys | Leu | Ile | Phe | Ala | Ile | Tyr | Lys | Met | Ser | Phe | Phe | Ser | Gly | Met |
| | 130 | | | | | 135 | | | | | 140 | | | | |

| Leu | Leu | Leu | Leu | Cys | Ile | Ser | Ile | Asp | Arg | Tyr | Val | Ala | Ile | Val | Gln |
| 145 | | | | | 150 | | | | | 155 | | | | | 160 |

| Ala | Val | Ser | Ala | His | Arg | His | Arg | Ala | Arg | Val | Leu | Leu | Ile | Ser | Lys |
| | | | | 165 | | | | | 170 | | | | | 175 | |

| Leu | Ser | Cys | Val | Gly | Ser | Ala | Ile | Leu | Ala | Thr | Val | Leu | Ser | Ile | Pro |
| | | | 180 | | | | | 185 | | | | | 190 | | |

| Glu | Leu | Leu | Tyr | Ser | Asp | Leu | Gln | Arg | Ser | Ser | Ser | Glu | Gln | Ala | Met |
| | | 195 | | | | | 200 | | | | | 205 | | | |

| Arg | Cys | Ser | Leu | Ile | Thr | Glu | His | Val | Glu | Ala | Phe | Ile | Thr | Ile | Gln |
| | 210 | | | | | 215 | | | | | 220 | | | | |

| Val | Ala | Gln | Met | Val | Ile | Gly | Phe | Leu | Val | Pro | Leu | Leu | Ala | Met | Ser |
| 225 | | | | | 230 | | | | | 235 | | | | | 240 |

| Phe | Cys | Tyr | Leu | Val | Ile | Ile | Arg | Thr | Leu | Leu | Gln | Ala | Arg | Asn | Phe |
| | | | | 245 | | | | | 250 | | | | | 255 | |

| Glu | Arg | Asn | Lys | Ala | Ile | Lys | Val | Ile | Ile | Ala | Val | Val | Val | Val | Phe |
| | | | 260 | | | | | 265 | | | | | 270 | | |

| Ile | Val | Phe | Gln | Leu | Pro | Tyr | Asn | Gly | Val | Val | Leu | Ala | Gln | Thr | Val |
| | | 275 | | | | | 280 | | | | | 285 | | | |

| Ala | Asn | Phe | Asn | Ile | Thr | Ser | Ser | Thr | Cys | Glu | Leu | Ser | Lys | Gln | Leu |
| | 290 | | | | | 295 | | | | | 300 | | | | |

| Asn | Ile | Ala | Tyr | Asp | Val | Thr | Tyr | Ser | Leu | Ala | Cys | Val | Arg | Cys | Cys |
| 305 | | | | | 310 | | | | | 315 | | | | | 320 |

| Val | Asn | Pro | Phe | Leu | Tyr | Ala | Phe | Ile | Gly | Val | Lys | Phe | Arg | Asn | Asp |
| | | | | 325 | | | | | 330 | | | | | 335 | |

| Ile | Phe | Lys | Leu | Phe | Lys | Asp | Leu | Gly | Cys | Leu | Ser | Gln | Glu | Gln | Leu |
| | | | 340 | | | | | 345 | | | | | 350 | | |

| Arg | Gln | Trp | Ser | Ser | Cys | Arg | His | Ile | Arg | Arg | Ser | Ser | Met | Ser | Val |
| | | 355 | | | | | 360 | | | | | 365 | | | |

| Glu | Ala | Glu | Thr | Thr | Thr | Thr | Phe | Ser | Pro |
| | 370 | | | | | 375 | | | |

( 2 ) INFORMATION FOR SEQ ID NO:3:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Leu Thr Tyr Ile Tyr Phe Lys Arg Leu Lys Thr Met Thr Asp Thr Tyr
1               5                   10                  15

Leu Leu Asn Leu Ala Val Ala Asp Ile Leu Phe Leu Leu Thr Leu Pro
            20                  25                  30

Phe Trp Ala Tyr Ser Ala Ala Lys
            35                  40
```

( 2 ) INFORMATION FOR SEQ ID NO:4:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Val Ile Leu Val Met Tyr Arg His Thr Lys Met Lys Thr Ala Thr Asn
1               5                   10                  15

Ile Tyr Ile Phe Asn Leu Ala Leu Ala Asp Thr Leu Val Leu Leu Thr
            20                  25                  30

Leu Pro Phe Gln Gly Thr Asp Ile Leu Leu Gly
            35                  40
```

( 2 ) INFORMATION FOR SEQ ID NO:5:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Val Met Phe Gly Ile Val Arg Tyr Thr Lys Leu Lys Thr Ala Thr Asn
1               5                   10                  15

Ile Tyr Ile Phe Asn Leu Ala Leu Ala Asp Ala Leu Ala Thr Ser Thr
            20                  25                  30

Leu Pro Phe Gln Ser Ala Lys Tyr Leu Met Glu
            35                  40
```

( 2 ) INFORMATION FOR SEQ ID NO:6:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Val Met Tyr Val Ile Val Arg Tyr Thr Lys Leu Lys Thr Ala Thr Asn
1               5                   10                  15
```

( 2 ) INFORMATION FOR SEQ ID NO:7:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Ile Tyr Ile Phe Asn Leu Ala Leu Ala Asp Ala Leu Ala Thr Ser Thr
             20                  25                  30

Leu Pro Phe Gln Ser Val Asn Tyr Leu Met Gly
         35                  40
```

( 2 ) INFORMATION FOR SEQ ID NO:7:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Leu Val Phe Val Ile Val Arg Tyr Thr Lys Met Lys Thr Thr Thr Ala
1               5                   10                  15

Thr Asn Ile Tyr Ile Phe Asn Leu Ala Leu Ala Asp Ala Leu Val Thr
             20                  25                  30

Thr Thr Met Pro Phe Gln Ser Ala Val Tyr Leu Met Asn
         35                  40                  45
```

( 2 ) INFORMATION FOR SEQ ID NO:8:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Val Met Tyr Val Ile Thr Leu Arg His Thr Lys Met Lys Thr Ala Thr
1               5                   10                  15

Asn Ile Tyr Ile Phe Ile Asn Leu Ala Leu Ala Asp Thr Leu Val Leu
             20                  25                  30

Leu Thr Leu Pro Phe Gln Gly Thr Asp Ile Leu Leu Gly
         35                  40                  45
```